(12) United States Patent
Bartels et al.

(10) Patent No.: US 10,669,276 B2
(45) Date of Patent: Jun. 2, 2020

(54) FUSED PYRIMIDINE DERIVATIVES

(71) Applicant: Hoffmann-La Roche Inc., Little Falls, NJ (US)

(72) Inventors: Bjoern Bartels, Basel (CH); Roland Jakob-Roetne, Basel (CH); Anja Limberg, Basel (CH); Werner Neidhart, Basel (CH); Hasane Ratni, Basel (CH); Sandra Steiner, Basel (CH); Michael Reutlinger, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 16/231,177

(22) Filed: Dec. 21, 2018

(65) Prior Publication Data
US 2019/0256517 A1    Aug. 22, 2019

Related U.S. Application Data

(63) Continuation of application No. PCT/EP2017/066521, filed on Jul. 3, 2017.

(30) Foreign Application Priority Data

Jul. 8, 2016  (EP) ..................... 16178674

(51) Int. Cl.
*A61K 31/519*    (2006.01)
*C07D 487/04*    (2006.01)
(Continued)

(52) U.S. Cl.
CPC ............ *C07D 487/04* (2013.01); *A61P 25/28* (2018.01); *C07D 471/04* (2013.01)

(58) Field of Classification Search
CPC ............................. A61K 31/519; C07D 487/04
(Continued)

(56) References Cited

FOREIGN PATENT DOCUMENTS

EP    2 050 749 A1    4/2009
WO    2009/073779 A1    6/2009
(Continued)

OTHER PUBLICATIONS

Bai et al., "An atomic structure of human γ-secretase" Nature 525:212-217 (Sep. 10, 2015).
(Continued)

*Primary Examiner* — Jeffrey H Murray
(74) *Attorney, Agent, or Firm* — Genentech, Inc.; Richard G. A. Bone

(57) ABSTRACT

The present invention relates to compounds of formula I,

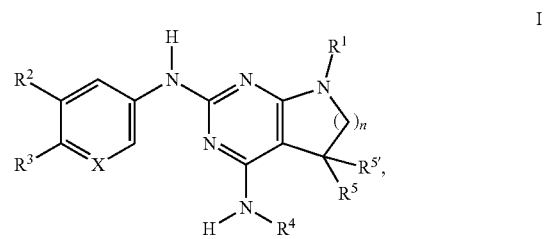

wherein
$R^1$ is phenyl, lower alkyl, $C_{3-6}$-cycloalkyl, —$CH_2$—$C_{3-6}$-cycloalkyl, or bridged $C_{3-5}$-cycloalkyl, optionally substituted by one, two or three substituents, selected from halogen, lower alkyl or lower alkyl substituted by halogen;
$R^2$ is hydrogen, halogen, lower alkoxy, lower alkyl substituted by halogen or lower alkoxy substituted by halogen;
$R^3$ is a five membered heteroaryl group, selected from

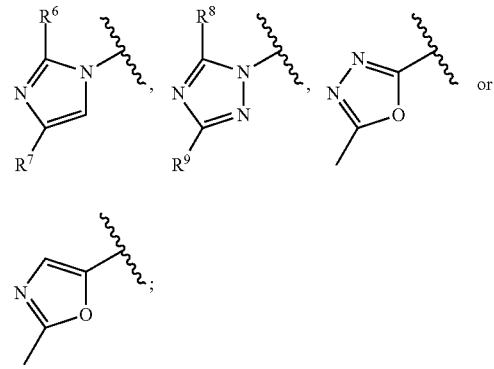

wherein
$R^6$ is hydrogen or lower alkyl;
$R^7$ is halogen or lower alkyl;
$R^8$ is hydrogen or lower alkyl;
$R^9$ is hydrogen or lower alkyl;
$R^4$ is lower alkyl or lower alkyl substituted by hydroxy;
$R^5/R^{5'}$ is independently from each other hydrogen or lower alkyl;
-$( )_n$- is —$CH_2$— or —$CH_2CH_2$— for n being 1 or 2;
X is CH or N;
or to pharmaceutically active acid addition salts thereof, to racemic mixtures or to its corresponding enantiomers and/or optical isomers and/or stereoisomers thereof.
The compounds may be used for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome.

24 Claims, No Drawings

(51) Int. Cl.
*A61P 25/28* (2006.01)
*C07D 471/04* (2006.01)

(58) Field of Classification Search
USPC .................................... 514/265.1; 544/280
See application file for complete search history.

(56) References Cited

FOREIGN PATENT DOCUMENTS

| | | |
|---|---|---|
| WO | 2009/076337 A1 | 6/2009 |
| WO | 2011/086098 A1 | 7/2011 |
| WO | 2015/018534 A1 | 2/2015 |
| WO | 2015/066687 A1 | 5/2015 |
| WO | 2015/109109 A1 | 7/2015 |
| WO | 2015/153709 A1 | 10/2015 |

OTHER PUBLICATIONS

Beher et al., "Selected Non-steroidal Anti-inflammatory Drugs and Their Derivatives Target g-Secretase at a Novel Site" Journal of Biological Chemistry 279(42):43419-43426 ( 2004).
Bian et al., "Synthesis of 2-[2H]-2-(1-methylalkyl)succinic acids" Chinese Chemical Letters 26(5):619-622 (May 2015).
Bursavich et al., "Gamma Secretase Modulators: New Alzheimer's Drugs on the Horizon?" Journal of Medicinal Chemistry 59:7389-7409 ( 2016).
Clarke et al., "Intra- or Intercomplex Binding to the g-Secretase Enzyme" Journal of Biological Chemistry 281(42):31279-31289 (Oct. 20, 2006).
Crump et al., "Development and Mechanism of γ-Secretase Modulators for Alzheimer's Disease" Biochemistry 52:3197-3216 ( 2013).
Ebke et al., "Novel g-Secretase Enzyme Modulators Directly Target Presenilin Protein*S" Journal of Biological Chemistry 286(43):37181-37186 (Oct. 28, 2011).
Hall et al., "γ-Secretase Modulators: Current Status and Future Directions" Progress in Medicinal Chemistry 53:101-145 ( 2014).
ISR and Written Opinion for PCT/EP2017/066521 (dated Sep. 12, 2017).
Jantzen et al., "Microglial Activation and b-Amyloid Deposit Reduction Caused by a Nitric Oxide-Releasing Nonsteroidal Anti-Inflammatory Drug in Amyloid Precursor Protein Plus Presenilin-1 Transgenic Mice" Journal of Neuroscience 22:2246-2254 (Mar. 15, 2002).
Kukar et al., "Diverse compounds mimic Alzheimer disease—causing mutations by augmenting Ab42 production" Nature Medicine 11:545-550 (May 2005).
Lleo et al., "Nonsteroidal anti-inflammatory drugs lower Ab42 and change presenilin 1 conformation" Nature Medicine 10:1065-1066 (Oct. 2004).
Morihara et al., "Selective inhibition of Aβ42 production by NSAID R-enantiomers" Journal of Neurochemistry 83:1009-1012 ( 2002).
Narlawar et al., "Scaffold of the Cyclooxygenase-2 (COX-2) Inhibitor Carprofen Provides Alzheimer G-Secretase Modulators" Journal of Medicinal Chemistry 49:7588-7591 ( 2006).
Oehlrich et al., "γ-Secretase Modulators as Potential Disease Modifying Anti-Alzheimer's Drugs" Journal of Medicinal Chemistry 54:669-698 ( 2011).
Peretto et al., "Synthesis and Biological Activity of Flurbiprofen Analogues as Selective Inhibitors of B-Amyloid1-42 Secretion" Journal of Medicinal Chemistry 48:5705-5720 ( 2005).
Stock et al., "The geminal dimethyl analogue of Flurbiprofen as a novel Ab42 inhibitor and potential Alzheimer's disease modifying agent" Bioorganic & Medicinal Chemistry Letters 16:2219-2223 ( 2006).
Takahashi et al., "Sulindac Sulfide is a Noncompetitive g-Secretase Inhibitor That Preferentially Reduces Ab42 Generation*" Journal of Biological Chemistry 278(20):18664-18670 ( 2003).
Weggen et al., "A subset of NSAIDs lower amyloidogenic Aβ42 independently of cyclooxygenase activity" Nature 414:212-216 (Nov. 8, 2001).

FUSED PYRIMIDINE DERIVATIVES

CROSS-REFERENCE TO RELATED APPLICATIONS

This application is a continuation of, and claims priority to, International Patent Application No. PCT/EP2017/066521, filed on Jul. 3, 2017, which claims benefit of priority to European Patent Application No. 16178674.4, filed on Jul. 8, 2016. The entire contents of each of the above patent applications are hereby incorporated by reference.

SUMMARY

The present invention relates to compounds of formula I,

I wherein
$R^1$ is phenyl, lower alkyl, $C_{3-6}$-cycloalkyl, —$CH_2$—$C_{3-6}$-cycloalkyl, or bridged $C_{3-5}$-cycloalkyl, optionally substituted by one, two or three substituents, selected from halogen, lower alkyl or lower alkyl substituted by halogen;
$R^2$ is hydrogen, halogen, lower alkoxy, lower alkyl substituted by halogen or lower alkoxy substituted by halogen;
$R^3$ is a five membered heteroaryl group, selected from or wherein
$R^6$ is hydrogen or lower alkyl;
$R^7$ is halogen or lower alkyl;
$R^8$ is hydrogen or lower alkyl;
$R^9$ is hydrogen or lower alkyl;
$R^4$ is lower alkyl or lower alkyl substituted by hydroxy;
$R^5/R^{5'}$ is independently from each other hydrogen or lower alkyl;
-( )$_n$- is —$CH_2$— or —$CH_2CH_2$ for n being 1 or 2;
X is CH or N;

or to pharmaceutically active acid addition salts thereof, to racemic mixtures or to its corresponding enantiomers and/or optical isomers and/or stereoisomers thereof.

DESCRIPTION

Now it has been found that the present compounds of formula I are modulators of γ-secretase, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFβ) containing the TM- and cytoplasmatic domain. CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g., Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a high molecular weight complex that consists of four essential subunits: Presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, Nature 2015, 525, pages 212-217). The presenilins are bearing the catalytic site and represent a group of atypical aspartyl proteases which cleave their substrates within the TM of and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e., ablation of the presenilin genes and by low-molecular-weight inhibitory compounds. According to the amyloid cascade hypothesis for AD the production and deposition of Aβ is the ultimate cause for the disease.

Therefore, it was believed that selective and potent inhibition of γ-secretase might be useful for the prevention and treatment of AD.

An alternative mode of treatment is the modulation of the γ-secretase activity which results in a selective reduction of the Aβ42 production. This will lead in an increase of shorter Aβ isoforms, such as Aβ38, Aβ37 or others, which have no or reduced capability for aggregation and plaque formation, and are not or less neurotoxic. Compounds which show this effect on modulating γ-secretase activity include certain non-steroidal anti-inflammatory drugs (NSAIDs) and related analogues (Weggen et al. Nature, 414 (2001) 212-16).

Thus, the compounds of this invention will be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Numerous documents describe the current knowledge on γ-secretase modulation, for example the following publications:

Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91
Ebke et al, J. Biol. Chem., 286 (2011) 37181-86
Oehlrich, Gijsen et al, J. Med. Chem., 54 (2011) 669-698
Li et al, Biochemistry, 52 (2013) 3197-3216
Hall et al, Progress in Med. Chem., 53 (2014) 101-145
Bursavich et al, J. Med. Chem., 59 (2016) 7389-7409

The following definitions for compounds of formula I are used:

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a saturated straight- or branched-chain group containing from 1 to 7 carbon atoms as defined for lower alky, which group is connected via an O-atom, for example methoxy, ethoxy and the like. Preferred alkoxy group is methoxy ($OCH_3$).

As used herein, the term "lower alkyl substituted by halogen" denotes an alkyl group as defined above, wherein at least one hydrogen atom is replaced by halogen, for example $CF_3$, $CHF_2$, $CH_2F$, $CHFCF_3$, $CH_2CHF_2$, $CH_2CH_2F$, $CH_2C(CH_3)_2CF_3$, $CH_2CF_2CF_3$, $CH(CF_3)_2$, $CH_2CF_3$, $(CH_2)_2CF_3$, $(CH_2)_3CF_3$, $CH(CH_3)CF_3$, $CF_2CF_3$, and the like.

As used herein, the term "lower alkyl substituted by hydroxy" denotes an alkyl group as defined above, wherein at least one hydrogen atom is replaced by hydroxy, for example $(CH_2)_2OH$.

The term "halogen" denotes chlorine, iodine, fluorine and bromine.

The term "$C_{3-6}$-cycloalkyl" is selected from the group consisting of

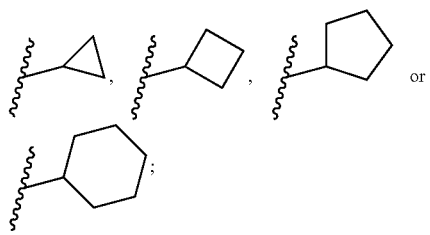

The term "—$CH_2$—$C_{3-6}$-cycloalkyl", is selected from the group consisting of

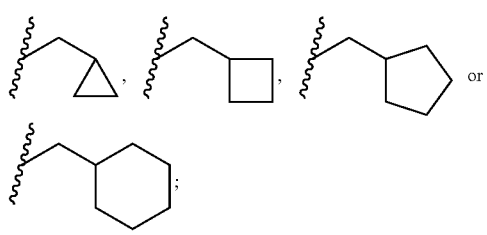

The term "bridged $C_{4-7}$-cycloalkyl" is an alkyl ring system, containing 4 to 7 ring-carbon atoms, in which two carbon atoms of a basic $C_{3-6}$-cycloalkyl ring system as defined above are bridged by a single bond, —$CH_2$— or —$CH_2CH_2$—.
for example

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Objects of the present invention are compounds of formula I, the use of such compounds for the preparation of medicaments for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome, their manufacture and medicaments based on a compound of formula I in accordance with the invention.

Further objects of the invention are all forms of optically pure enantiomers, racemates or diastereomeric mixtures for compounds of formula I.

One object of the invention is a compound of formula I-1

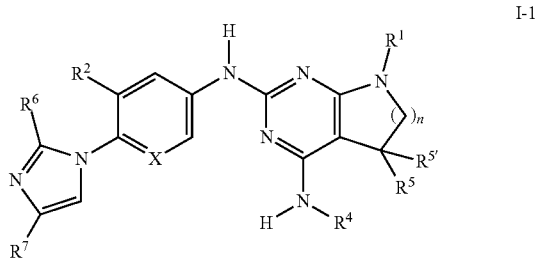

wherein
R¹ is phenyl, lower alkyl, $C_{3-6}$-cycloalkyl, —$CH_2$—$C_{3-6}$-cycloalkyl, or bridged $C_{3-5}$-cycloalkyl, optionally substituted by one, two or three substituents, selected from halogen, lower alkyl or lower alkyl substituted by halogen;
R² is hydrogen, halogen, lower alkoxy, lower alkyl substituted by halogen or lower alkoxy substituted by halogen;
R⁴ is lower alkyl or lower alkyl substituted by hydroxy;
R⁵/R⁵' is independently from each other hydrogen or lower alkyl;
R⁶ is hydrogen or lower alkyl;
R⁷ is halogen or lower alkyl;
-( )$_n$- is —$CH_2$— or —$CH_2CH_2$— for n being 1 or 2;
X is CH or N;
or pharmaceutically active acid addition salts thereof, racemic mixtures or its corresponding enantiomers and/or optical isomers and/or stereoisomers thereof, for example the following compounds:
N2-(4-(4-Chloro-1H-imidazol-1-yl)-3-methoxyphenyl)-7-(4-fluorophenyl)-N4,5,5-trimethyl-6,7-dihydro-5H-pyrrolo[2,3-d]pyrimidine-2,4-diamine;
N2-(6-(4-Chloro-1H-imidazol-1-yl)-5-methoxypyridin-3-yl)-7-(4-fluorophenyl)-N4,5,5-trimethyl-6,7-dihydro-5H-pyrrolo[2,3-d]pyrimidine-2,4-diamine;
7-(4-Fluorophenyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine;
N2-(4-(2,4-Dimethyl-1H-imidazol-1-yl)-3-fluorophenyl)-7-(4-fluorophenyl)-N4,5,5-trimethyl-6,7-dihydro-5H-pyrrolo[2,3-d]pyrimidine-2,4-diamine;
7-(4-Fluorophenyl)-N4,5,5-trimethyl-N2-(4-(4-methyl-1H-imidazol-1-yl)phenyl)-6,7-dihydro-5H-pyrrolo[2,3-d]pyrimidine-2,4-diamine;
N2-(6-(4-Chloro-1H-imidazol-1-yl)-5-methoxypyridin-3-yl)-7-(3,4-difluorophenyl)-N4,5,5-trimethyl-6,7-dihydro-5H-pyrrolo[2,3-d]pyrimidine-2,4-diamine;
7-(3,4-Difluorophenyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine;
7-(3,3-Difluorocyclobutyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine;
7-(2,4-Difluorophenyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine;
N2-(5-Methoxy-6-(4-methyl-1H-imidazol-1-yl)pyridin-3-yl)-N4,5,5-trimethyl-7-(3-(trifluoromethyl)bicyclo[1.1.1]pentan-1-yl)-6,7-dihydro-5H-pyrrolo[2,3-d]pyrimidine-2,4-diamine;
N2-(6-(4-Chloro-1H-imidazol-1-yl)-5-methoxypyridin-3-yl)-7-(2,4-difluorophenyl)-N4,5,5-trimethyl-6,7-dihydro-5H-pyrrolo[2,3-d]pyrimidine-2,4-diamine;
N2-(5-Fluoro-6-(4-methyl-1H-imidazol-1-yl)pyridin-3-yl)-7-(4-fluorophenyl)-N4,5,5-trimethyl-6,7-dihydro-5H-pyrrolo[2,3-d]pyrimidine-2,4-diamine;
7-(2,4-Difluorophenyl)-N2-(5-fluoro-6-(4-methyl-1H-imidazol-1-yl)pyridin-3-yl)-N4,5,5-trimethyl-6,7-dihydro-5H-pyrrolo[2,3-d]pyrimidine-2,4-diamine;
2-((7-(4-Fluorophenyl)-2-((5-methoxy-6-(4-methyl-1H-imidazol-1-yl)pyridin-3-yl)amino)-5,5-dimethyl-6,7-dihydro-5H-pyrrolo[2,3-d]pyrimidin-4-yl)amino)ethanol;
2-((2-((6-(4-Chloro-1H-imidazol-1-yl)-5-methoxypyridin-3-yl)amino)-7-(4-fluorophenyl)-5,5-dimethyl-6,7-dihydro-5H-pyrrolo[2,3-d]pyrimidin-4-yl)amino)ethanol;
7-(4-Fluorophenyl)-N2-(5-methoxy-6-(4-methyl-1H-imidazol-1-yl)pyridin-3-yl)-N4-methyl-6,7-dihydro-5H-pyrrolo[2,3-d]pyrimidine-2,4-diamine;
N2-(3-Fluoro-4-(4-methyl-1H-imidazol-1-yl)phenyl)-7-(4-fluorophenyl)-N4,5,5-trimethyl-6,7-dihydro-5H-pyrrolo[2,3-d]pyrimidine-2,4-diamine;
N2-(5-Fluoro-6-(4-methyl-1H-imidazol-1-yl)pyridin-3-yl)-8-(4-fluorophenyl)-N4,5,5-trimethyl-5,6,7,8-tetrahydropyrido[2,3-d]pyrimidine-2,4-diamine;
N2-(3-Fluoro-4-(4-methyl-1H-imidazol-1-yl)phenyl)-8-(4-fluorophenyl)-N4,5,5-trimethyl-5,6,7,8-tetrahydropyrido[2,3-d]pyrimidine-2,4-diamine;
N2-(3-Fluoro-4-(4-methyl-1H-imidazol-1-yl)phenyl)-7-(4-fluorophenyl)-N4-methyl-6,7-dihydro-5H-pyrrolo[2,3-d]pyrimidine-2,4-diamine;
7-(4-Fluorophenyl)-N2-(5-methoxy-6-(4-methyl-1H-imidazol-1-yl)pyridin-3-yl)-N4,5-dimethyl-6,7-dihydro-5H-pyrrolo[2,3-d]pyrimidine-2,4-diamine;
7-(2,3-Difluorophenyl)-N2-(5-fluoro-6-(4-methyl-1H-imidazol-1-yl)pyridin-3-yl)-N4,5,5-trimethyl-6,7-dihydro-5H-pyrrolo[2,3-d]pyrimidine-2,4-diamine;
7-(2,3-Difluorophenyl)-N2-(3-fluoro-4-(4-methyl-1H-imidazol-1-yl)phenyl)-N4,5,5-trimethyl-6,7-dihydro-5H-pyrrolo[2,3-d]pyrimidine-2,4-diamine;
7-(2,3-Difluorophenyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine;
7-(2-Chloro-4-fluorophenyl)-N2-(3-fluoro-4-(4-methyl-1H-imidazol-1-yl)phenyl)-N4,5,5-trimethyl-6,7-dihydro-5H-pyrrolo[2,3-d]pyrimidine-2,4-diamine;
(S)—N2-(3-Fluoro-4-(4-methyl-1H-imidazol-1-yl)phenyl)-7-(4-fluorophenyl)-N4,5-dimethyl-6,7-dihydro-5H-pyrrolo[2,3-d]pyrimidine-2,4-diamine; or
(R)—N2-(3-Fluoro-4-(4-methyl-1H-imidazol-1-yl)phenyl)-7-(4-fluorophenyl)-N4,5-dimethyl-6,7-dihydro-5H-pyrrolo[2,3-d]pyrimidine-2,4-diamine.

One object of the invention is a compound of formula I-2

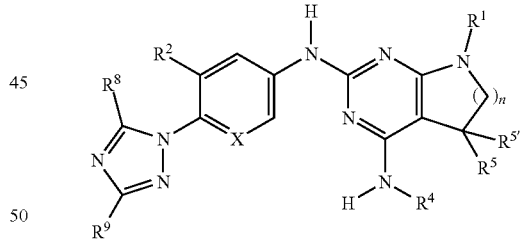

wherein
R¹ is phenyl, lower alkyl, $C_{3-6}$-cycloalkyl, —$CH_2$—$C_{3-6}$-cycloalkyl, or bridged $C_{3-5}$-cycloalkyl, optionally substituted by one, two or three substituents, selected from halogen, lower alkyl or lower alkyl substituted by halogen;
R² is hydrogen, halogen, lower alkoxy, lower alkyl substituted by halogen or lower alkoxy substituted by halogen;
R⁴ is lower alkyl or lower alkyl substituted by hydroxy;
R⁵/R⁵' is independently from each other hydrogen or lower alkyl;
R⁸ is hydrogen or lower alkyl;
R⁹ is halogen or lower alkyl;
-( )$_n$- is —$CH_2$— or —$CH_2CH_2$— for n being 1 or 2;
X is CH or N;

or pharmaceutically active acid addition salts thereof, racemic mixtures or its corresponding enantiomers and/or optical isomers and/or stereoisomers thereof, for example the following compounds:

7-(4-Fluorophenyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine;

N2-(3-(Difluoromethoxy)-4-(3-methyl-1H-1,2,4-triazol-1-yl)phenyl)-7-(4-fluorophenyl)-N4,5,5-trimethyl-6,7-dihydro-5H-pyrrolo[2,3-d]pyrimidine-2,4-diamine;

N2-(3-Fluoro-4-(3-methyl-1H-1,2,4-triazol-1-yl)phenyl)-7-(4-fluorophenyl)-N4,5,5-trimethyl-6,7-dihydro-5H-pyrrolo[2,3-d]pyrimidine-2,4-diamine;

N2-(3-Fluoro-4-(5-methyl-1H-1,2,4-triazol-1-yl)phenyl)-7-(4-fluorophenyl)-N4,5,5-trimethyl-6,7-dihydro-5H-pyrrolo[2,3-d]pyrimidine-2,4-diamine;

7-(3,4-Difluorophenyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine;

7-(3,4-Difluorophenyl)-N2-(3-fluoro-4-(3-methyl-1H-1,2,4-triazol-1-yl)phenyl)-N4,5,5-trimethyl-6,7-dihydro-5H-pyrrolo[2,3-d]pyrimidine-2,4-diamine;

7-(4-Fluorophenyl)-N4,5,5-trimethyl-N2-(4-(3-methyl-1H-1,2,4-triazol-1-yl)phenyl)-6,7-dihydro-5H-pyrrolo[2,3-d]pyrimidine-2,4-diamine;

7-(4-Fluorophenyl)-N4,5,5-trimethyl-N2-(6-(3-methyl-1H-1,2,4-triazol-1-yl)pyridin-3-yl)-6,7-dihydro-5H-pyrrolo[2,3-d]pyrimidine-2,4-diamine;

7-(3,3-Difluorocyclobutyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine;

7-(2,4-Difluorophenyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine;

N2-(3-Methoxy-4-(3-methyl-1H-1,2,4-triazol-1-yl)phenyl)-N4,5,5-trimethyl-7-(3-(trifluoromethyl)bicyclo[1.1.1]pentan-1-yl)-6,7-dihydro-5H-pyrrolo[2,3-d]pyrimidine-2,4-diamine;

7-(2,4-Difluorophenyl)-N2-(3-fluoro-4-(3-methyl-1H-1,2,4-triazol-1-yl)phenyl)-N4,5,5-trimethyl-6,7-dihydro-5H-pyrrolo[2,3-d]pyrimidine-2,4-diamine;

2-((7-(4-Fluorophenyl)-2-((3-methoxy-4-(3-methyl-1H-1,2,4-triazol-1-yl)phenyl)amino)-5,5-dimethyl-6,7-dihydro-5H-pyrrolo[2,3-d]pyrimidin-4-yl)amino)ethanol;

2-((2-((3-Fluoro-4-(3-methyl-1H-1,2,4-triazol-1-yl)phenyl)amino)-7-(4-fluorophenyl)-5,5-dimethyl-6,7-dihydro-5H-pyrrolo[2,3-d]pyrimidin-4-yl)amino)ethanol;

7-(4-Fluorophenyl)-N2-(3-methoxy-4-(3-methyl-1H-1,2,4-triazol-1-yl)phenyl)-N4-methyl-6,7-dihydro-5H-pyrrolo[2,3-d]pyrimidine-2,4-diamine;

8-(4-Fluorophenyl)-N2-(3-methoxy-4-(3-methyl-1H-1,2,4-triazol-1-yl)phenyl)-N4,5,5-trimethyl-5,6,7,8-tetrahydropyrido[2,3-d]pyrimidine-2,4-diamine;

7-(4-Fluorophenyl)-N2-(3-methoxy-4-(3-methyl-1H-1,2,4-triazol-1-yl)phenyl)-N4,5-dimethyl-6,7-dihydro-5H-pyrrolo[2,3-d]pyrimidine-2,4-diamine; or 7-(2,3-Difluorophenyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine.

One object of the invention is a compound of formula I-3

I-3 wherein
$R^1$ is phenyl, lower alkyl, $C_{3-6}$-cycloalkyl, —$CH_2$—$C_{3-6}$-cycloalkyl, or bridged $C_{3-5}$-cycloalkyl, optionally substituted by one, two or three substituents, selected from halogen, lower alkyl or lower alkyl substituted by halogen;
$R^2$ is hydrogen, halogen, lower alkoxy, lower alkyl substituted by halogen or lower alkoxy substituted by halogen;
$R^4$ is lower alkyl or lower alkyl substituted by hydroxy;
$R^5/R^{5'}$ is independently from each other hydrogen or lower alkyl;
-( )$_n$- is —$CH_2$— or —$CH_2CH_2$— for n being 1 or 2;
X is CH or N;
or pharmaceutically active acid addition salts thereof, racemic mixtures or its corresponding enantiomers and/or optical isomers and/or stereoisomers thereof, for example the following compounds:

7-(4-Fluorophenyl)-N2-(3-methoxy-4-(5-methyl-1,3,4-oxadiazol-2-yl)phenyl)-N4,5,5-trimethyl-6,7-dihydro-5H-pyrrolo[2,3-d]pyrimidine-2,4-diamine, or 7-(4-Fluorophenyl)-N4,5,5-trimethyl-N2-(4-(5-methyl-1,3,4-oxadiazol-2-yl)phenyl)-6,7-dihydro-5H-pyrrolo[2,3-d]pyrimidine-2,4-diamine.

One object of the invention is a compound of formula I-4

I-4 wherein
$R^1$ is phenyl, lower alkyl, $C_{3-6}$-cycloalkyl, —$CH_2$—$C_{3-6}$-cycloalkyl, or bridged $C_{3-5}$-cycloalkyl, optionally substituted by one, two or three substituents, selected from halogen, lower alkyl or lower alkyl substituted by halogen;
$R^2$ is hydrogen, halogen, lower alkoxy, lower alkyl substituted by halogen or lower alkoxy substituted by halogen;
$R^4$ is lower alkyl or lower alkyl substituted by hydroxy;
$R^5/R^{5'}$ is independently from each other hydrogen or lower alkyl;
-( )$_n$- is —$CH_2$— or —$CH_2CH_2$— for n being 1 or 2;
X is CH or N;
or pharmaceutically active acid addition salts thereof, racemic mixtures or its corresponding enantiomers and/or optical isomers and/or stereoisomers thereof, for example the following compound:

N2-(3-Fluoro-4-(2-methyloxazol-5-yl)phenyl)-7-(4-fluorophenyl)-N4,5,5-trimethyl-6,7-dihydro-5H-pyrrolo[2,3-d]pyrimidine-2,4-diamine.

The present compounds of formula I and their pharmaceutically acceptable salts can be prepared by methods known in the art, for example, by processes described below, which processes comprise a) reacting a compound of formula II

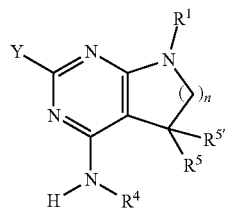

with a compound of formula III

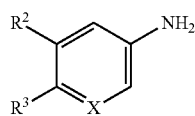

to form a compound of formula I

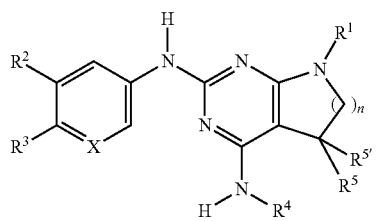

wherein the substituents have the meaning as described above and Y is halogen, and, if desired, converting the compounds obtained into pharmaceutically acceptable acid addition salts;
or b) reacting a compound of formula V

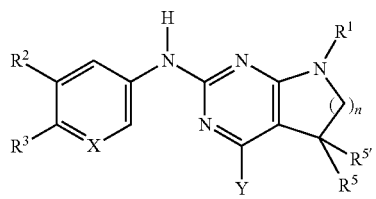

with a compound of formula

to form a compound of formula I

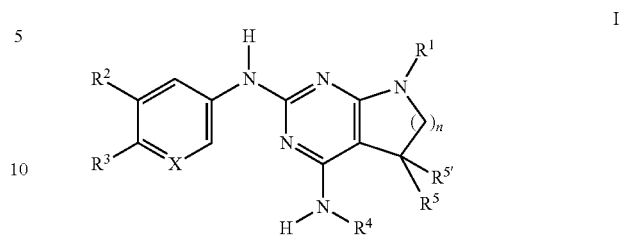

wherein the groups have the meaning as described above and Y is halogen, and if desired converting the compounds obtained into pharmaceutically acceptable acid addition salts.

In more detail, compounds of formula I and their intermediates may be prepared by schemes 1-8 and by the description of 47 specific examples.

Scheme 1

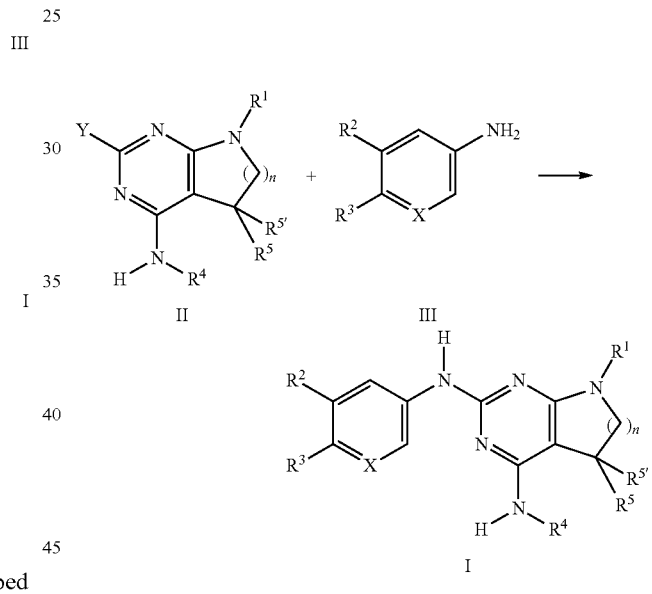

An intermediate of formula II, wherein n, $R^4$, $R^5$, $R^{5'}$ are as defined above and Y is halogen, preferably chorine or bromine, is reacted with a compound of formula III, wherein X, $R^2$, $R^3$ are as defined above, in the presence of catalytic or stoichiometric amounts of a suitable transition metal complex, e.g., bis(dibenzylideneacetone)palladium(0), and, respectively, catalytic or stoichiometric amounts of a suitable phosphine ligand, e.g., 2-dicyclohexylphosphino-2'-(N,N-dimethylamino)biphenyl, and, furthermore, in the presence of a suitable base, e.g., alkali carbonate or alkaliphosphate, e.g., cesium carbonate. The reaction can be carried out in a polar, aprotic solvent, e.g., N-methylpyrrolidinone or dimethylformamide, at temperatures between 100° C. and 170° C., preferably between 140° C. and 160° C., optionally under microwave radiation in a closed vial.

Alternatively, compounds of formula I can be synthesized as shown in Scheme 2 in a two step process.

Scheme 2

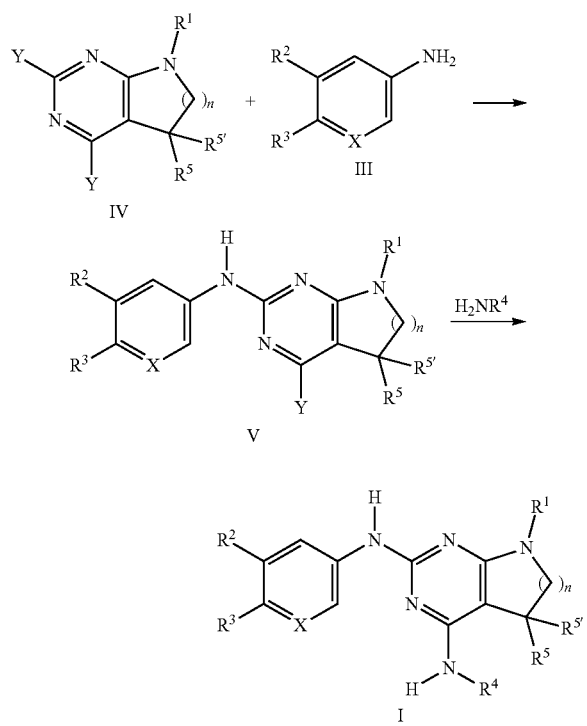

In the first step, an intermediate of formula IV, wherein n, $R^1$, $R^5$, $R^{5'}$ are as defined above and Y is each independently selected from halogen, preferably chorine, is reacted with a compound of formula III, wherein X, $R^2$, $R^3$ are as defined above, in the presence of a suitable base, e.g., trialkylamine, such as triethylamine or diisopropylethyl amine, in a polar solvent, e.g., N-methylpyrrolidinone, at elevated temperatures between 120° C. and 180° C., preferably between 150° C. and 170° C. Alternatively, an intermediate of formula V can be formed by reaction of an intermediate of formula IV with an intermediate of formula III in the presence of at least two equivalents of a strong, non-nucleophilic base, such as alkali bis(trialkylsilyl)amide or alkali diisopropylamide, e.g., lithium bis(trimethylsilyl)amide. Preferably, the base is added slowly during the reaction. The reaction can be carried out in a polar, aprotic solvent, e.g., tetrahydrofuran, at temperatures between 0° C. and 80° C., preferably between 50° C. and 60° C.

The second step, reaction of intermediate of formula V with an amine of formula $H_2NR^4$, wherein $R^4$ is as defined above, can be carried out using an excess of amine $H_2NR^4$, optionally as solution in a suitable solvent, such as ethanol or methanol. The transformation can be carried out at elevated temperatures of 100° C. to 140° C., preferably between 110° C. and 130° C., in a polar, high boiling solvent, such as N-methylpyrrolidinone or dimethylsulfoxide. For amines having a low boiling point, such as methylamine or ethylamine, the reaction is best carried out in a closed pressure vial or autoclave at high concentrations.

Scheme 3

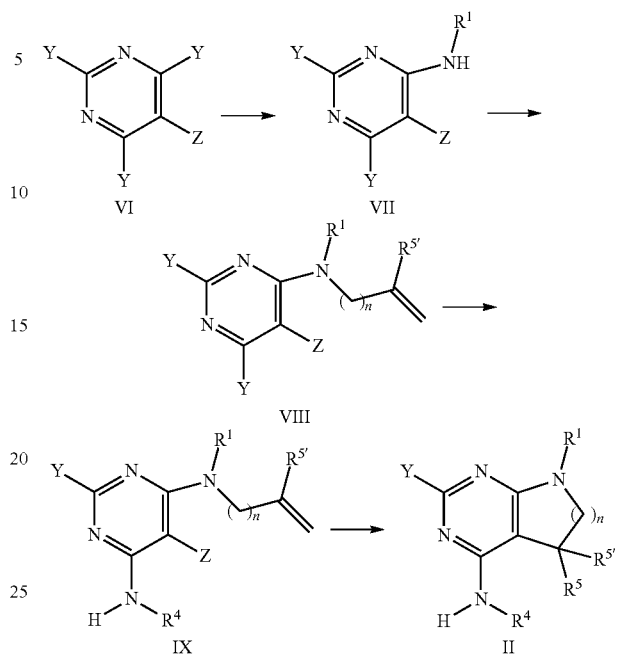

The intermediates of formula II can be prepared by methods known in the art. For example, intermediates of formula II, wherein $R^1$, $R^4$, $R^5$ and $R^{5'}$ are as defined above with the exception $R^{5'}$ is not hydrogen, and $R^5$ is methyl, can be accessed using the synthetic sequence depicted in Scheme 3. Pyrimidines of formula VI, wherein Y is each individually selected from halogen, preferably chlorine, and Z is selected from halogen, preferably bromine, can be reacted with amines of formula $H_2NR^1$, wherein $R^1$ is as defined above, in the presence of a non-nucleophilic base, such as sodium acetate or trialkylamine, e.g., triethyl amine or N,N-diisopropylethyl amine, or alkali hexamethyldisilazide, e.g., lithiumhexamethyldisilazide, in a suitable polar solvent, such as, e.g., tetrahydrofuran, acetonitrile or dichloromethane. In case the amine of formula $H_2NR^1$ is reacted in form of a salt, e.g., as hydrochloride, the free base has to be liberated prior to reaction, e.g., by increasing the stoichiometry of the base accordingly. In this case, the use of trialkyl amine as base is preferred. Thereafter, the intermediate of formula VII can be reacted with an appropriate alkylating agent LG-$[CH_2]_nC(R^{5'})$=$CH_2$, wherein n is 1 or 2, preferably 1, and the leaving group LG is halogen or sulfonate $OSO_2R'$, e.g., bromine, methylsulfonate, trifluoromethylsulfonate or tolylsulfonate, preferably bromine, and $R^{5'}$ is as defined above, with the exception $R^{5'}$ is not hydrogen, in the presence of a suitable non-nucleophilic base, e.g., sodium hydride, in a polar solvent, e.g., dimethylformamide or N-methylpyrrolidinone, at temperatures of 0° C. to 100° C., preferably between 30° C. and 60° C. Next, the intermediate of formula VIII can be transformed into an intermediate of formula IX by reaction with an amine $H_2NR^4$ in an appropriate polar solvent, e.g., tetrahydrofuran. The resulting mixture of regio-isomers can be separated by chromatography or, alternatively, the mixture can be used in the next step and the resulting products separated at this stage. In the next step, the intermediate of formula IX is cyclized to the intermediate of formula II by means of a Heck reaction. For example, the intermediate of formula IX can be reacted with sub-stoichiometric or stoichiometric amounts of a suitable transition metal containing compound, e.g., palladium (II) acetate, optionally in the presence of a suitable phosphine ligand, for example triphenyl phosphine, furthermore in the presence of a suitable base, such as a trialkyl amine, e.g., triethyl amine, and in the presence of a suitable reducing agent, e.g., sodium formate. The reaction can take place in an appropriate polar solvent, e.g., dimethylformamide, N-methylpyrrolidinone, or methanol, optionally in the presence of a suitable tetra-alkyl ammonium salt, e.g., tetrabutylammonium chloride, at elevated temperatures of 40° C. to 100° C., preferably 70° C. to 90° C.

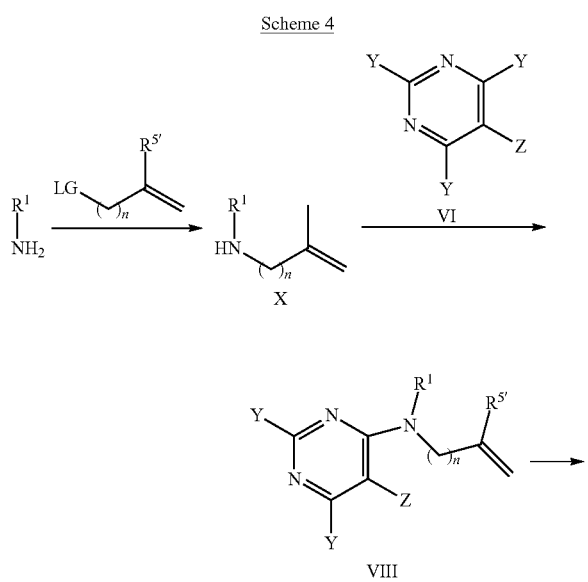

Scheme 4

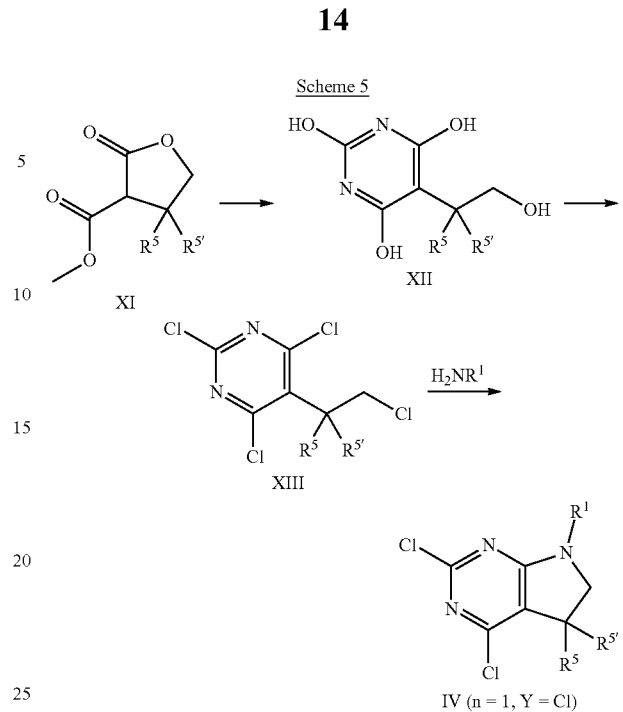

Scheme 5

Alternatively, as depicted in Scheme 4, an intermediate of formula VIII, wherein Y is each individually selected from halogen, preferably chlorine, and Z is selected from halogen, preferably bromine, n is 1 or 2, and R', $R^{5'}$ are as defined above with the exception $R^{5'}$ is not hydrogen, can be synthesized by reaction of amines of formula $H_2NR^1$, wherein $R^1$ is as defined above, with an appropriate alkylating agent LG-[$CH_2$]$_n$C($R^{5'}$)=$CH_2$, wherein n is for 2, preferably 1, and the leaving group LG is halogen or sulfonate OSO$_2$R', wherein R' is lower alkyl, optionally substituted by 1-7 fluorine, or phenyl, optionally substituted by 1-2 halogen, nitro or lower alkyl, e.g., bromine, methylsulfonate, trifluoromethylsulfonate or tolylsulfonate, preferably bromine, and $R^{5'}$ is as defined above, with the exception $R^{5'}$ is not hydrogen, in the presence of a suitable base, e.g., alkali carbonate, such as potassium carbonate, or sodium hydride, in an appropriate polar solvent, e.g., dimethylformamide or N-methylpyrrolidinone, at temperatures between 20° C. and 120° C., preferably between 70° C. and 90° C. Next, the resulting intermediate of formula X can be reacted with a building block of formula VI, wherein Y, Z are as defined above, in the presence of a non-nucleophilic base, such as sodium acetate, in a suitable solvent, e.g., tetrahydrofuran, acetonitrile, water, or in a mixture thereof.

An intermediate of formula IV, wherein Y is chlorine, n is 1, $R^1$ is as defined above, and $R^5$, $R^{5'}$ are as defined above, preferably hydrogen, can be synthesized according to the sequence depicted in Scheme 5. A compound of formula XI, that is either commercially available or can be accessed as described, e.g., in patent EP2050749 (2009), can be reacted with urea in the presence of at least 1 equivalent, preferably, 2-3 equivalents of a suitable base, such as alkali alkoxide, e.g., sodium ethoxide, in an appropriate polar protic or aprotic solvent, e.g., ethanol, at elevated temperatures of 30° C. to 120° C., preferably 60° C. to 80° C. The crude product of formula XII, that can be isolated as sodium salt, can thereafter be reacted with a chlorinating agent, such as phosphorus oxychloride, phosphorus pentachloride, or thionyl chloride, optionally in the presence of stoichiometric amounts of N,N-dimethylaniline, at temperatures between 60° C. and 110° C., preferably between 90° C. and 100° C. The resulting intermediate of formula XIII can then be converted into an intermediate of formula IV (n=1, Y=Cl) by reaction with a suitable amine $H_2NR^1$, wherein $R^1$ is as defined above, in the presence of a suitable base, such as trialkyl amine, e.g., diisopropylethyl amine or triethyl amine, in an appropriate polar, aprotic solvent, such as acetonitrile, at temperatures of 30° C. to 70° C., preferably 40° C. to 60° C.

Alternatively, a more general access to intermediates of formula IV) is outlined in Scheme 6.

Scheme 6

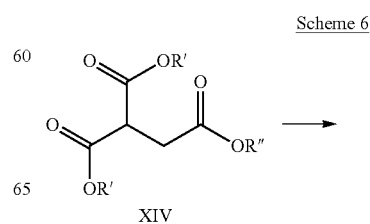

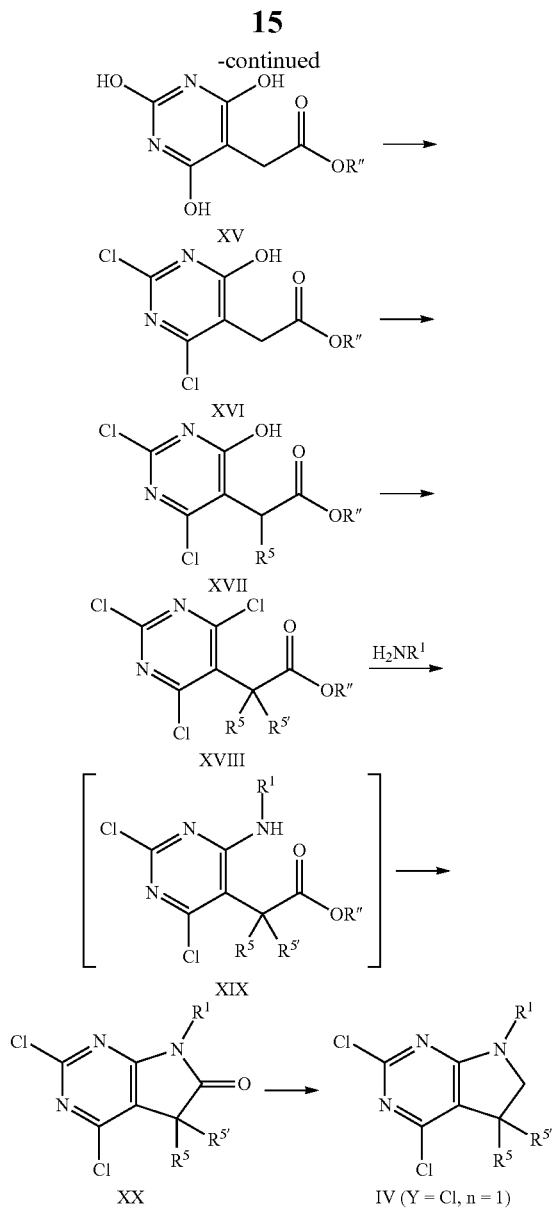

propylamide (LDA), under anhydrous conditions in a suitable solvent, e.g., tetrahydrofuran, and in the presence of ca. 1 equivalent of the appropriate alkylating agent $R^5$—X, wherein $R^5$ is as defined above but not hydrogen, X is halogen or $OSO_2R'$, wherein R' is lower alkyl, optionally optionally substituted by 1-7 fluorine, or phenyl, optionally substituted by 1-2 halogen, nitro or lower alkyl, e.g., bromine, methylsulfonate, trifluoromethylsulfonate or tolylsulfonate, preferably bromine, or iodine. The reaction is carried out at low temperatures of −80° C. to room temperature. Optionally, this alkylation step can be repeated using similar conditions and an alkylation agent $R^5$—X, wherein $R^{5'}$ is as defined above but not hydrogen, X is halogen or $OSO_2R'$, wherein R' is lower alkyl, optionally substituted by 1-7 fluorine, or phenyl, optionally substituted by 1-2 halogen, nitro or lower alkyl, e.g., bromine, iodine methylsulfonate, trifluoromethylsulfonate or tolylsulfonate, preferably bromine, or iodine. In case $R^{5'}$ is hydrogen, intermediate XVIII is identical with intermediate XVII. Thereafter, the intermediate of formula XVIII can be transformed into the intermediate of formula XX by reaction with amine $H_2NR^1$, wherein $R^1$ is as defined above, in the presence of a suitable base, such as trialkyl amine, e.g., diisopropylethyl amine, in a suitable polar solvent, e.g., tetrahydrofuran, at elevated temperatures of 30° C. to 100° C., preferably 50° C. to 80° C. The reaction takes place via intermediate of formula XIX, that cannot be isolated but cyclizes immediately under some reaction conditions. In some cases, the intermediate of formula XIX can be isolated. In these cases, the cyclization to the intermediate of formula XX can be achieved by treatment with an appropriate strong non nucleophilic base, such as alkali bis(trialkylsilyl)amide or alkali diisopropylamide, e.g., lithium bis(trimethylsilyl)amide, in a suitable polar aprotic solvent, e.g., tetrahydrofuran, under anhydrous conditions. The resulting oxindole (intermediate of formula XX) can then be reduced to give the desired intermediate of formula IV (Y=Cl, n=1) by reaction with an appropriate reducing agent, such as a borane, e.g., borane tetrahydrofuran complex, in a suitable polar, aprotic solvent, e.g., tetrahydrofuran, under anhydrous conditions, and at temperatures between 0° C. and 100° C. Preferably, the addition of the borane is done at lower temperatures, whereas the reaction is best carried out at higher temperatures.

An intermediate of formula XIV, wherein R', R" are selected from lower alkyl, preferably methyl or ethyl, that is either commercially available or can be synthesized using methods known in the art, e.g., as described in *Chinese Chemical Letters* 2015, 26, pages 619-622, can be condensed with urea in the presence of a suitable base, such as alkali alkoxide, e.g., sodium ethoxide, in an appropriate polar protic or aprotic solvent, e.g., ethanol. Next, the intermediate of formula XV can be converted into the trichloropyrimidine of formula XVI under standard chlorination conditions known in the art, for example by treatment with phosphorus oxychloride, phosphorus pentachloride, or thionyl chloride e.g., by treatment with phosphorus oxychloride, in the presence of a suitable base, e.g., a trialkyl amine, such as diisopropylethyl amine, optionally in the presence of an appropriate solvent, e.g., toluene, at elevated temperatures of 60° C. to 130° C., preferably 80° C. to 110° C. The resulting intermediate of formula XVI can thereafter be alkylated using a strong non nucleophilic base, such as alkali hexamethyldisilazide or alkali diisopropylamide, such as lithium hexamethyldisilazide (LHMDS) or lithium diiso- Scheme 7

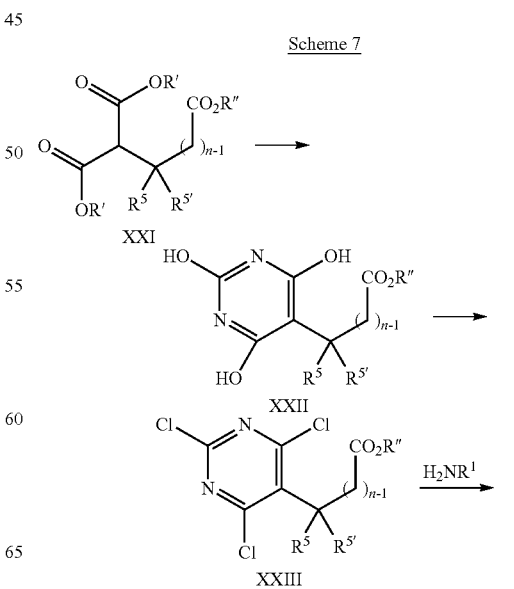

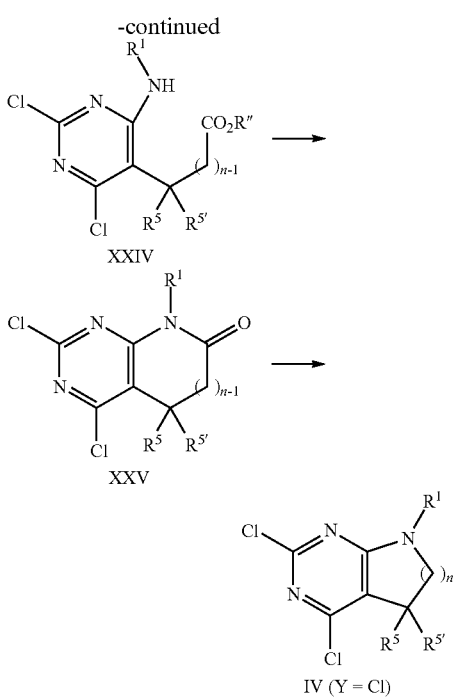

Alternatively, a more general route to intermediates of formula IV (Y=Cl) is depicted in Scheme 7. In analogy to the sequence described in Scheme 6, an intermediate of formula XXI, that is either commercially available or can be synthesized by methods known in the art, can be transformed into an intermediate of formula IV (Y=Cl) via the same sequence of urea condensation, chlorination, amine substitution, cyclisation and reduction, that is described above and using similar methods, respectively, or other methods known in the art.

In case of $R^5$ is not the same as $R^{5'}$, a pair of enantiomers exists for all compounds that contain $R^5$ and $R^{5'}$. The two enantiomers can be separated either as final compounds of formula I or at the stage of an intermediate of formulas II to XXV, preferably an advanced intermediate, e.g., an intermediate of formula II or IV, by means known in the art, e.g., by chromatography on a stationary phase that consists of chiral material (preparative chiral chromatography).

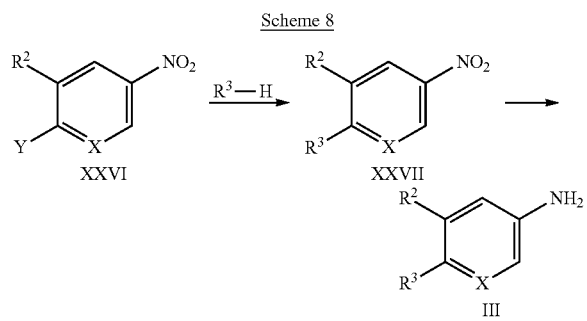

Scheme 8

Intermediates of formula III, wherein X and $R^2$ and $R^3$ are as defined above, are either commercially available or can be synthesized by methods known in the art, e.g., as described in WO2015/109109, WO2015/066687, WO2015/153709, or WO2011/086098. Alternatively, they can be accessed according to the general route depicted in Scheme 8. A compound of formula XXVI, wherein X and $R^2$ are as defined above, and Y is selected from halogen, preferably fluorine or chlorine, can be reacted with triazoles or imidazoles of formula $R^3$—H in the presence of a suitable base, such as an alkali carbonate, e.g., potassium carbonate, in an appropriate polar solvent, such as dimethylsulfoxide, dimethylformamide, or N-methylpyrrolidinone, at temperatures of 20° C. to 100° C., preferably 40° C. to 60° C. Next, the compound of formula XXVII can be reduced to give amines of formula III using reduction methods known in the art. As example, they can be treated with iron powder and acetic acid in a suitable polar, protic solvent, e.g., ethanol. Alternatively, this transformation can be achieved by stirring the compound of formula XXVII under a hydrogen atmosphere in the presence of a suitable transition metal containing catalyst, e.g., palladium on charcoal, in a suitable polar protic or aprotic solvent, such as ethanol or methanol.

The halides of formula XXVI are either commercially available, known in the literature so they can be prepared by methods known in the art.

The compounds were investigated in accordance with the test given hereinafter.

Description of γ-Secretase Assay

Cellular γ-Secretase Assay

Human neuroglioma $H_4$ cells overexpressing human APP695 with the Swedish double mutation (K595N/M596L) were plated at 30,000 cells/well/100 μl in 96-well plates in IMDM media containing 10% FCS, 0.2 mg/l Hygromycin B and incubated at 37° C., 5% $CO_2$.

3-4 hr post plating, compounds are a diluted in media and 50 μl is added as 1.5-fold concentrate to achieve the final concentration. Compound incubation is performed for 24 hr. Final doses typically range from 4 μM down to 0.0013 μM in half-log steps resulting in an eight point dose response curve. Appropriate controls using vehicle only and reference compound were applied to this assay. The final concentration of $Me_2SO$ was 0.4%.

After incubation at 37° C., 5% $CO_2$, the supernatant was subjected to quantification of secreted Aβ42 by the means of an AlphaLisa assay kit (Human Amyloid beta 1-42 Kit: Cat # AL203C, Perkin Elmer). 20 μl of the cell culture supernatant was transferred to an assay plate. Then 10 μl of a mixture of the AlphaLisa coupled capture antibody and the biotinylated detection antibody was added and incubated for 3 hours at room temperature while softly shaking the assay plate. After a further addition of 20 μl of the Donor beads the assay plate was incubated for 30 min at room temperature and constant shaking without exposure to direct light. The assay plate was then read on a Paradigm AlphaLisa Reader using the build-in program with excitation at 680 nm and emission at 570 nm. The measured signals were then used to calculate $IC_{50}$ values for inhibition of Aβ42 secretion by nonlinear regression fit analysis using XLfit 5.3 software (IDBS).

The list below contains data for all compounds for the inhibition of Aβ42 secretion (nM):

| Example No. | $EC_{50}$ Aβ42 (nM) | Example No. | $EC_{50}$ Aβ42 (nM) |
|---|---|---|---|
| 1 | 5 | 2 | 8 |
| 3 | 16 | 4 | 7 |
| 5 | 22 | 6 | 9 |

-continued

| Example No. | EC$_{50}$ Aβ42 (nM) | Example No. | EC$_{50}$ Aβ42 (nM) |
|---|---|---|---|
| 7 | 5 | 8 | 5 |
| 9 | 26 | 10 | 51 |
| 11 | 33 | 12 | 13 |
| 13 | 23 | 14 | 10 |
| 15 | 8 | 16 | 30 |
| 17 | 19 | 18 | 14 |
| 19 | 8 | 20 | 8 |
| 21 | 72 | 22 | 30 |
| 23 | 8 | 24 | 22 |
| 25 | 8 | 26 | 6 |
| 27 | 30 | 28 | 8 |
| 29 | 6 | 30 | 11 |
| 31 | 15 | 32 | 10 |
| 33 | 6 | 34 | 8 |
| 35 | 13 | 36 | 14 |
| 37 | 8 | 38 | 6 |
| 39 | 6 | 40 | 6 |
| 41 | 9 | 42 | 8 |
| 43 | 5 | 44 | 5 |
| 45 | 4 | 46p | 5 |
| 46q | 7 | 47 | 55 |

The compounds of formula I and the pharmaceutically acceptable salts of the compounds of formula I can be used as medicaments, e.g., in the form of pharmaceutical preparations. The pharmaceutical preparations can be administered orally, e.g., in the form of tablets, coated tablets, dragées, hard and soft gelatine capsules, solutions, emulsions or suspensions. The administration can, however, also be effected rectally, e.g., in the form of suppositories, parenterally, e.g., in the form of injection solutions. The administration can also be effected topically, e.g., transdermal administration, or in form of eye drops or ear drops.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | | |
|---|---|---|---|---|---|
| | | mg/tablet | | | |
| Item | Ingredients | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | | |
|---|---|---|---|---|---|
| | | mg/capsule | | | |
| Item | Ingredients | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

Experimental Part

The following examples are provided for illustration of the invention. They should not be considered as limiting the scope of the invention, but merely as being representative thereof.

Analytical Methods

HPLC (method LCMS_fastgradient)

Column: Agilent Zorbax Eclipse Plus $C_{18}$, Rapid Resolution HT, 2.1×30 mm, 1.8 μm, Part. no. 959731-902

Solvent A: Water 0.01% Formic Acid; Solvent B: acetonitrile (MeCN)

Gradients:

| Time [min] | Flow Rate [ml/min] | % A | % B |
| --- | --- | --- | --- |
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 |

Abbreviations

The following abbreviations were used in the experimental part:
THF=tetrahydrofurane;
MTBE=methyl-tert-butylether;
DMF=dimethylformamide;
TLC=thin layer chromatography;
RT=room temperature, 20-25° C.

Intermediates

Intermediate 5

2-Chloro-7-(4-fluorophenyl)-N,5,5-trimethyl-6,7-dihydro-5H-pyrrolo[2,3-d]pyrimidin-4-amine

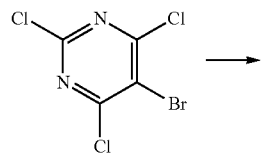
Int-1

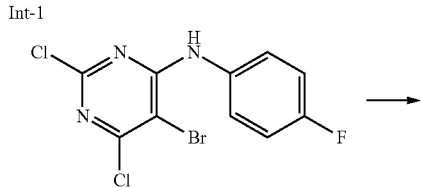
Int-2

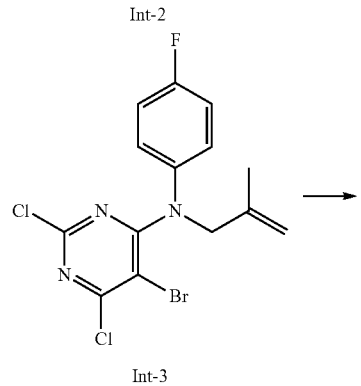
Int-3

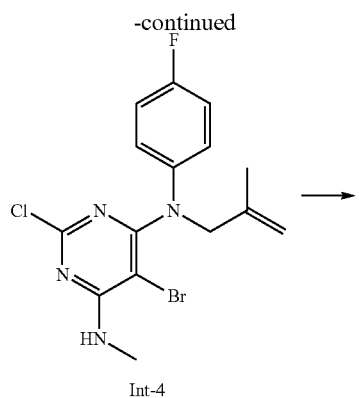
Int-4

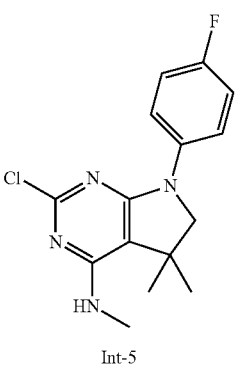
Int-5

Step 1: 5-Bromo-2,6-dichloro-N-(4-fluorophenyl)pyrimidin-4-amine (Int-2)

5-Bromo-2,4,6-trichloropyrimidine (1.880 g, 6.81 mmol) was dissolved in THF (11 mL) and water (5 mL), and sodium acetate (1.68 g, 20.4 mmol), followed by 4-fluoroaniline (787 mg, 0.68 mL, 6.87 mmol) were added. The mixture was stirred at room temperature for 18 h. After that, a saturated aqueous solution of sodium hydrogencarbonate (15 mL) was added and the resulting mixture was extracted with ethyl acetate (2×150 mL). The combined organic layers were dried (sodium sulfate) and concentrated in vacuo. The crude was purified by column chromatography (silica gel, 40 g, eluting with ethyl acetate/n-heptane, gradient 0:100 to 10:90) to afford, after drying in vacuo (40° C., 5 mbar), the title compound as a light brown solid (2.07 g, 90%). HPLC (method LCMS_fastgradient) $t_R$=1.36 min. $^1$H NMR (CDCl$_3$, 300 MHz): δ 7.12 (dd, J=8.3, 9.1 Hz, 2H), 7.43 (br s, 1H), 7.52 (dd, J=4.6, 8.9 Hz, 2H). MS (ES+) m/z 335.9, 337.9, 339.9 [M+H, Br and 2 Cl isotopes].

Step 2: 5-Bromo-2,6-dichloro-N-(4-fluorophenyl)-N-(2-methylallyl)pyrimidin-4-amine (Int-3)

5-Bromo-2,6-dichloro-N-(4-fluorophenyl)pyrimidin-4-amine (Int-2, 1.45 g, 4.3 mmol) was dissolved in dimethylformamide (14 mL) and sodium hydride (60% dispersion in mineral oil, 239 mg, 5.98 mmol) was added carefully (gas evolution). The mixture was stirred at room temperature for 1 h. Then, 3-bromo-2-methylprop-1-ene (964 mg, 6.93 mmol) was added and the resulting mixture was stirred for 18 h at room temperature. After that, water (20 mL) was added, the mixture was extracted with methyltertbutyl ether (2×150 mL), the organic phases were washed with water (3×20 mL) and brine (20 mL), combined, dried (sodium sulfate), and concentrated in vacuo. The crude product was purified by column chromatography (silica gel, 120 g, eluting with ethyl acetate/n-heptane, gradient 0:100 to 5:95) to give the title compound as yellow oil (1.294 g, 69%). HPLC (method LCMS_fastgradient) $t_R$=1.63 min. $^1$H NMR (CDCl$_3$, 300 MHz): δ 1.80 (s, 3H), 4.58 (s, 2H), 4.85-4.93 (m, 2H), 7.00-7.09 (m, 4H). MS (ES+) m/z 390.0, 392.0, 394.0 [M+H, Br and 2 Cl isotopes].

Step 3: 5-Bromo-2-chloro-N4-(4-fluorophenyl)-N6-methyl-N4-(2-methylallyl)pyrimidine-4,6-diamine (Int-4)

5-Bromo-2,6-dichloro-N-(4-fluorophenyl)-N-(2-methylallyl)pyrimidin-4-amine (Int-3, 0.830 g, 1.91 mmol) was dissolved in tetrahydrofuran (1.9 mL) and a solution of methylamine in tetrahydrofuran (2.0 M, 3.8 mL, 7.6 mmol) was added dropwise. The mixture was stirred at room temperature for 18 h. After that, water (10 mL) was added, the mixture was extracted with ethyl acetate (2×90 mL), the organic layers were washed with brine (50 mL), combined, dried (sodium sulfate) and concentrated in vacuo. The crude product was purified by column chromatography (silica gel, 40 g, eluting with ethyl acetate/n-heptane, gradient 0:100 to 5:95) to afford the title compound as an off-white solid (396 mg, 51%). HPLC (method LCMS_fastgradient) $t_R$=1.55 min. $^1$H NMR (CDCl$_3$, 300 MHz): δ 1.78 (s, 3H), 3.05 (d, J=5.0 Hz, 3H), 4.52 (s, 2H), 4.84-4.89 (m, 1H), 4.91-4.95 (m, 1H), 5.48-5.56 (m, 1H), 6.94-7.00 (m, 4H). MS (ES+) m/z 385.0, 387.0, 389.0 [M+H, Br and Cl isotopes].

Step 4: 2-Chloro-7-(4-fluorophenyl)-N,5,5-trimethyl-6,7-dihydro-5H-pyrrolo[2,3-d]pyrimidin-4-amine (Int-5)

5-Bromo-2-chloro-N4-(4-fluorophenyl)-N6-methyl-N4-(2-methylallyl)pyrimidine-4,6-diamine (Int-4, 390 mg, 1.01 mmol), sodium formate (73 mg, 1.07 mmol), tetrabutylammonium chloride (287 mg, 1.03 mmol) and palladium (II) acetate (52 mg, 0.232 mmol) were charged under argon in a 25 mL round bottomed flask. Dimethylformamide (3.2 mL), followed by triethylamine (261 mg, 2.58 mmol) were added and the flask was evacuated carefully and backfilled with argon. The resulting mixture was stirred at 80° C. for 18 h. After cooling, water (5 mL) was added, the mixture was extracted with methyltertbutyl ether (2×60 mL), the organic layers were washed with water (3×10 mL) and brine (1×10 mL), combined, dried (sodium sulfate) and concentrated in vacuo. The crude product was purified by column chromatography (silica gel, 25 g, eluting with ethyl acetate/n-heptane, gradient 0:100 to 20:80) to afford the title compound as a yellow solid (259 mg, 83%). HPLC (method LCMS_fastgradient) $t_R$=1.41 min. $^1$H NMR (CDCl$_3$, 300 MHz): δ 1.42 (s, 6H), 3.07 (d, J=4.8 Hz, 3H), 3.71 (s, 2H), 4.25-4.34 (m, 1H), 7.06 (dd, J=8.5, 9.3 Hz, 2H), 7.58 (dd, J=4.6, 9.3 Hz, 2H). MS (ES+) m/z 307.1, 309.1 [M+H, Cl isotopes].

Intermediate 9

2-Chloro-7-(3,4-difluorophenyl)-N,5,5-trimethyl-6,7-dihydro-5H-pyrrolo[2,3-d]pyrimidin-4-amine

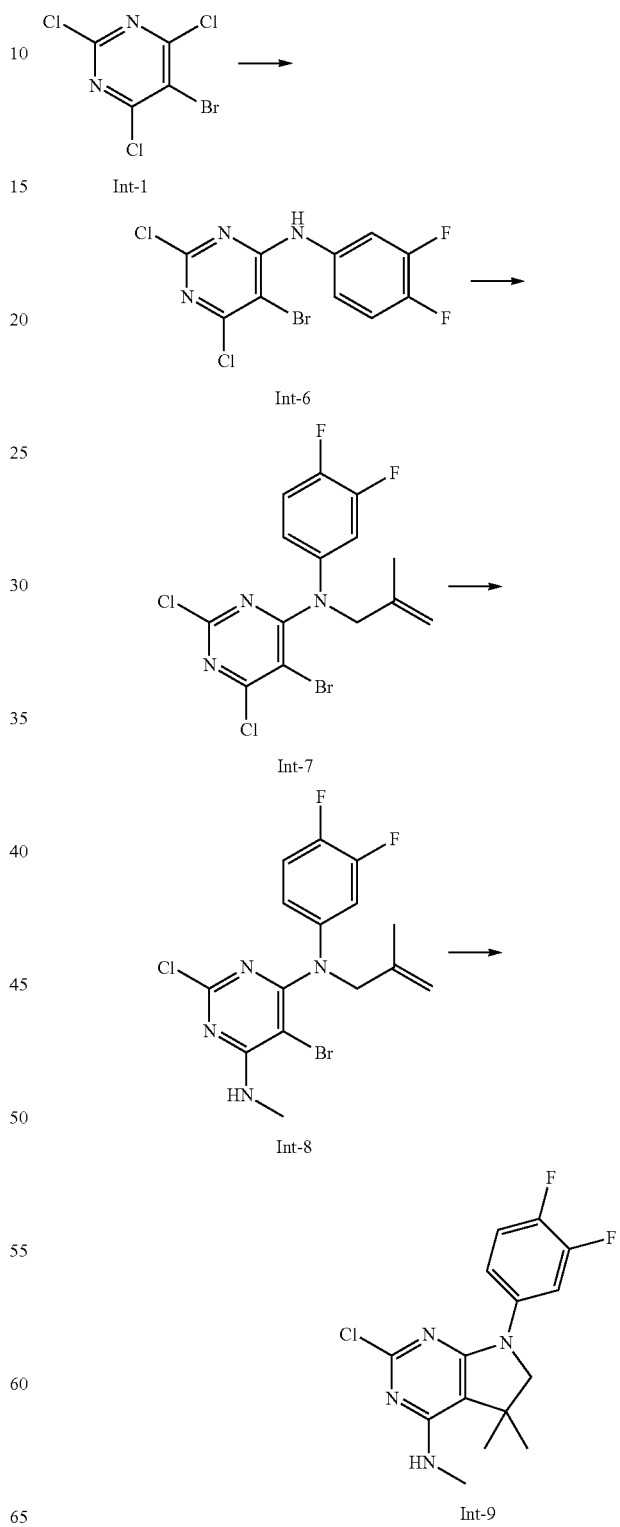

Step 1: 5-Bromo-2,6-dichloro-N-(3,4-difluorophenyl)pyrimidin-4-amine (Int-6)

5-Bromo-2,4,6-trichloropyrimidine (3.00 g, 10.9 mmol) was dissolved in THF (18 mL) and water (9 mL), and sodium acetate (2.67 g, 32.6 mmol), followed by 3,4-difluoroaniline (1.43 g, 1.10 mL, 11.1 mmol) were added. The mixture was stirred at room temperature for 18 h. After that, a saturated aqueous solution of sodium hydrogencarbonate (30 mL) was added and the resulting mixture was extracted with ethyl acetate (2×150 mL). The combined organic layers were dried (sodium sulfate) and concentrated in vacuo. The crude was purified by column chromatography (silica gel, 120 g, eluting with ethyl acetate/n-heptane, gradient 0:100 to 10:90) to afford, after drying in vacuo (40° C., 5 mbar), the title compound as a light yellow solid (3.32 g, 86%). HPLC (method LCMS_fastgradient) $t_R$=1.37 min. $^1$H NMR (CDCl$_3$, 300 MHz): δ 7.17-7.24 (m, 2H), 7.43 (br s, 1H), 7.59-7.68 (m, 1H). MS (ES+) m/z 353.9, 355.9, 357.8 [M+H, Br and 2 Cl isotopes].

Step 2: 5-Bromo-2,6-dichloro-N-(3,4-difluorophenyl)-N-(2-methylallyl)pyrimidin-4-amine (Int-7)

5-Bromo-2,6-dichloro-N-(3,4-difluorophenyl)pyrimidin-4-amine (Int-6, 3.32 g, 9.35 mmol) was dissolved in dimethylformamide (30 mL) and sodium hydride (60% dispersion in mineral oil, 520 mg, 13 mmol) was added carefully (gas evolution). The mixture was stirred at room temperature for 1 h. Then, 3-bromo-2-methylprop-1-ene (2.14 mg, 15.4 mmol) was added and the resulting mixture was stirred for 4.5 h at room temperature, followed by 16 h at 60° C. After that, water (20 mL) was added, the mixture was extracted with methyltertbutyl ether (2×150 mL), the organic phases were washed with water (3×20 mL) and brine (20 mL), combined, dried (sodium sulfate), and concentrated in vacuo. The crude product was purified by column chromatography (silica gel, 120 g, eluting with ethyl acetate/n-heptane, gradient 0:100 to 5:95) to give the title compound as a light yellow oil (3.54 g, 83%). HPLC (method LCMS_fastgradient) $t_R$=1.59 min. $^1$H NMR (CDCl$_3$, 300 MHz): δ 1.79 (d, J=0.6 Hz, 3H), 4.59 (s, 2H), 4.86-4.89 (m, 1H), 4.91-4.95 (m, 1H), 6.76-6.83 (m, 1H), 6.97 (ddd, J=2.7, 6.8, 11.0 Hz, 1H), 7.08-7.19 (m, 1H). MS (ES+) m/z 408.0, 410.0, 411.9 [M+H, Br and 2 Cl isotopes].

Step 3: 5-Bromo-2-chloro-N4-(3,4-difluorophenyl)-N6-methyl-N4-(2-methylallyl)-pyrimidine-4,6-diamine (Int-8)

5-Bromo-2,6-dichloro-N-(3,4-difluorophenyl)-N-(2-methylallyl)pyrimidin-4-amine (Int-7, 3.53 g, 7.77 mmol) was dissolved in tetrahydrofuran (15 mL) and a solution of methylamine in tetrahydrofuran (2.0 M, 15.0 mL, 30.0 mmol) was added dropwise. The mixture was stirred at room temperature for 18 h. After that, water (20 mL) was added, the mixture was extracted with ethyl acetate (2×120 mL), the organic layers were washed with brine (20 mL), combined, dried (sodium sulfate) and concentrated in vacuo. The crude product was purified by column chromatography (silica gel, 120 g, eluting with ethyl acetate/n-heptane, gradient 0:100 to 5:95) to afford the title compound as an off-white solid (1.52 g, 48%). HPLC (method LCMS_fastgradient) $t_R$=1.56 min. $^1$H NMR (CDCl$_3$, 300 MHz): δ 1.78 (d, J=0.6 Hz, 3H), 3.06 (d, J=4.8 Hz, 3H), 4.52 (s, 2H), 4.87-4.90 (m, 1H), 4.93-4.96 (m, 1H), 5.52-5.63 (m, 1H), 6.66-6.73 (m, 1H), 6.84 (ddd, J=2.6, 6.8, 11.7 Hz, 1H), 6.98-7.09 (m, 1H). MS (ES+) m/z 403.1, 405.1, 407.0 [M+H, Br and Cl isotopes].

Step 4: 2-Chloro-7-(3,4-difluorophenyl)-N,5,5-trimethyl-6,7-dihydro-5H-pyrrolo[2,3-d]pyrimidin-4-amine (Int-9)

5-Bromo-2-chloro-N4-(3,4-difluorophenyl)-N6-methyl-N4-(2-methylallyl)pyrimidine-4,6-diamine (Int-8, 1.50 g, 3.72 mmol), sodium formate (268 mg, 3.94 mmol), tetrabutylammonium chloride (1.05 g, 3.79 mmol) and palladium (II) acetate (191 mg, 851 µmol) were charged under argon in a 50 mL round bottomed flask. Dimethylformamide (11 mL), followed by triethylamine (944 mg, 9.33 mmol) were added and the flask was evacuated carefully and backfilled with argon. The resulting mixture was stirred at 80° C. for 18 h. After cooling, water (15 mL) was added, the mixture was extracted with methyltertbutyl ether (2×120 mL), the organic layers were washed with water (3×15 mL) and brine (1×15 mL), combined, dried (sodium sulfate) and concentrated in vacuo. The crude product was purified by column chromatography (silica gel, 80 g, eluting with ethyl acetate/n-heptane, gradient 0:100 to 30:70) to afford the title compound as a light yellow solid (839 mg, 69%). HPLC (method LCMS_fastgradient) $t_R$=1.45 min. $^1$H NMR (CDCl$_3$, 300 MHz): δ 1.42 (s, 6H), 3.08 (d, J=4.8 Hz, 3H), 3.69 (s, 2H), 4.28-4.39 (m, 1H), 7.07-7.18 (m, 1H), 7.23-7.30 (m, 1H), 7.67 (ddd, J=2.7, 7.0, 13.1 Hz, 1H). MS (ES+) m/z 325.0, 327.0 [M+H, Cl isotopes].

Intermediate 13

2-Chloro-7-(2,4-difluorophenyl)-N,5,5-trimethyl-6,7-dihydro-5H-pyrrolo[2,3-d]pyrimidin-4-amine

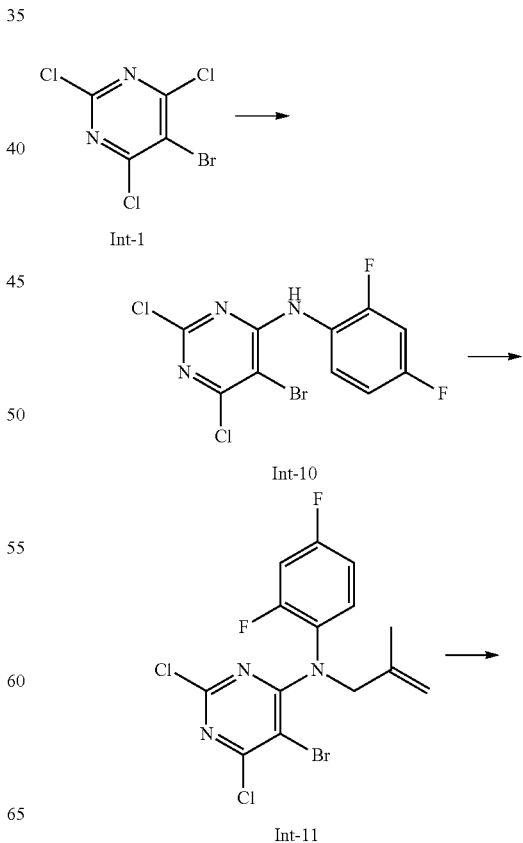

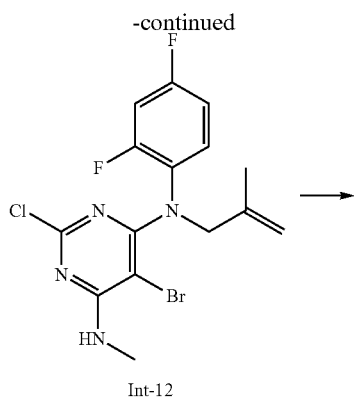

Int-12

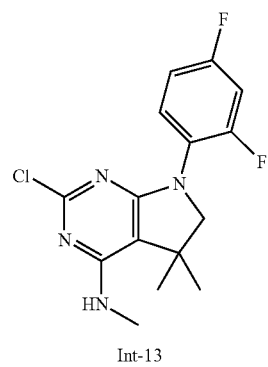

Int-13

Step 1: 5-Bromo-2,6-dichloro-N-(2,4-difluorophenyl)pyrimidin-4-amine (Int-10)

5-Bromo-2,4,6-trichloropyrimidine (2.50 g, 9.05 mmol) was dissolved in THF (16 mL) and water (8 mL), and sodium acetate (2.23 g, 27.2 mmol), followed by 2,4-difluoroaniline (1.18 g, 0.92 mL, 9.14 mmol) were added. The mixture was stirred at room temperature for 18 h. After that, a saturated aqueous solution of sodium hydrogencarbonate (30 mL) was added and the resulting mixture was extracted with ethyl acetate (2×150 mL). The combined organic layers were dried (sodium sulfate) and concentrated in vacuo. The crude was purified by column chromatography (silica gel, 120 g, eluting with ethyl acetate/n-heptane, gradient 0:100 to 5:95) to yield, after drying in vacuo (40° C., 5 mbar), the title compound as an off-white solid (2.22 g, 69%). HPLC (method LCMS_fastgradient) $t_R$=1.39 min. $^1$H NMR (CDCl$_3$, 300 MHz): δ 6.91-7.03 (m, 2H), 7.56 (br s, 1H), 8.16 (ddd, J=5.8, 9.7, 9.7 Hz, 1H). MS (ES+) m/z 353.9, 355.9, 357.9 [M+H, Br and 2 Cl isotopes].

Step 2: 5-Bromo-2,6-dichloro-N-(2,4-difluorophenyl)-N-(2-methylallyl)pyrimidin-4-amine (Int-11)

5-Bromo-2,6-dichloro-N-(2,4-difluorophenyl)pyrimidin-4-amine (Int-10, 2.22 g, 6.25 mmol) was dissolved in dimethylformamide (20 mL) and sodium hydride (60% dispersion in mineral oil, 348 mg, 8.7 mmol) was added carefully (gas evolution). The mixture was stirred at room temperature for 1.5 h. Then, 3-bromo-2-methylprop-1-ene (2.14 mg, 15.4 mmol) was added and the resulting mixture was stirred for 16 h at 40° C. After that, water (20 mL) was added, the mixture was extracted with methyltertbutyl ether (2×100 mL), the organic phases were washed with water (3×20 mL) and brine (20 mL), combined, dried (sodium sulfate), and concentrated in vacuo. The crude product was purified by column chromatography (silica gel, 120 g, eluting with ethyl acetate/n-heptane, gradient 0:100 to 5:95) to afford the title compound as a yellow oil (1.55 g, 61%). HPLC (method LCMS_fastgradient) $t_R$=1.65 min. $^1$H NMR (CDCl$_3$, 300 MHz): δ 1.79 (s, 3H), 4.56 (s, 2H), 4.80-4.83 (m, 1H), 4.87-4.90 (m, 1H), 6.82-6.95 (m, 2H), 7.14-7.23 (m, 1H). MS (ES+) m/z 408.0, 410.0, 412.0 [M+H, Br and 2 Cl isotopes].

Step 3: 5-Bromo-2-chloro-N4-(2,4-difluorophenyl)-N6-methyl-N4-(2-methylallyl)-pyrimidine-4,6-diamine (Int-12)

5-Bromo-2,6-dichloro-N-(2,4-difluorophenyl)-N-(2-methylallyl)pyrimidin-4-amine (Int-11, 1.54 g, 3.76 mmol) was dissolved in tetrahydrofuran (7.5 mL) and a solution of methylamine in tetrahydrofuran (2.0 M, 6.5 mL, 13.0 mmol) was added drop-wise. The mixture was stirred at room temperature for 45 min. After that, water (10 mL) was added, the mixture was extracted with ethyl acetate (2×90 mL), the organic layers were washed with brine (10 mL), combined, dried (sodium sulfate) and concentrated in vacuo. The crude product was purified by column chromatography (silica gel, 80 g, eluting with ethyl acetate/n-heptane, gradient 0:100 to 10:90) to obtain the title compound as a colorless oil (717 mg, 47%). HPLC (method LCMS_fastgradient) $t_R$=1.54 min. $^1$H NMR (CDCl$_3$, 300 MHz): δ 1.78 (s, 3H), 3.03 (d, J=4.8 Hz, 3H), 4.47 (s, 2H), 4.82-4.86 (m, 2H), 5.43-5.53 (m, 1H), 6.77-6.87 (m, 2H), 7.07-7.17 (m, 1H). MS (ES+) m/z 403.0, 404.8, 406.9 [M+H, Br and Cl isotopes].

Step 4: 2-Chloro-7-(2,4-difluorophenyl)-N,5,5-trimethyl-6,7-dihydro-5H-pyrrolo[2,3-d]pyrimidin-4-amine (Int-13)

5-Bromo-2-chloro-N4-(2,4-difluorophenyl)-N6-methyl-N4-(2-methyl allyl)pyrimidine-4,6-diamine (Int-12, 710 mg, 1.76 mmol), sodium formate (127 mg, 1.86 mmol), tetrabutylammonium chloride (500 mg, 1.80 mmol) and palladium (II) acetate (90 mg, 401 μmol) were charged under argon in a 25 mL round bottomed flask. Dimethylformamide (5.4 mL), followed by triethylamine (457 mg, 4.52 mmol) were added and the flask was evacuated carefully and backfilled with argon. The resulting mixture was stirred at 80° C. for 18 h. After cooling, water (10 mL) was added, the mixture was extracted with methyltertbutyl ether (2×80 mL), the organic layers were washed with water (3×10 mL) and brine (1×10 mL), combined, dried (sodium sulfate) and concentrated in vacuo. The crude product was purified by column chromatography (silica gel, 25 g, eluting with ethyl acetate/n-heptane, gradient 0:100 to 20:80) to yield the title compound as a light yellow solid (491 mg, 86%). HPLC (method LCMS_fastgradient) $t_R$=1.32 min. $^1$H NMR (CDCl$_3$, 300 MHz): δ 1.41 (s, 6H), 3.07 (d, J=4.8 Hz, 3H), 3.67 (d, J=0.8 Hz, 2H), 4.26-4.37 (m, 1H), 6.83-6.94 (m, 2H), 7.45-7.55 (m, 1H). MS (ES+) m/z 325.0, 327.0 [M+H, Cl isotopes].

Intermediate 17

2-Chloro-7-(3,3-difluorocyclobutyl)-N,5,5-trimethyl-6,7-dihydro-5H-pyrrolo[2,3-d]pyrimidin-4-amine

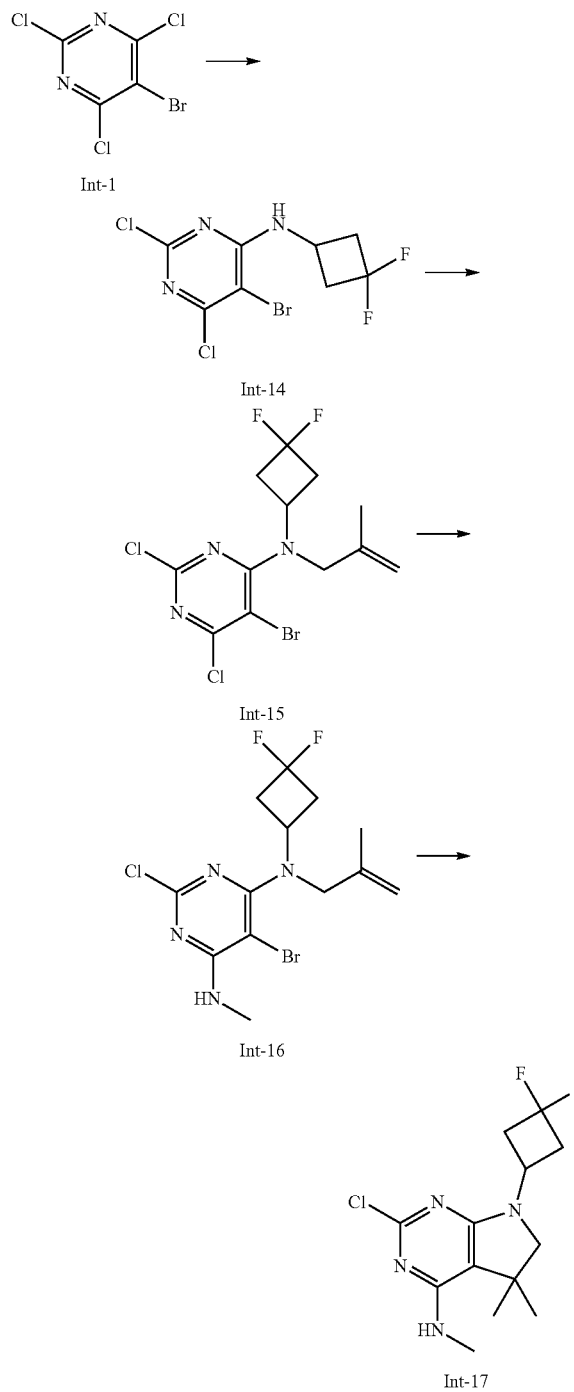

Step 1: 5-Bromo-2,6-dichloro-N-(3,3-difluorocyclobutyl)pyrimidin-4-amine (Int-14)

5-Bromo-2,4,6-trichloropyrimidine (1.28 g, 4.88 mmol) and 3,3-difluorocyclobutanamine hydrochloride (715 mg, 4.98 mmol) were suspended in acetonitrile (6 mL) and N,N-diisopropylethylamine (1.55 g, 2.1 mL, 12 mmol) was added at room temperature. The resulting yellow solution was stirred for 7 h at room temperature. After that, the reaction mixture was concentrated in vacuo and the residue was purified by column chromatography (silica gel, 80 g, eluting with ethyl acetate/n-heptane, gradient 0:100 to 10:90) to yield, after drying in vacuo (40° C., 5 mbar), the title compound as a pale yellow oil (1.188 g, 73%). HPLC (method LCMS_fastgradient) $t_R$=1.31 min. $^1$H NMR (CDCl$_3$, 300 MHz): δ 2.48-2.67 (m, 2H), 3.08-3.25 (m, 2H), 4.39-4.53 (m, 1H), 5.78-5.90 (m, 1H). MS (ES+) m/z 330.0, 332.0, 334.0 [M+H, Br and 2 Cl isotopes].

Step 2: 5-Bromo-2,6-dichloro-N-(3,3-difluorocyclobutyl)-N-(2-methylallyl)pyrimidin-4-amine (Int-15)

5-Bromo-2,6-dichloro-N-(3,3-difluorocyclobutyl)pyrimidin-4-amine (Int-14, 1.18 g, 3.54 mmol) was dissolved in dimethylformamide (12 mL) and sodium hydride (60% dispersion in mineral oil, 198 mg, 4.96 mmol) was added carefully (gas evolution). The mixture was stirred at room temperature for 1 h. Then, 3-bromo-2-methylprop-1-ene (844 mg, 6.06 mmol) was added and the resulting mixture was stirred for 18 h at room temperature. After that, water (15 mL) was added, the mixture was extracted with methyltertbutyl ether (2×100 mL), the organic phases were washed with water (3×15 mL) and brine (15 mL), combined, dried (sodium sulfate), and concentrated in vacuo. The crude product was purified by column chromatography (silica gel, 40 g, eluting with ethyl acetate/n-heptane, gradient 0:100 to 5:95) to give the title compound as colorless oil (965 mg, 70%). HPLC (method LCMS_fastgradient) $t_R$=1.55 min. $^1$H NMR (CDCl$_3$, 300 MHz): δ 1.61 (s, 3H), 2.45-2.67 (m, 2H), 2.89-3.07 (m, 2H), 4.19 (s, 2H), 4.21-4.35 (m, 1H), 4.82-4.86 (m, 1H), 4.94-4.98 (m, 1H). MS (ES+) m/z 385.9, 387.9, 389.8 [M+H, Br and 2 Cl isotopes].

Step 3: 5-Bromo-2-chloro-N4-(3,3-difluorocyclobutyl)-N6-methyl-N4-(2-methylallyl)-pyrimidine-4,6-diamine (Int-16)

5-Bromo-2,6-dichloro-N-(3,3-difluorocyclobutyl)-N-(2-methylallyl)pyrimidin-4-amine (Int-15, 0.960 g, 2.48 mmol) was dissolved in tetrahydrofuran (6 mL) and a solution of methylamine in tetrahydrofuran (2.0 M, 2.0 mL, 4.0 mmol) was added dropwise. The mixture was stirred at room temperature for 1.5 h. After that, water (10 mL) was added, the mixture was extracted with ethyl acetate (2×90 mL), the organic phases were washed with brine (10 mL), combined, dried (sodium sulfate), and concentrated in vacuo. The crude product was purified by column chromatography (silica gel, 40 g, eluting with ethyl acetate/n-heptane, gradient 0:100 to 10:90) to yield the title compound as an off-white solid (311 mg, 33%). HPLC (method LCMS_fastgradient) $t_R$=1.49 min. $^1$H NMR (CDCl$_3$, 300 MHz): δ 1.60 (s, 3H), 2.44-2.55 (m, 2H), 2.85-2.95 (m, 2H), 3.05 (d, J=4.8 Hz, 3H), 4.00 (s, 2H), 4.09-4.17 (m, 1H), 4.85 (br s, 1H), 4.88 (br s, 1H), 5.52-5.57 (m, 1H). MS (ES+) m/z 381.0, 382.9, 384.9 [M+H, Br and Cl isotopes].

Step 4: 2-Chloro-7-(3,3-difluorocyclobutyl)-N,5,5-trimethyl-6,7-dihydro-5H-pyrrolo[2,3-d]pyrimidin-4-amine (Int-17)

5-Bromo-2-chloro-N4-(3,3-difluorocyclobutyl)-N6-methyl-N4-(2-methylallyl)pyrimidine-4,6-diamine (Int-16, 300 mg, 0.786 mmol), sodium formate (57 mg, 0.838 mmol), tetrabutylammonium chloride (223 mg, 0.802 mmol) and palladium (II) acetate (39 mg, 0.174 mmol) were charged under argon in a 25 mL round bottomed flask. Dimethylformamide (2.4 mL), followed by triethylamine (203 mg, 2.01 mmol) were added and the flask was evacuated carefully and backfilled with argon. The resulting mixture was stirred at 80° C. for 18 h. After cooling, water (5 mL) was added, the mixture was extracted with methyl-tertbutyl ether (2×70 mL), the organic phases were washed with water (3×5 mL) and brine (5 mL), combined, dried (sodium sulfate), and concentrated in vacuo. The crude product was purified by column chromatography (silica gel, 25 g, eluting with ethyl acetate/n-heptane, gradient 0:100 to 30:70) to afford the title compound as a yellow solid (204 mg, 86%). HPLC (method LCMS_fastgradient) $t_R$=1.26 min. $^1$H NMR (CDCl$_3$, 300 MHz): δ 1.34 (s, 6H), 2.67-2.95 (m, 4H), 3.02 (d, J=4.8 Hz, 3H), 3.26 (s, 2H), 4.11-4.21 (m, 1H), 4.52-4.67 (m, 1H). MS (ES+) m/z 303.1, 305.0 [M+H, Cl isotopes].

Intermediate 21

2-Chloro-N,5,5-trimethyl-7-(3-(trifluoromethyl)bicyclo[1.1.1]pentan-1-yl)-6,7-dihydro-5H-pyrrolo[2,3-d]pyrimidin-4-amine

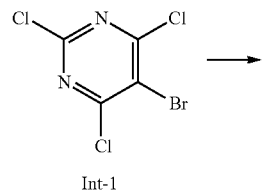

Int-1

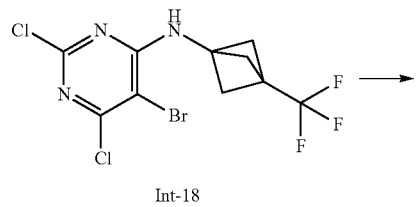

Int-18

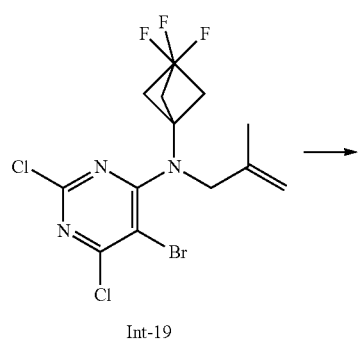

Int-19

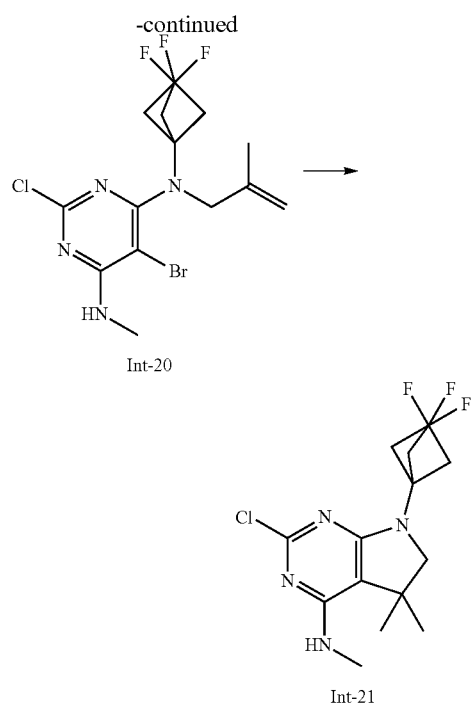

Step 1: 5-Bromo-2,6-dichloro-N-(3-(trifluoromethyl)bicyclo[1.1.1]pentan-1-yl)pyrimidin-4-amine (Int-18)

5-Bromo-2,4,6-trichloropyrimidine (1.30 g, 4.96 mmol) and 3-(trifluoromethyl)-bicyclo[1.1.1]pentan-1-amine hydrochloride (985 mg, 4.99 mmol) were suspended in acetonitrile (6.5 mL) and N,N-diisopropylethylamine (1.55 g, 2.1 mL, 12 mmol) was added at room temperature. The resulting yellow solution was stirred for 7 h at room temperature. After that, the reaction mixture was concentrated in vacuo and the residue was purified by column chromatography (silica gel, 80 g, eluting with ethyl acetate/n-heptane, gradient 0:100 to 10:90) to yield, after drying in vacuo (40° C., 5 mbar), the title compound as an off-white solid (1.487 g, 80%). HPLC (method LCMS_fastgradient) $t_R$=1.50 min. $^1$H NMR (CDCl$_3$, 300 MHz): δ 2.46 (s, 6H), 6.10 (br s, 1H). MS (ES+) m/z 375.9, 377.9, 379.8 [M+H, Br and 2 Cl isotopes].

Step 2: 5-Bromo-2,6-dichloro-N-(2-methylallyl)-N-(3-(trifluoromethyl)bicyclo[1.1.1]pentan-1-yl)pyrimidin-4-amine (Int-19)

5-Bromo-2,6-dichloro-N-(3-(trifluoromethyl)bicyclo[1.1.1]pentan-1-yl)pyrimidin-4-amine (Int-18, 1.48 g, 3.93 mmol) was dissolved in dimethylformamide (13 mL) and sodium hydride (60% dispersion in mineral oil, 220 mg, 5.50 mmol) was added carefully (gas evolution). The mixture was stirred at room temperature for 1.5 h. Then, 3-bromo-2-methylprop-1-ene (937 mg, 6.73 mmol) was added and the resulting mixture was stirred for 5 h at room temperature, followed by 14 h at 40° C. After that, water (15 mL) was added, the mixture was extracted with methyltertbutyl ether (2×100 mL), the organic phases were washed with water (3×15 mL) and brine (15 mL), combined, dried (sodium sulfate), and concentrated in vacuo. The crude product was purified by column chromatography (silica gel, 80 g, eluting with ethyl acetate/n-heptane, gradient 0:100 to 5:95) to yield the title compound as colorless oil (1.372 g, 73%). HPLC (method LCMS_fastgradient) $t_R$=1.77 min. $^1$H NMR (CDCl$_3$, 300 MHz): δ 1.68 (s, 3H), 2.45 (s, 6H), 4.25 (s, 2H), 4.85-4.91 (m, 1H), 4.97-5.02 (m, 1H). MS (ES+) m/z 430.0, 432.0, 434.0 [M+H, Br and 2 Cl isotopes].

Step 3: 5-Bromo-2-chloro-N4-methyl-N6-(2-methylallyl)-N6-(3-(trifluoromethyl)bicyclo-[1.1.1]pentan-1-yl)pyrimidine-4,6-diamine (Int-20)

5-Bromo-2,6-dichloro-N-(2-methylallyl)-N-(3-(trifluoromethyl)bicyclo[1.1.1]pentan-1-yl)pyrimidin-4-amine (Int-19, 1.37 g, 2.86 mmol) was dissolved in tetrahydrofuran (7.0 mL) and a solution of methylamine in tetrahydrofuran (2.0 M, 3.5 mL, 7.0 mmol) was added dropwise. The mixture was stirred at room temperature for 1.5 h. After that, water (10 mL) was added, the mixture was extracted with ethyl acetate (2×90 mL), the organic phases were washed with brine (10 mL), combined, dried (sodium sulfate), and concentrated in vacuo. The crude product was purified by column chromatography (silica gel, 40 g, eluting with ethyl acetate/n-heptane, gradient 0:100 to 10:90) to afford the title compound as a mixture of regioisomers (ratio ca. 2.7:1 by $^1$H nmr) and as an off-white solid (1.179 g, 97%). The isolated mixture was used in the next step without further purification. Major regioisomer (title compound): HPLC (method LCMS_fastgradient) $t_R$=1.69 min. MS (ES+) m/z 425.1, 427.1, 429.0 [M+H, Br and Cl isotopes]. Minor regioisomer (5-bromo-6-chloro-N2-methyl-N4-(2-methylallyl)-N4-(3-(trifluoromethyl)bicyclo[1.1.1]pentan-1-yl)pyrimidine-2,4-diamine): HPLC (method LCMS_fastgradient) $t_R$=1.71 min. MS (ES+) m/z 425.1, 427.1, 429.0 [M+H, Br and Cl isotopes].

Step 4: 2-Chloro-N,5,5-trimethyl-7-(3-(trifluoromethyl)bicyclo[1.1.1]pentan-1-yl)-6,7-dihydro-5H-pyrrolo[2,3-d]pyrimidin-4-amine (Int-21)

5-Bromo-2-chloro-N4-methyl-N6-(2-methylallyl)-N6-(3-(trifluoromethyl)bicyclo[1.1.1]pen-tan-1-yl)pyrimidine-4,6-diamine (Int-20, ca. 2.7:1 mixture of regioisomers, 1.17 g, 2.75 mmol), sodium formate (200 mg, 2.94 mmol), tetrabutylammonium chloride (779 mg, 2.80 mmol) and palladium (II) acetate (136 mg, 0.605 mmol) were charged under argon in a 50 mL round bottomed flask. Dimethylformamide (8.5 mL), followed by triethylamine (726 mg, 7.17 mmol) were added and the flask was evacuated carefully and backfilled with argon. The resulting mixture was stirred at 80° C. for 18 h. After cooling, water (10 mL) was added, the mixture was extracted with methyltertbutyl ether (2×90 mL), the organic phases were washed with water (3×10 mL) and brine (10 mL), combined, dried (sodium sulfate), and concentrated in vacuo. The crude product was purified by column chromatography (silica gel, 40 g, eluting with ethyl acetate/n-heptane, gradient 0:100 to 20:80) to afford the title compound as a yellow solid (584 mg, 61%). HPLC (method LCMS_fastgradient) $t_R$=1.53 min. $^1$H NMR (CDCl$_3$, 300 MHz): δ 1.32 (s, 6H), 2.34 (s, 6H), 3.02 (d, J=4.8 Hz, 3H), 3.17 (s, 2H), 4.11-4.22 (m, 1H). MS (ES+) m/z 347.0, 349.0 [M+H, Cl isotopes].

Intermediate 23

2-((2-Chloro-7-(4-fluorophenyl)-5,5-dimethyl-6,7-dihydro-5H-pyrrolo[2,3-d]pyrimidin-4-yl)amino)ethanol

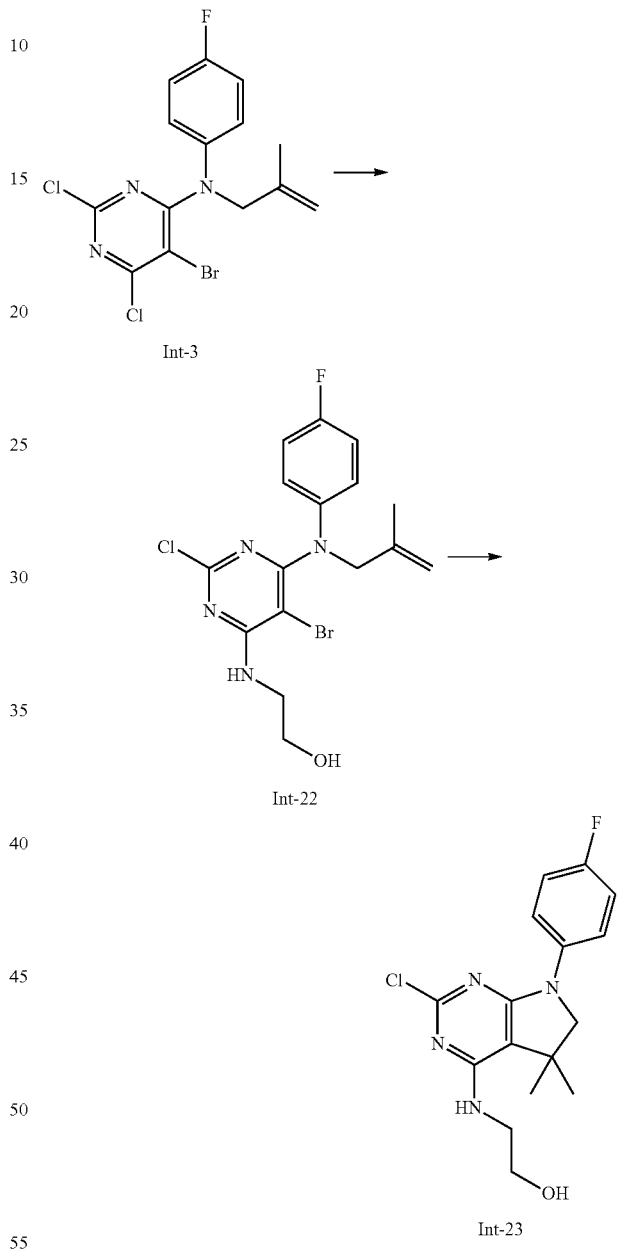

Step 1: 2-((5-Bromo-2-chloro-6-((4-fluorophenyl) (2-methylallyl)amino)pyrimidin-4-yl)amino)ethanol (Int-22)

5-Bromo-2,6-dichloro-N-(3,4-difluorophenyl)-N-(2-methylallyl)pyrimidin-4-amine (Int-3, 1.30 g, 3.32 mmol) was dissolved in tetrahydrofuran (4 mL) and a solution of 2-aminoethanol (772 mg, 12.6 mmol) in tetrahydrofuran (4.3 mL) was added dropwise. The mixture was stirred at room temperature for 3.5 h. After that, water (10 mL) was added, the mixture was extracted with ethyl acetate (2×100 mL), the organic layers were washed with brine (10 mL), combined, dried (sodium sulfate) and concentrated in vacuo. The crude product was purified by column chromatography (silica gel, 80 g, eluting with ethyl acetate/n-heptane, gradient 0:100 to 30:70) to afford the title compound as a white solid (684 mg, 49%). HPLC (method LCMS_fastgradient) $t_R$=1.41 min. $^1$H NMR (CDCl$_3$, 300 MHz): δ 1.78 (s, 3H), 2.59 (s, 1H), 3.64-3.68 (m, 2H), 3.83 (t, J=4.9 Hz, 2H), 4.52 (s, 2H), 4.86-4.89 (m, 1H), 4.92 (s, 1H), 5.90 (t, J=5.0 Hz, 1H), 6.95-7.03 (m, 4H). MS (ES+) m/z 415.1, 417.1, 419.1 [M+H, Br and Cl isotopes].

Step 2: 2-((2-Chloro-7-(4-fluorophenyl)-5,5-dimethyl-6,7-dihydro-5H-pyrrolo[2,3-d]pyrimidin-4-yl)amino)ethanol (Int-23)

2-((5-Bromo-2-chloro-6-((4-fluorophenyl)(2-methylallyl)amino)pyrimidin-4-yl)amino)-ethanol (Int-22, 670 mg, 1.61 mmol), sodium formate (115 mg, 1.69 mmol), tetrabutylammonium chloride (457 mg, 1.64 mmol) and palladium (II) acetate (84 mg, 374 µmol) were charged under argon in a 50 mL round bottomed flask. Dimethylformamide (5 mL), followed by triethylamine (414 mg, 4.09 mmol) were added and the flask was evacuated carefully and backfilled with argon. The resulting mixture was stirred at 80° C. for 18 h. After cooling, water (5 mL) was added, the mixture was extracted with methyltertbutyl ether (2×100 mL), the organic layers were washed with water (3×5 mL) and brine (1×5 mL), combined, dried (sodium sulfate) and concentrated in vacuo. The crude product was purified by column chromatography (silica gel, 25 g, eluting with ethyl acetate/n-heptane, gradient 0:100 to 60:40) to afford the title compound as a brown solid (393 mg, 72%). HPLC (method LCMS_fastgradient) $t_R$=1.27 min. $^1$H NMR (CDCl$_3$, 300 MHz): δ 1.44 (s, 6H), 2.95 (t, J=4.9 Hz, 1H), 3.64-3.71 (m, 2H), 3.73 (s, 2H), 3.81-3.87 (m, 2H), 4.81 (t, J=5.3 Hz, 1H), 7.06 (dd, J=8.4, 9.4 Hz, 2H), 7.54-7.62 (m, 2H). MS (ES+) m/z 337.2, 339.2 [M+H, Cl isotopes].

Intermediate 27

2-Chloro-8-(4-fluorophenyl)-N,5,5-trimethyl-5,6,7,8-tetrahydropyrido[2,3-d]pyrimidin-4-amine

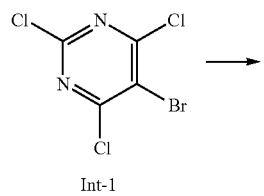

Int-1

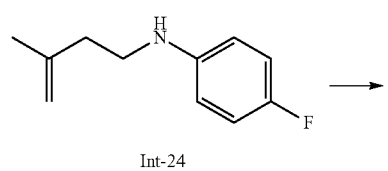

Int-24

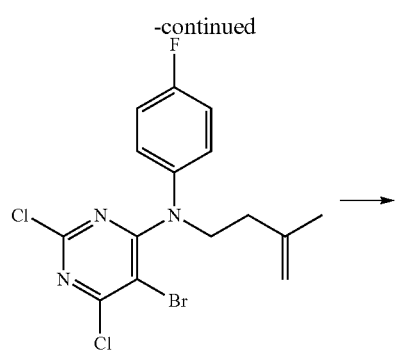

Int-25

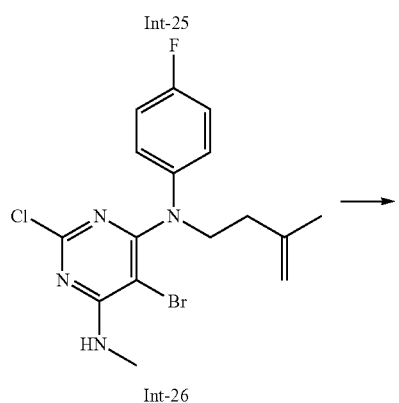

Int-26

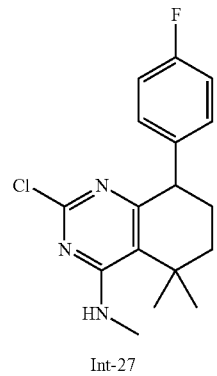

Int-27

Step 1: 4-Fluoro-N-(3-methylbut-3-en-1-yl)aniline (Int-24)

4-Fluoroaniline (498 mg, 4.48 mmol) and potassium carbonate (1.03 g, 7.46 mmol) were suspended in DMF (9 mL). A solution of 4-bromo-2-methylbut-1-ene (556 mg, 3.73 mmol) in DMF (2 mL) was added drop-wise and the reaction mixture was stirred at 80° C. for 18 h. After cooling to room temperature, water (10 mL) was added and the resulting mixture was extracted with tertbutylmethyl ether (2×80 mL), the organic layers were washed with water (3×10 mL) and brine (1×10 mL), combined, dried (sodium sulfate) and concentrated in vacuo. The crude product was purified by column chromatography (silica gel, 25 g, eluting with ethyl acetate/n-heptane, gradient 0:100 to 5:95) to afford the title compound as a yellow oil (384 mg, 57%). HPLC (method LCMS_fastgradient) $t_R$=1.15 min. $^1$H NMR (CDCl$_3$, 300 MHz): δ 1.77 (s, 3H), 2.31-2.39 (m, 2H), 3.13-3.23 (m, 2H), 3.53 (br s, 1H), 4.77-4.82 (m, 1H), 4.85-4.89 (m, 1H), 6.51-6.59 (m, 2H), 6.85-6.94 (m, 2H). MS (ES+) m/z 180.1 [M+H].

Step 2: 5-Bromo-2,6-dichloro-N-(4-fluorophenyl)-N-(3-methylbut-3-en-1-yl)pyrimidin-4-amine (Int-25)

4-Fluoro-N-(3-methylbut-3-en-1-yl)aniline (Int-24, 382 mg, 2.13 mmol) was dissolved in THF (4 mL) and water (2 mL), and sodium acetate (525 mg, 6.39 mmol), followed by 5-bromo-2,4,6-trichloropyrimidine (589 mg, 2.13 mmol) were added. The mixture was stirred at room temperature for 18 h. After that, a saturated aqueous solution of sodium hydrogencarbonate (10 mL) was added and the resulting mixture was extracted with ethyl acetate (2×80 mL). The combined organic layers were dried (sodium sulfate) and concentrated in vacuo. The crude was purified by column chromatography (silica gel, 40 g, eluting with ethyl acetate/n-heptane, gradient 0:100 to 5:95) to yield, after drying in vacuo (40° C., 5 mbar), the title compound as a yellow solid (527 mg, 61%). HPLC (method LCMS_fastgradient) $t_R$=1.70 min. $^1$H NMR (CDCl$_3$, 300 MHz): δ 1.79 (s, 3H), 2.32-2.40 (m, 2H), 4.01-4.08 (m, 2H), 4.67-4.71 (m, 1H), 4.78-4.82 (m, 1H), 7.06-7.11 (m, 4H). MS (ES+) m/z 404.1, 406.1, 408.1 [M+H, Br and 2 Cl isotopes].

Step 3: 5-Bromo-2-chloro-N4-(4-fluorophenyl)-N6-methyl-N4-(3-methylbut-3-en-1-yl)pyrimidine-4,6-diamine (Int-26)

5-Bromo-2,6-dichloro-N-(4-fluorophenyl)-N-(3-methylbut-3-en-1-yl)pyrimidin-4-amine (Int-25, 519 mg, 1.28 mmol) was dissolved in tetrahydrofuran (3 mL), the solution was cooled to 0-5° C. (ice bath) and a solution of methylamine in tetrahydrofuran (2.0 M, 2.4 mL, 4.8 mmol) was added dropwise. The mixture was stirred at 0-5° C. for 1 h, followed by 1 h at room temperature. After that, water (5 mL) was added, the mixture was extracted with ethyl acetate (2×40 mL), the organic layers were washed with brine (1×5 mL), combined, dried (sodium sulfate) and concentrated in vacuo. The crude product was purified by column chromatography (silica gel, 25 g, eluting with ethyl acetate/n-heptane, gradient 0:100 to 5:95) to afford the title compound as an off-white solid (274 mg, 53%). HPLC (method LCMS_fastgradient) $t_R$=1.64 min. $^1$H NMR (CDCl$_3$, 300 MHz): δ 1.79 (s, 3H), 2.31-2.39 (m, 2H), 3.03 (d, J=4.8 Hz, 3H), 3.93-4.01 (m, 2H), 4.66-4.70 (m, 1H), 4.75-4.78 (m, 1H), 5.40-5.50 (m, 1H), 6.99-7.04 (m, 4H). MS (ES+) m/z 399.1, 401.1, 403.1 [M+H, Br and Cl isotopes].

Step 4: 2-Chloro-8-(4-fluorophenyl)-N,5,5-trimethyl-5,6,7,8-tetrahydropyrido[2,3-d]pyrimidin-4-amine (Int-27)

5-Bromo-2-chloro-N4-(4-fluorophenyl)-N6-methyl-N4-(3-methylbut-3-en-1-yl)pyrimidine-4,6-diamine (Int-26, 270 mg, 676 μmol), sodium formate (51 mg, 750 μmol), tetrabutylammonium chloride (188 mg, 676 μmol) and palladium (II) acetate (76 mg, 339 μmol) were charged under argon in a 25 mL round bottomed flask. Dimethylformamide (1.7 mL), followed by triethylamine (182 mg, 1.79 mmol) were added and the flask was evacuated carefully and backfilled with argon. The resulting mixture was stirred at 110° C. for 18 h. After cooling, water (5 mL) was added, the mixture was extracted with a mixture of methyltertbutyl ether/ethyl acetate (1:1 v/v, 2×40 mL), the organic layers were washed with water (3×5 mL) and brine (1×5 mL), combined, dried (sodium sulfate) and concentrated in vacuo. The crude product was purified by column chromatography (silica gel, 12 g, eluting with ethyl acetate/n-heptane, gradient 0:100 to 20:80) to yield the title compound as an off-white solid (104 mg, 48%). HPLC (method LCMS_fastgradient) $t_R$=1.39 min. $^1$H NMR (CDCl$_3$, 300 MHz): δ 1.40 (s, 6H), 1.87-1.93 (m, 2H), 3.05 (d, J=4.6 Hz, 3H), 3.58-3.64 (m, 2H), 4.60-4.69 (m, 1H), 7.00-7.08 (m, 2H), 7.16-7.22 (m, 2H). MS (ES+) m/z 321.2, 323.2 [M+H, Cl isotopes].

Intermediate 30

2,4-Dichloro-7-(4-fluorophenyl)-6,7-dihydro-5H-pyrrolo[2,3-d]pyrimidine

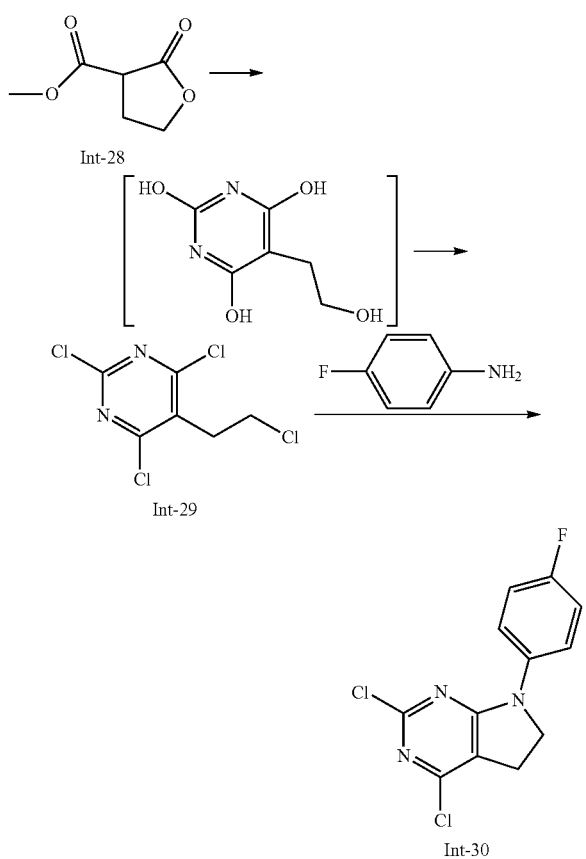

Step 1: 2,4,6-Trichloro-5-(2-chloroethyl)pyrimidine (Int-29)

Methyl 2-oxotetrahydrofuran-3-carboxylate (Int-28, 5.20 g, 36.1 mmol) was dissolved in ethanol (40 mL) and urea (2.17 g, 36.1 mmol) was added, followed by a solution of sodium ethoxide in ethanol (21% m/m, 24.3 g, 28 mL, 75 mmol). The resulting suspension was stirred at 75° C. for 18 h. After that, it was cooled to room temperature and concentrated in vacuo. The residue, a light brown solid (8.87 g), was added carefully in small portions to precooled (0-5° C., ice bath) phosphorus oxychloride (57.6 g, 35 mL). Strong fuming was observed. After that, N,N-dimethylaniline (5.74 g, 47.3 mmol) was added and the reaction mixture was stirred at 100° C. for 18 h. Then, it was cooled to room temperature, poured into ice water (480 g) and stirred for 1 h, until the ice was melted. The formed precipitate was filtered off, washed with water and dried in vacuo to afford the title compound as a dark brown solid (3.8 g, 43%), that was used without further purification in the next step. ¹H NMR (DMSO-d6, 300 MHz): δ 3.31 (t, J=7.2 Hz, 2H), 3.86 (t, J=7.2 Hz, 2H).

Step 2: 2,4-Dichloro-7-(4-fluorophenyl)-6,7-dihydro-5H-pyrrolo[2,3-d]pyrimidine (Int-30)

2,4,6-Trichloro-5-(2-chloroethyl)pyrimidine (Int-29, 1.84 g, 7.48 mmol) was dissolved in acetonitrile (40 mL), and 4-fluoroaniline (833 mg, 7.5 mmol), followed by N,N-diisopropylethylamine (2.0 g, 2.7 mL, 15.5 mmol) were added dropwise. The mixture was stirred at room temperature for 7 h and at 50° C. for 18 h. Then, it was concentrated in vacuo and the resulting crude product was purified directly by column chromatography (silica gel, 80 g, eluting with dichloromethane/n-heptane, gradient 0:100 to 80:20) to give a yellow solid, which was further triturated with a mixture of ethyl acetate/n-heptane (1:4, v/v) to afford, after filtration and drying in vacuo, the title compound as an off-white solid (893 mg, 42%). HPLC (method LCMS_fastgradient) $t_R$=1.37 min. ¹H NMR (CDCl₃, 300 MHz): δ 3.19 (dd, J=8.3, 9.1 Hz, 2H), 4.20 (dd, J=8.3, 9.1 Hz, 2H), 7.12 (dd, J=8.1, 9.3 Hz, 2H), 7.67 (dd, J=4.6, 9.3 Hz, 2H). MS (ES+) m/z 284.1, 286.0 [M+H, 2 Cl isotopes].

Intermediate 34

2,4-Dichloro-7-(4-fluorophenyl)-5-methyl-6,7-dihydro-5H-pyrrolo[2,3-d]pyrimidine

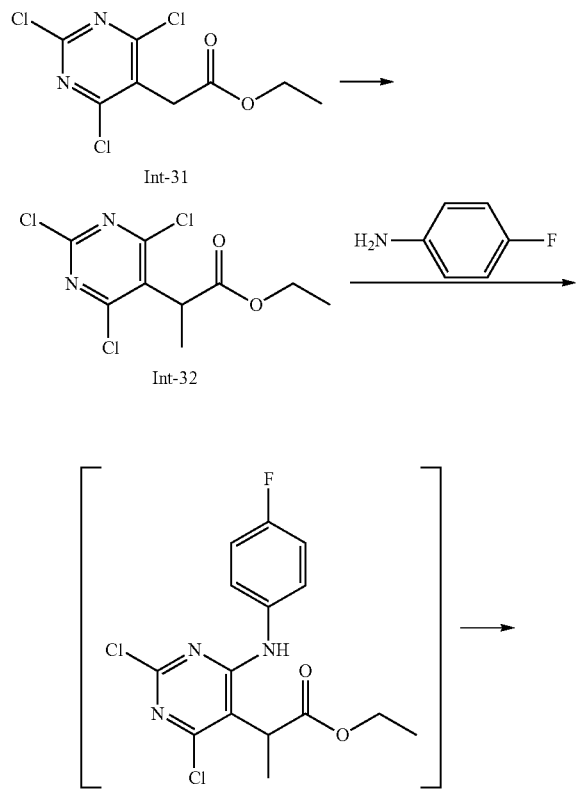

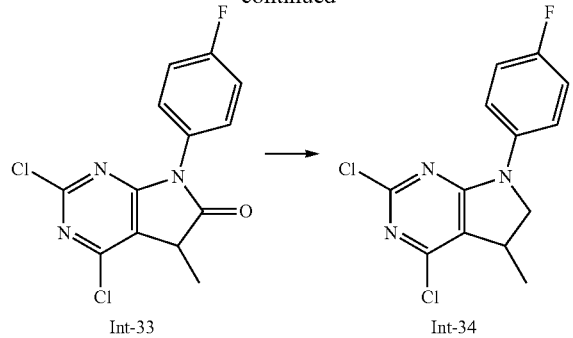

Step 1: Ethyl 2-(2,4,6-trichloropyrimidin-5-yl)propanoate (Int-32)

Ethyl 2-(2,4,6-trichloropyrimidin-5-yl)acetate (Int-31, prepared as described in WO20120928800, 3.3 g, 12.2 mmol) was dissolved in dry tetrahydrofuran (75 mL) and the solution was cooled to −76° C. (dry ice/acetone bath). A solution of lithium hexamethyldisilazide in tetrahydrofuran/ethylbenzene (1M, 12.2 mL, 12.2 mmol) was added over 10 min, and the resulting orange solution was stirred at −76° C. for 45 min. Then, a solution of iodomethane (2.09 g, 14.7 mmol) in dry tetrahydrofuran (6 mL) was added over 15 min at that temperature. The resulting mixture was stirred for 3 h at −23 to −16° C. (ice/ethanol bath). After that, a saturated aqueous solution of ammonium chloride (80 mL), followed by water (100 mL) was added, the resulting mixture was extracted with ethyl acetate (2×80 mL), the combined organic layers were washed with semi-saturated brine (1×100 mL), dried (sodium sulfate) and concentrated in vacuo. The crude product was purified by column chromatography (silica gel, 80 g, eluting with ethyl acetate/n-heptane, gradient 1:99 to 2:98) to afford the title compound as a colorless oil (2.88 g, 82%). HPLC (method LCMS_fastgradient) $t_R$=1.32 min. ¹H NMR (CDCl₃, 300 MHz): δ 1.24 (t, J=7.1 Hz, 3H), 1.56 (d, J=7.2 Hz, 3H), 4.16-4.27 (m, 2H), 4.34 (q, J=7.2 Hz, 1H). MS (ES+) m/z 283.0, 285.0, 287.0 [M+H, 3 Cl isotopes].

Step 2: 2,4-Dichloro-7-(4-fluorophenyl)-5-methyl-5H-pyrrolo[2,3-d]pyrimidin-6(7H)-one (Int-33)

Ethyl 2-(2,4,6-trichloropyrimidin-5-yl)propanoate (Int-32, 8.9 g, 31.4 mmol) was dissolved in tetrahydrofuran (70 mL) and 4-fluoroaniline (3.84 g, 34.5 mmol) was added, followed by a solution of diisopropylethylamine (5.27 g, 40.8 mmol) in tetrahydrofuran (10 mL). The resulting solution was stirred for 4 h at 66° C. (reflux). After cooling, the solvent was distilled off and the crude product directly purified by column chromatography (silica gel, 220 g, eluting with ethyl acetate/n-heptane, gradient 1:99 to 15:85) to yield, after trituration with diethyl ether/n-heptane (1:4 v/v, 50 mL) and drying in vacuo (40° C., 5 mbar), the title compound as a yellow solid (2.1 g, 21%). HPLC (method LCMS_fastgradient) $t_R$=1.27 min. ¹H NMR (CDCl₃, 300 MHz): δ 1.72 (d, J=7.7 Hz, 3H), 3.77 (q, J=7.7 Hz, 1H), 7.23 (dd, J=8.2, 9.2 Hz, 2H), 7.45 (dd, J=4.7, 9.2 Hz, 2H). MS (ES+) m/z 312.0, 314.0 [M+H, 2 Cl isotopes].

Step 3: 2,4-Dichloro-7-(4-fluorophenyl)-5-methyl-6,7-dihydro-5H-pyrrolo[2,3-d]pyrimidine (Int-34)

2,4-Dichloro-7-(4-fluorophenyl)-5-methyl-5H-pyrrolo[2,3-d]pyrimidin-6(7H)-one (Int-33, 1.83 g, 5.86 mmol) was dissolved in dry tetrahydrofuran (75 mL), the solution was cooled to 0-5° C. (ice bath) and a solution of borane-tetrahydrofuran complex in tetrahydrofuran (1.0 M, 14.7 mL, 14.7 mmol) was added over 15 min. The mixture was stirred at 75° C. for 16 h. After cooling to room temperature, methanol (5 mL) was added dropwise, followed by water (40 mL) and a 1M aqueous solution of hydrogen chloride (40 mL). The mixture was stirred for 30 min at room temperature. Then, the pH was adjusted to 6-7 by addition of solid sodium hydrogencarbonate. The aqueous layer was separated and extracted with ethyl acetate (60 mL), the combined organic layers were washed with brine (1×100 mL), dried (sodium sulfate) and concentrated in vacuo. The crude product was purified by column chromatography (silica gel, 80 g, eluting with ethyl acetate/n-heptane, gradient 3:97 to 20:80), followed by a second column chromatography (silica gel, 120 g, eluting with (ethyl acetate/dichloromethane 1:1 (v/v))/n-heptane, gradient 5:95 to 10:90) to afford the title compound as an white solid (471 mg, 27%). HPLC (method LCMS_fastgradient) $t_R$=1.44 min. $^1$H NMR (CDCl$_3$, 300 MHz): δ 1.44-1.51 (m, 3H), 3.48-3.62 (m, 1H), 3.68-3.77 (m, 1H), 4.29-4.39 (m, 1H), 7.08-7.18 (m, 2H), 7.63-7.72 (m, 2H). MS (ES+) m/z 298.0, 300.0 [M+H, 2 Cl isotopes].

Intermediates 34p and 34q (−)-2,4-Dichloro-7-(4-fluorophenyl)-5-methyl-6,7-dihydro-5H-pyrrolo[2,3-d]pyrimidine (Int-34p) and (+)-2,4-dichloro-7-(4-fluorophenyl)-5-methyl-6,7-dihydro-5H-pyrrolo[2,3-d]pyrimidine (Int-34q)

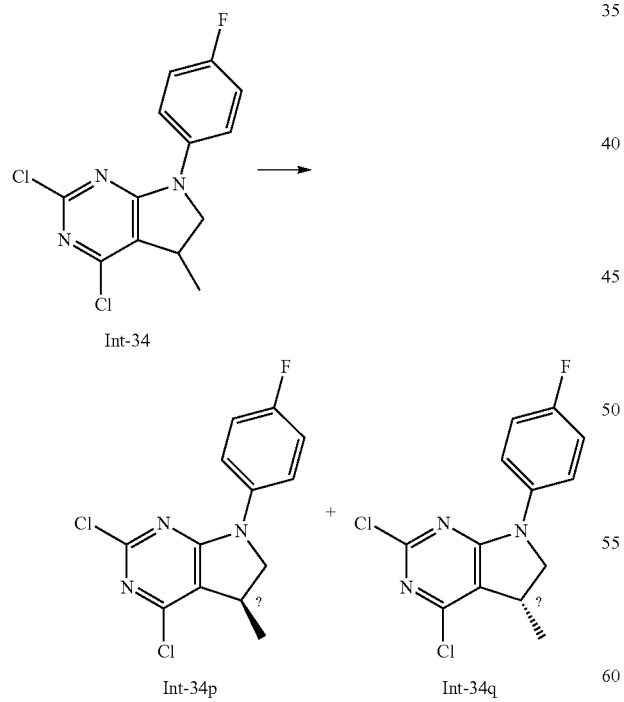

Racemic 2,4-dichloro-7-(4-fluorophenyl)-5-methyl-6,7-dihydro-5H-pyrrolo[2,3-d]pyrimidine (Int-34, 100 mg) was separated in the enantiomers using preparative chiral HPLC (Reprosil Chiral-NR, eluting with n-heptane/2-propanol 80:20 (v/v)) to yield, after concentration of the combined product containing fractions in vacuo, Int-34p as first eluting, (−)-rotating enantiomer (37 mg, 37%), and Int-34q as second eluting, (+)-rotating enantiomer (41 mg, 41%). The stereocenters in the chemical drawing above were assigned arbitrarily to clarify the presence of separated enantiomers. The unambigious enantiomer assignment is Int-34p-(−)-rotating, and Int-34q-(+)-rotating.

Intermediate 43

2-Chloro-7-(2,3-difluorophenyl)-N,5,5-trimethyl-6,7-dihydro-5H-pyrrolo[2,3-d]pyrimidin-4-amine

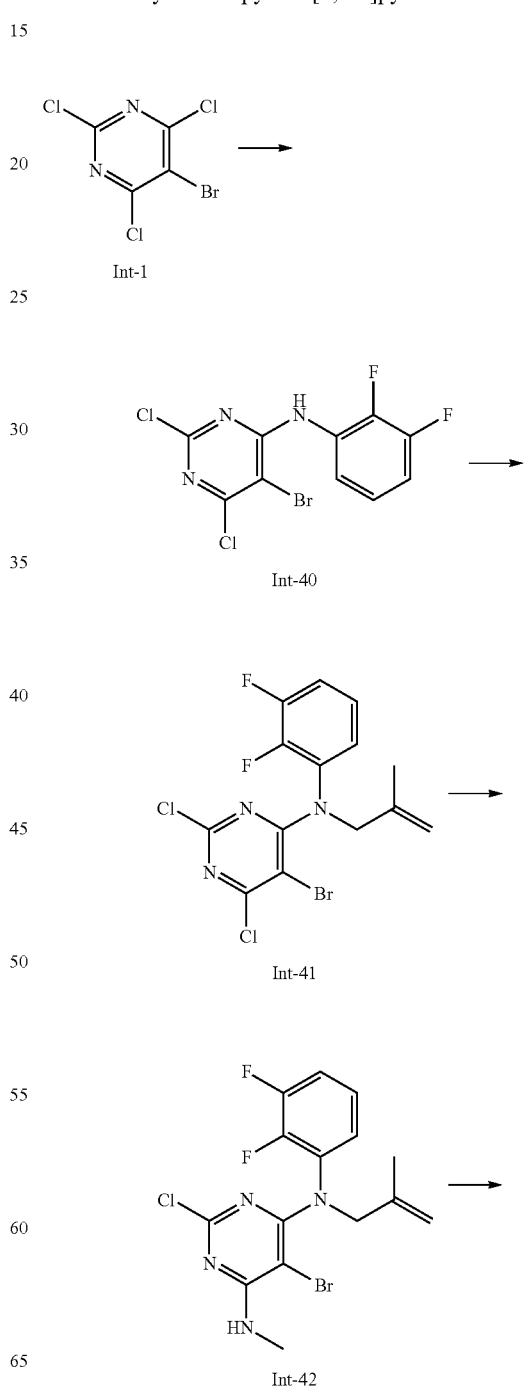

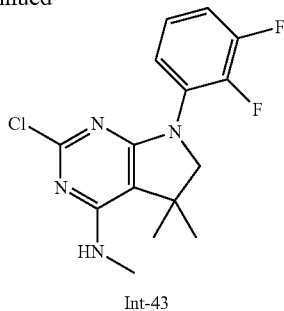

Int-43

Step 1: 5-Bromo-2,6-dichloro-N-(2,3-difluorophenyl)pyrimidin-4-amine (Int-40)

5-Bromo-2,4,6-trichloropyrimidine (2.30 g, 8.33 mmol) was dissolved in THF (14 mL) and water (7 mL), and sodium acetate (2.05 g, 25.0 mmol), followed by 2,3-difluoroaniline (1.15 g, 0.90 mL, 8.7 mmol) were added. The mixture was stirred at room temperature for 18 h. After that, a saturated aqueous solution of sodium hydrogencarbonate (20 mL) was added and the resulting mixture was extracted with ethyl acetate (2×100 mL). The combined organic layers were dried (sodium sulfate) and concentrated in vacuo. The crude was purified by column chromatography (silica gel, 80 g, eluting with ethyl acetate/n-heptane, gradient 0:100 to 10:90) to yield, after drying in vacuo (40° C., 5 mbar), the title compound as a light brown solid (1.23 g, 42%). HPLC (method LCMS_fastgradient) $t_R$=1.38 min. $^1$H NMR (CDCl$_3$, 300 MHz): δ 6.97-7.09 (m, 1H), 7.13-7.23 (m, 1H), 7.72 (br s, 1H), 8.03-8.11 (m, 1H). MS (ES+) m/z 353.8, 355.8, 357.8 [M+H, Br and 2 Cl isotopes].

Step 2: 5-Bromo-2,6-dichloro-N-(2,3-difluorophenyl)-N-(2-methylallyl)pyrimidin-4-amine (Int-41)

5-Bromo-2,6-dichloro-N-(2,3-difluorophenyl)pyrimidin-4-amine (Int-40, 1.23 g, 3.47 mmol) was dissolved in dimethylformamide (11 mL) and sodium hydride (60% dispersion in mineral oil, 193 mg, 4.82 mmol) was added carefully (gas evolution). The mixture was stirred at room temperature for 1 h. Then, 3-bromo-2-methylprop-1-ene (830 mg, 6.15 mmol) was added and the resulting mixture was stirred for 16 h at 50° C. After that, water (15 mL) was added, the mixture was extracted with methyltertbutyl ether (2×80 mL), the organic phases were washed with water (3×15 mL) and brine (15 mL), combined, dried (sodium sulfate), and concentrated in vacuo. The crude product was purified by column chromatography (silica gel, 80 g, eluting with ethyl acetate/n-heptane, gradient 0:100 to 5:95) to afford the title compound as a yellow oil (1.20 g, 76%). HPLC (method LCMS_fastgradient) $t_R$=1.65 min. $^1$H NMR (CDCl$_3$, 300 MHz): δ 1.80 (s, 3H), 4.60 (s, 2H), 4.83-4.86 (m, 1H), 4.88-4.91 (m, 1H), 6.94-7.01 (m, 1H), 7.03-7.15 (m, 2H). MS (ES+) m/z 408.1, 410.1, 412.1 [M+H, Br and 2 Cl isotopes].

Step 3: 5-Bromo-2-chloro-N4-(2,3-difluorophenyl)-N6-methyl-N4-(2-methylallyl)-pyrimidine-4,6-diamine (Int-42)

5-Bromo-2,6-dichloro-N-(2,3-difluorophenyl)-N-(2-methylallyl)pyrimidin-4-amine (Int-41, 1.19 g, 2.62 mmol) was dissolved in tetrahydrofuran (6.5 mL), the solution was cooled to 0-5° C. (ice bath) and a solution of methylamine in tetrahydrofuran (2.0 M, 4.8 mL, 9.6 mmol) was added dropwise. The mixture was stirred at room temperature for 1.5 h. After that, water (10 mL) was added, the mixture was extracted with ethyl acetate (2×80 mL), the organic layers were washed with brine (10 mL), combined, dried (sodium sulfate) and concentrated in vacuo. The crude product was purified by column chromatography (silica gel, 40 g, eluting with ethyl acetate/n-heptane, gradient 0:100 to 5:95) to obtain the title compound as a colorless oil (578 mg, 55%). HPLC (method LCMS_fastgradient) $t_R$=1.56 min. $^1$H NMR (CDCl$_3$, 300 MHz): δ 1.78 (s, 3H), 3.05 (d, J=4.8 Hz, 3H), 4.53 (s, 2H), 4.83-4.87 (m, 1H), 4.87-4.90 (m, 1H), 5.45-5.56 (m, 1H), 6.87-6.94 (m, 1H), 6.95-7.03 (m, 2H). MS (ES+) m/z 402.9, 404.8, 406.9 [M+H, Br and Cl isotopes].

Step 4: 2-Chloro-7-(2,3-difluorophenyl)-N,5,5-trimethyl-6,7-dihydro-5H-pyrrolo[2,3-d]pyrimidin-4-amine (Int-43)

5-Bromo-2-chloro-N4-(2,3-difluorophenyl)-N6-methyl-N4-(2-methylallyl)pyrimidine-4,6-diamine (Int-42, 565 mg, 1.40 mmol), sodium formate (101 mg, 1.48 mmol), tetrabutylammonium chloride (397 mg, 1.43 mmol) and palladium (II) acetate (72 mg, 321 µmol) were charged under argon in a 25 mL round bottomed flask. Dimethylformamide (4.2 mL), followed by triethylamine (363 mg, 3.59 mmol) were added and the flask was evacuated carefully and backfilled with argon. The resulting mixture was stirred at 80° C. for 18 h. After cooling, water (5 mL) was added, the mixture was extracted with methyltertbutyl ether (2×70 mL), the organic layers were washed with water (3×5 mL) and brine (1×5 mL), combined, dried (sodium sulfate) and concentrated in vacuo. The crude product was purified by column chromatography (silica gel, 24 g, eluting with ethyl acetate/n-heptane, gradient 0:100 to 20:80) to yield the title compound as a light yellow solid (382 mg, 84%). HPLC (method LCMS_fastgradient) $t_R$=1.36 min. $^1$H NMR (CDCl$_3$, 300 MHz): δ 1.42 (s, 6H), 3.08 (d, J=4.8 Hz, 3H), 3.75 (d, J=1.6 Hz, 2H), 4.29-4.40 (m, 1H), 6.93-7.03 (m, 1H), 7.03-7.12 (m, 1H), 7.35-7.43 (m, 1H). MS (ES+) m/z 325.0, 327.0 [M+H, Cl isotopes].

Intermediate 47

2-Chloro-7-(2,4-difluorophenyl)-N,5,5-trimethyl-6,7-dihydro-5H-pyrrolo[2,3-d]pyrimidin-4-amine

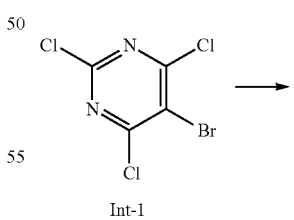

Int-1

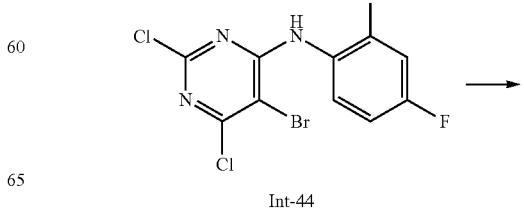

Int-44

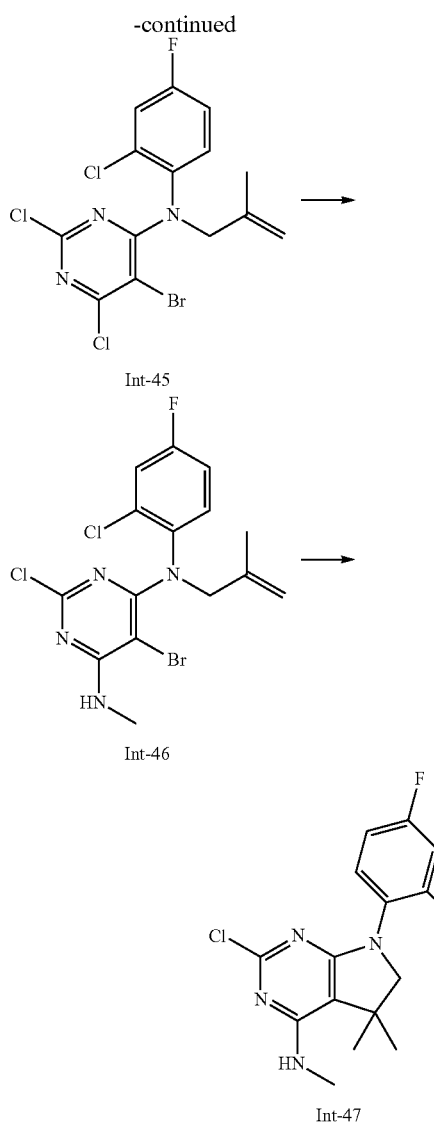

Step 1: 5-Bromo-2,6-dichloro-N-(2-chloro-4-fluorophenyl)pyrimidin-4-amine (Int-44)

2-Chloro-4-fluoroaniline (512 mg, 0.42 mL, 3.45 mmol) was dissolved in THF (10 mL), the solution was cooled to 0-5° C. (ice bath) and a solution of lithium bis(trimethylsilyl)amide in tetrahydrofuran/ethylbenzene (1.0 M, 3.4 mL, 3.4 mmol) was added. After stirring for 15 min at 0-5° C., a solution of 5-bromo-2,4,6-trichloropyrimidine (900 mg, 3.26 mmol) in tetrahydrofuran (7 mL) was added dropwise. The reaction mixture was stirred for 18 h at room temperature. During that period, two additional portions of a solution of lithium bis(trimethylsilyl)amide in tetrahydrofuran/ethylbenzene (1.0 M, 1.7 mL & 0.82 mL, 1.7 mmol & 0.82 mmol) were added at 0-5° C. after 45 min and 2 h, respectively. Then, water (10 mL) and a saturated aqueous solution of ammonium chloride (30 mL) were added and the resulting mixture was extracted with ethyl acetate (2×150 mL). The organic layers were washed with water (15 mL) and brine (15 mL), combined, dried (sodium sulfate) and concentrated in vacuo. The crude was purified by column chromatography (silica gel, 40 g, eluting with ethyl acetate/n-heptane, gradient 0:100 to 5:95) to yield, after drying in vacuo (40° C., 5 mbar), the title compound as an off-white solid (956 mg, 79%). HPLC (method LCMS_fastgradient) $t_R$=1.47 min. $^1$H NMR (CDCl$_3$, 300 MHz): δ 7.08-7.16 (m, 1H), 7.24 (dd, J=2.8, 7.9 Hz, 1H), 7.99 (br s, 1H), 8.33 (dd, J=5.4, 9.3 Hz, 1H). MS (ES+) m/z 370.0, 372.0, 374.0 [M+H, Br and 3 Cl isotopes].

Step 2: 5-Bromo-2,6-dichloro-N-(2-chloro-4-fluorophenyl)-N-(2-methylallyl)pyrimidin-4-amine (Int-45)

5-Bromo-2,6-dichloro-N-(2-chloro-4-fluorophenyl)pyrimidin-4-amine (Int-44, 1.61 g, 4.33 mmol) was dissolved in dimethylformamide (14 mL) and sodium hydride (60% dispersion in mineral oil, 241 mg, 6.03 mmol) was added carefully (gas evolution). The mixture was stirred at room temperature for 1 h. Then, 3-bromo-2-methylprop-1-ene (1.00 g, 7.44 mmol) was added and the resulting mixture was stirred for 4.5 h at 60° C. After that, a second portion of sodium hydride (60% dispersion in mineral oil, 80 mg, 2.0 mmol) and 3-bromo-2-methylprop-1-ene (335 mg, 2.48 mmol) was added and the resulting mixture was stirred for 16 h at 60° C. After cooling to room temperature, water (15 mL) was added, the mixture was extracted with methyltert-butyl ether (2×80 mL), the organic phases were washed with water (3×15 mL) and brine (15 mL), combined, dried (sodium sulfate), and concentrated in vacuo. The crude product was purified by column chromatography (silica gel, 80 g, eluting with ethyl acetate/n-heptane, gradient 0:100 to 5:95) to afford the title compound as a light yellow oil (1.73 g, 84%). HPLC (method LCMS_fastgradient) $t_R$=1.71 min. $^1$H NMR (CDCl$_3$, 300 MHz): δ 1.82 (s, 3H), 4.32-4.62 (br s, exch., 2H), 4.77-4.82 (m, 1H), 4.88-4.92 (m, 1H), 6.98-7.06 (m, 1H), 7.16-7.26 (m, 2H). MS (ES+) m/z 423.8, 425.8, 427.8 [M+H, Br and 3 Cl isotopes].

Step 3: 5-Bromo-2-chloro-N4-(2-chloro-4-fluorophenyl)-N6-methyl-N4-(2-methylallyl)-pyrimidine-4,6-diamine (Int-46)

5-Bromo-2,6-dichloro-N-(2-chloro-4-fluorophenyl)-N-(2-methylallyl)pyrimidin-4-amine (Int-45, 1.73 g, 3.66 mmol) was dissolved in tetrahydrofuran (10 mL), the solution was cooled to 0-5° C. (ice bath) and a solution of methylamine in tetrahydrofuran (2.0 M, 6.75 mL, 13.5 mmol) was added dropwise. The mixture was stirred at room temperature for 1.5 h. After that, water (15 mL) was added, the mixture was extracted with ethyl acetate (2×110 mL), the organic layers were washed with brine (15 mL), combined, dried (sodium sulfate) and concentrated in vacuo. The crude product was purified by column chromatography (silica gel, 80 g, eluting with ethyl acetate/n-heptane, gradient 0:100 to 5:95) to obtain the title compound as a colorless oil (658 mg, 43%). HPLC (method LCMS_fastgradient) $t_R$=1.62 min. $^1$H NMR (CDCl$_3$, 300 MHz): δ 1.80 (s, 3H), 3.03 (d, J=4.8 Hz, 3H), 4.44 (s, 2H), 4.81-4.86 (m, 2H), 5.42-5.52 (m, 1H), 6.95 (ddd, J=2.8, 7.7, 8.9 Hz, 1H), 7.14 (dd, J=2.8, 8.3 Hz, 1H), 7.18 (dd, J=5.6, 8.9 Hz, 1H). MS (ES+) m/z 418.9, 420.8, 422.9 [M+H, Br and 2 Cl isotopes].

Step 4: 2-Chloro-7-(2-chloro-4-fluorophenyl)-N,5,5-trimethyl-6,7-dihydro-5H-pyrrolo[2,3-d]pyrimidin-4-amine (Int-47)

5-Bromo-2-chloro-N4-(2-chloro-4-fluorophenyl)-N6-methyl-N4-(2-methylallyl)pyrimidine-4,6-diamine (Int-46, 645 mg, 1.54 mmol), sodium formate (111 mg, 1.63 mmol), tetrabutylammonium chloride (435 mg, 1.57 mmol) and palladium (II) acetate (79 mg, 352 µmol) were charged under argon in a 25 mL round bottomed flask. Dimethylformamide (4.6 mL), followed by triethylamine (399 mg, 3.95 mmol) were added and the flask was evacuated carefully and backfilled with argon. The resulting mixture was stirred at 80° C. for 18 h. After cooling, water (5 mL) was added, the mixture was extracted with methyltertbutyl ether (2×70 mL), the organic layers were washed with water (3×5 mL) and brine (1×5 mL), combined, dried (sodium sulfate) and concentrated in vacuo. The crude product was purified by column chromatography (silica gel, 40 g, eluting with ethyl acetate/n-heptane, gradient 0:100 to 20:80) to yield the title compound as a light yellow solid (344 mg, 66%). HPLC (method LCMS_fastgradient) $t_R$=1.39 min. $^1$H NMR (CDCl$_3$, 300 MHz): δ 1.43 (s, 6H), 3.07 (d, J=4.8 Hz, 3H), 3.61 (s, 2H), 4.26-4.35 (m, 1H), 7.03 (ddd, J=2.9, 7.8, 8.9 Hz, 1H), 7.19 (dd, J=2.8, 8.3 Hz, 1H), 7.35 (dd, J=5.4, 8.9 Hz, 1H). MS (ES+) m/z 341.2, 343.1 [M+H, 2 Cl isotopes].

The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield a yellow oil. This was triturated with tertbutylmethyl ether/heptane (ca. 1:1 v/v, 10 mL), the resulting suspension was filtered and dried in vacuo to afford a yellow solid. The solid was dissolved in dichloromethane (5 mL), the solution was concentrated in vacuo and dried in high vacuum to yield the title compound as a light yellow foam (60 mg, 55%). HPLC (method LCMS_fastgradient) $t_R$=1.26 min. $^1$H NMR (CDCl$_3$, 300 MHz): δ 1.42 (s, 6H), 2.49 (s, 3H), 3.12 (d, J=4.8 Hz, 3H), 3.67 (s, 2H), 3.84 (s, 3H), 4.21-4.25 (m, 1H), 6.99-7.07 (m, 4H), 7.54 (d, J=8.7 Hz, 1H), 7.62 (dd, J=4.7, 9.2 Hz, 2H), 7.87 (d, J=1.9 Hz, 1H), 8.48 (s, 1H). MS (ES+) m/z 475.3 [M+H].

Example 1

7-(4-Fluorophenyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine Example 2

N2-(3-(Difluoromethoxy)-4-(3-methyl-1H-1,2,4-triazol-1-yl)phenyl)-7-(4-fluorophenyl)-N4,5,5-trimethyl-6,7-dihydro-5H-pyrrolo[2,3-d]pyrimidine-2,4-diamine

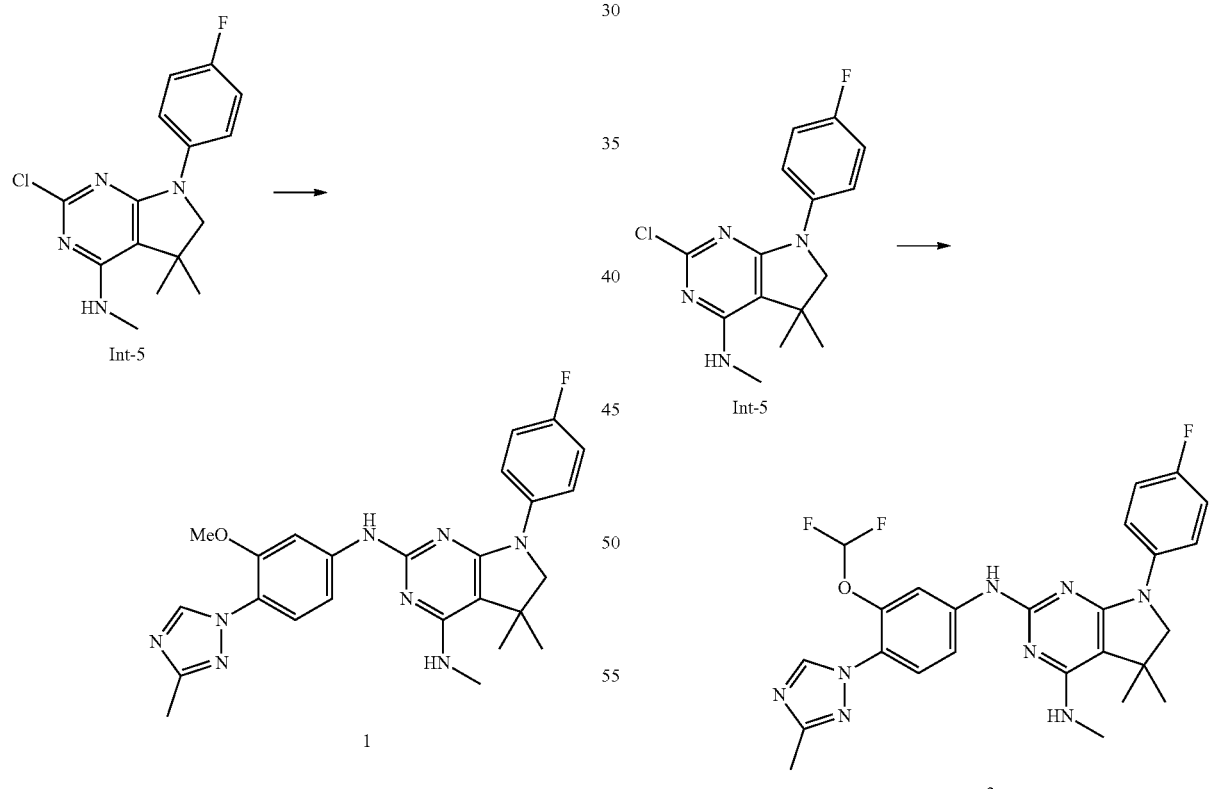

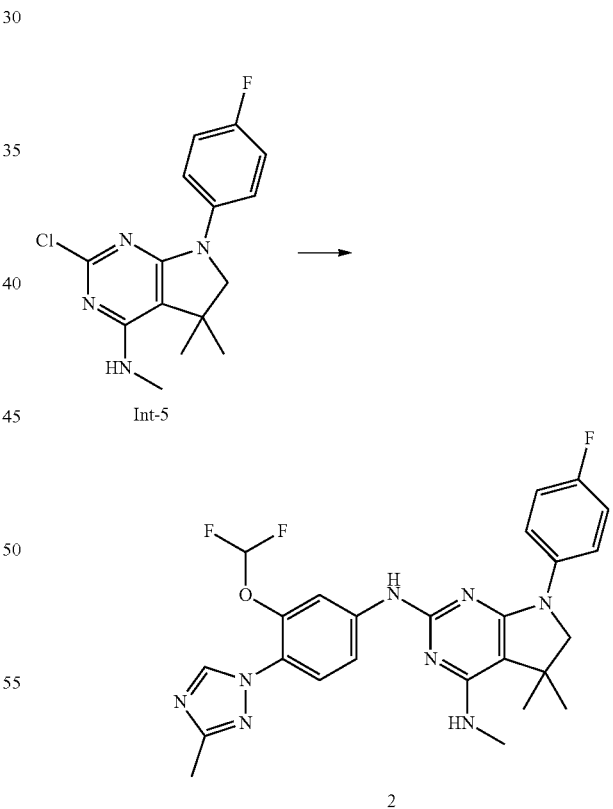

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 70 mg, 228 µmol) was dissolved in NMP (1.5 mL) and 3-methoxy-4-(3-methyl-1H-1,2,4-triazol-1-yl)aniline (56 mg, 274 µmol), cesium carbonate (149 mg, 456 µmol), 2-dicyclohexylphosphino-2'-(N,N-dimethylamino)biphenyl (18 mg, 45.6 µmol), and bis(dibenzylideneacetone)palladium(0) (24 mg, 41.7 µmol) were added subsequently.

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 55 mg, 179 µmol) was dissolved in NMP (1.2 mL) and 3-(difluoromethoxy)-4-(3-methyl-1H-1,2,4-triazol-1-yl)aniline (52 mg, 216 µmol), cesium carbonate (117 mg, 359 µmol), 2-dicyclohexylphosphino-2'-(N,N-dimethylamino)biphenyl (15 mg, 38 µmol), and bis(dibenzylideneacetone)palladium(0) (19 mg, 33 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as a light yellow foam (71 mg, 78%). HPLC (method LCMS_fastgradient) $t_R$=1.38 min. $^1$H NMR (CDCl$_3$, 300 MHz): δ 1.43 (s, 6H), 2.50 (s, 3H), 3.11 (d, J=4.8 Hz, 3H), 3.68 (s, 2H), 4.22-4.30 (m, 1H), 6.49 (t, J=73.1 Hz, 1H), 7.02 (s, 1H), 7.06 (dd, J=8.4, 9.2 Hz, 2H), 7.24 (dd, J=2.3, 8.8 Hz, 1H), 7.57 (d, J=8.9 Hz, 1H), 7.60 (dd, J=4.6, 9.3 Hz, 2H), 8.21-8.25 (m, 1H), 8.40 (s, 1H). MS (ES+) m/z 511.2 [M+H].

Example 3

N2-(3-Fluoro-4-(3-methyl-1H-1,2,4-triazol-1-yl)phenyl)-7-(4-fluorophenyl)-N4,5,5-trimethyl-6,7-dihydro-5H-pyrrolo[2,3-d]pyrimidine-2,4-diamine

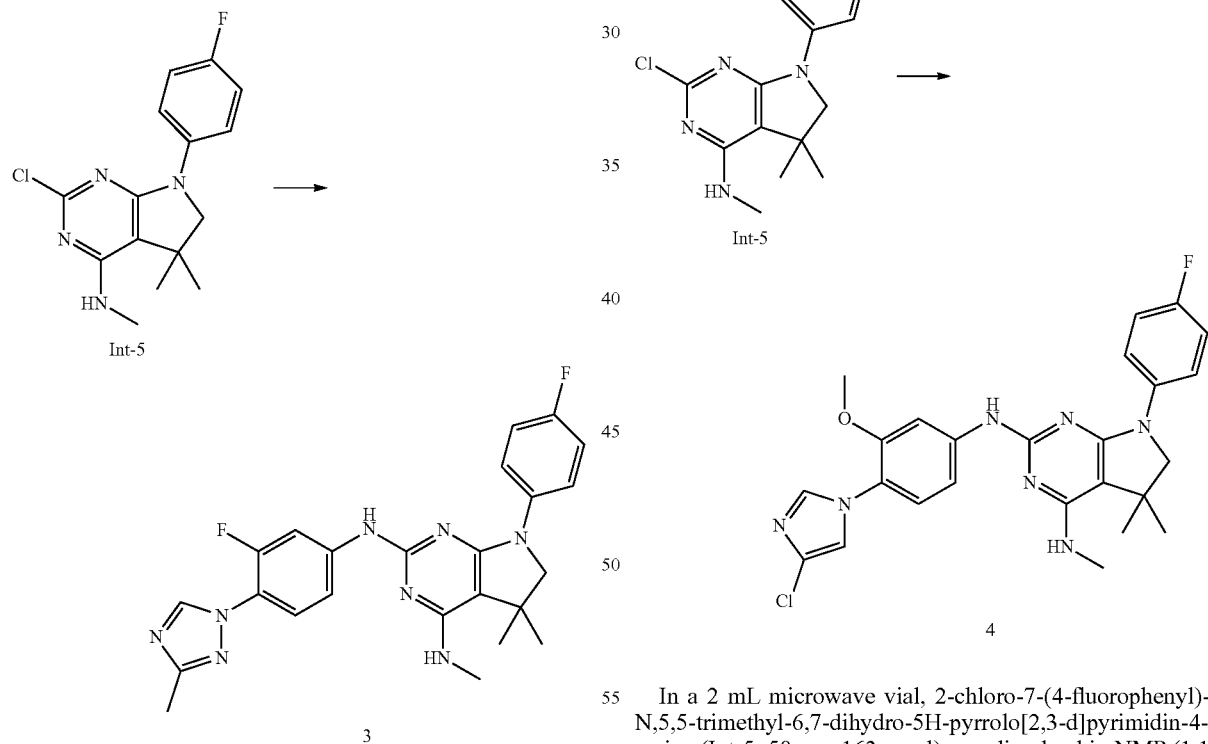

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 45 mg, 147 µmol) was dissolved in NMP (1.0 mL) and 3-fluoro-4-(3-methyl-1H-1,2,4-triazol-1-yl)aniline (34 mg, 177 µmol), cesium carbonate (100 mg, 307 µmol), 2-dicyclohexylphosphino-2'-(N,N-dimethylamino)biphenyl (12 mg, 31 µmol), and bis(dibenzylideneacetone)palladium (0) (16 mg, 28 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as a light yellow foam (31 mg, 46%). HPLC (method LCMS_fastgradient) $t_R$=1.33 min. $^1$H NMR (CDCl$_3$, 300 MHz): δ 1.43 (s, 6H), 2.51 (s, 3H), 3.11 (d, J=4.8 Hz, 3H), 3.68 (s, 2H), 4.21-4.28 (m, 1H), 7.00 (br s, 1H), 7.07 (dd, J=8.4, 9.2 Hz, 2H), 7.18 (ddd, J=1.1, 2.4, 8.9 Hz, 1H), 7.57-7.68 (m, 3H), 8.18 (dd, J=2.2, 14.7 Hz, 1H), 8.44 (d, J=2.4 Hz, 1H). MS (ES+) m/z 463.4 [M+H].

Example 4

N2-(4-(4-Chloro-1H-imidazol-1-yl)-3-methoxyphenyl)-7-(4-fluorophenyl)-N4,5,5-trimethyl-6,7-dihydro-5H-pyrrolo[2,3-d]pyrimidine-2,4-diamine

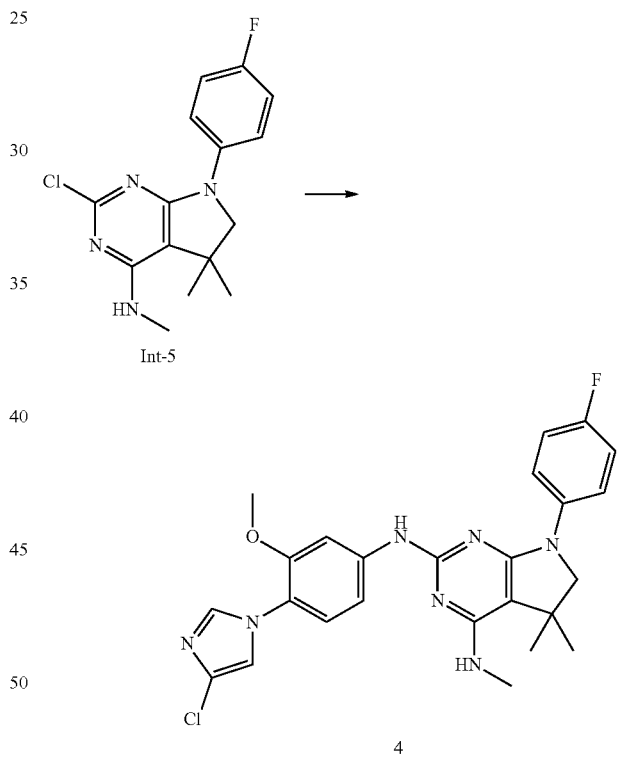

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 50 mg, 163 µmol) was dissolved in NMP (1.1 mL) and 4-(4-chloro-1H-imidazol-1-yl)-3-methoxyaniline (44 mg, 197 µmol), cesium carbonate (110 mg, 338 µmol), 2-dicyclohexylphosphino-2'-(N,N-dimethylamino)biphenyl (13 mg, 33 µmol), and bis(dibenzylideneacetone)palladium (0) (17 mg, 30 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with ethylacetate/n-heptane, gradient 0:100 to 50:50) to afford the title compound as an off-white foam (46 mg, 54%). HPLC (method LCMS_fastgradient) $t_R$=1.40 min. $^1$H NMR (CDCl$_3$, 300 MHz): δ 1.43 (s, 6H), 3.12 (d, J=4.8 Hz, 3H), 3.68 (s, 2H), 3.79 (s, 3H), 4.20-4.28 (m, 1H), 6.96 (br s, 1H), 6.99-7.15 (m, 5H), 7.55 (d, J=1.4 Hz, 1H), 7.61 (dd, J=4.8, 9.3 Hz, 2H), 7.85 (d, J=2.0 Hz, 1H). MS (ES+) m/z 494.3 & 496.2 [M+H, Cl isotopes].

Example 5

N2-(3-Fluoro-4-(5-methyl-1H-1,2,4-triazol-1-yl)phenyl)-7-(4-fluorophenyl)-N4,5,5-trimethyl-6,7-dihydro-5H-pyrrolo[2,3-d]pyrimidine-2,4-diamine

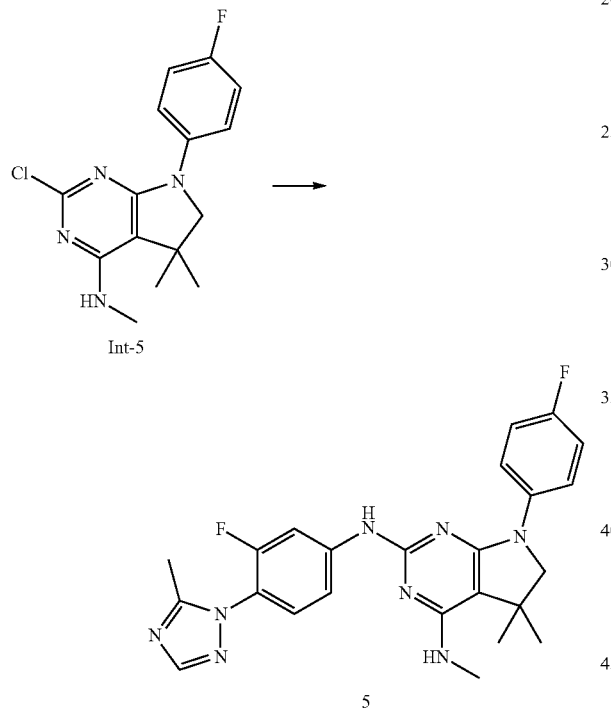

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 50 mg, 163 µmol) was dissolved in NMP (1.1 mL) and 3-fluoro-4-(5-methyl-1H-1,2,4-triazol-1-yl)aniline (38 mg, 198 µmol), cesium carbonate (110 mg, 338 µmol), 2-dicyclohexylphosphino-2'-(N,N-dimethylamino)biphenyl (13 mg, 33 µmol), and bis(dibenzylideneacetone)palladium(0) (17 mg, 30 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethylacetate/n-heptane, gradient 0:100 to 70:30) to afford the title compound as a light yellow solid (51 mg, 68%). HPLC (method LCMS_fastgradient) $t_R$=1.29 min. $^1$H NMR (CDCl$_3$, 300 MHz): δ 1.43 (s, 6H), 2.43 (d, J=1.4 Hz, 3H), 3.11 (d, J=4.8 Hz, 3H), 3.69 (s, 2H), 4.22-4.29 (m, 1H), 7.02-7.11 (m, 1H), 7.18 (ddd, J=0.7, 2.2, 8.7 Hz, 1H), 7.29 (dd, J=8.4, 8.4 Hz, 1H), 7.61 (dd, J=4.6, 9.3 Hz, 2H), 7.97 (s, 1H), 8.19 (dd, J=2.2, 13.5 Hz, 1H). MS (ES+) m/z 463.4 [M+H].

Example 6

N2-(6-(4-Chloro-1H-imidazol-1-yl)-5-methoxypyridin-3-yl)-7-(4-fluorophenyl)-N4,5,5-trimethyl-6,7-dihydro-5H-pyrrolo[2,3-d]pyrimidine-2,4-diamine

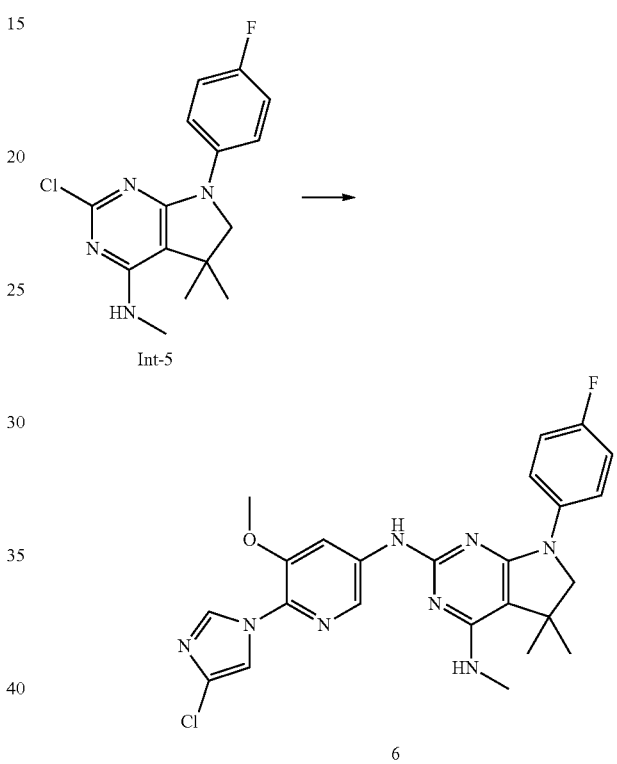

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 60 mg, 196 µmol) was dissolved in NMP (1.3 mL) and 6-(4-chloro-1H-imidazol-1-yl)-5-methoxypyridin-3-amine (53 mg, 236 µmol), cesium carbonate (140 mg, 430 µmol), 2-dicyclohexylphosphino-2'-(N,N-dimethylamino)biphenyl (16 mg, 41 µmol), and bis(dibenzylideneacetone)palladium(0) (21 mg, 36 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with ethylacetate/n-heptane, gradient 0:100 to 50:50) to afford the title compound as a light yellow solid (49 mg, 48%). HPLC (method LCMS_fastgradient) $t_R$=1.45 min. $^1$H NMR (CDCl$_3$, 300 MHz): δ 1.43 (s, 6H), 3.13 (d, J=4.8 Hz, 3H), 3.69 (s, 2H), 3.87 (s, 3H), 4.27 (q, J=4.6 Hz, 1H), 6.99 (s, 1H), 7.06 (dd, J=8.3, 9.1 Hz, 2H), 7.59 (dd, J=4.8, 9.3 Hz, 2H), 7.62 (d, J=1.6 Hz, 1H), 7.99 (d, J=2.2 Hz, 1H), 8.17 (d, J=1.4 Hz, 1H), 8.43 (d, J=2.2 Hz, 1H). MS (ES+) m/z 495.1 & 497.1 [M+H, Cl isotopes].

Example 7

7-(4-Fluorophenyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine

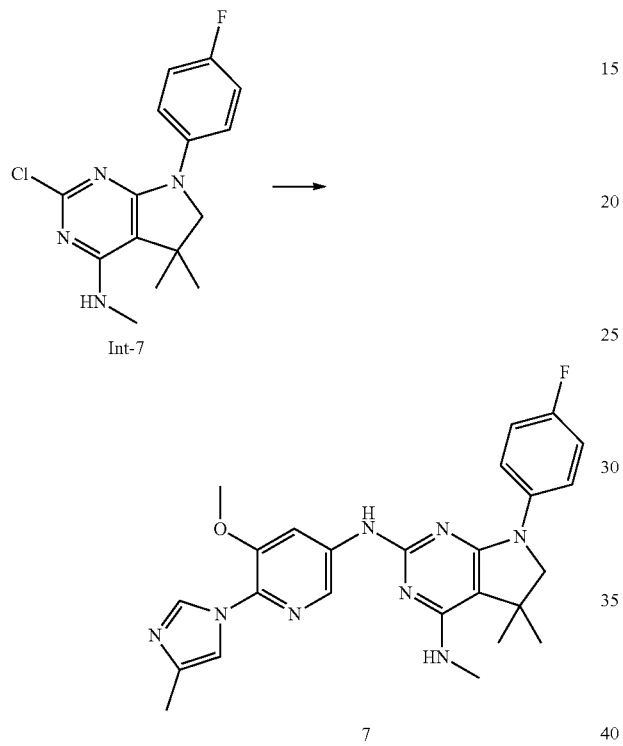

Int-7

7

Example 8

7-(3,4-Difluorophenyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine

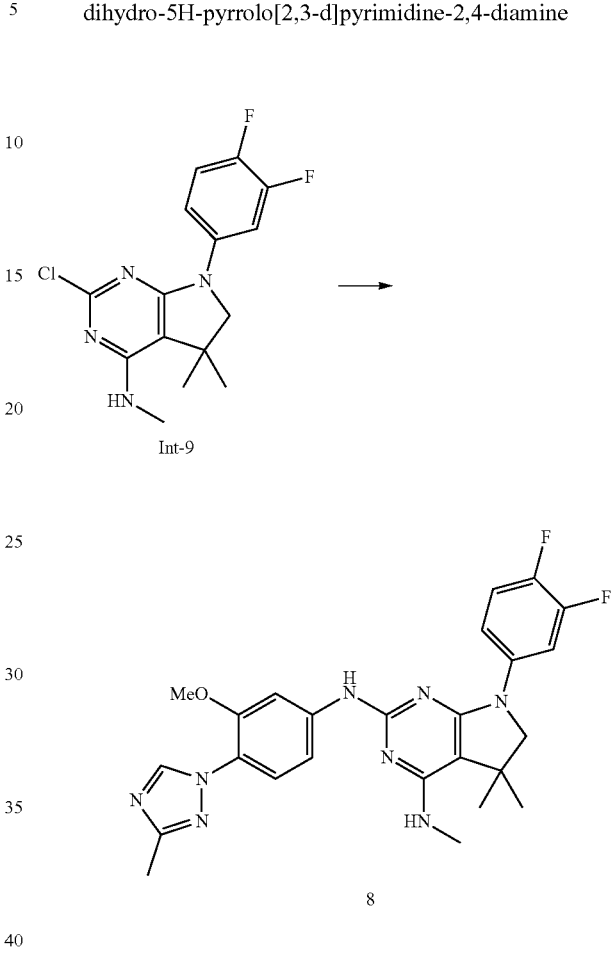

Int-9

8

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 60 mg, 196 μmol) was dissolved in NMP (1.3 mL) and 5-methoxy-6-(4-methyl-1H-imidazol-1-yl)pyridin-3-amine (48 mg, 235 μmol), cesium carbonate (140 mg, 430 μmol), 2-dicyclohexylphosphino-2'-(N,N-dimethylamino)biphenyl (16 mg, 41 μmol), and bis(dibenzylideneacetone)palladium(0) (21 mg, 36 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to yield the title compound as a light yellow solid (33 mg, 34%). HPLC (method LCMS_fastgradient) $t_R$=0.99 min. $^1$H NMR (CDCl$_3$, 300 MHz): 1.43 (s, 6H), 2.31 (d, J=1.0 Hz, 3H), 3.12 (d, J=4.8 Hz, 3H), 3.68 (s, 2H), 3.86 (s, 3H), 4.22-4.30 (m, 1H), 6.96 (s, 1H), 7.06 (dd, J=8.3, 9.3 Hz, 2H), 7.38-7.41 (m, 1H), 7.60 (dd, J=4.7, 9.2 Hz, 2H), 8.00 (d, J=2.2 Hz, 1H), 8.19 (d, J=1.2 Hz, 1H), 8.37 (d, J=2.2 Hz, 1H). MS (ES+) m/z 475.3 [M+H].

In a 2 mL microwave vial, 2-chloro-7-(3,4-difluorophenyl)-N,5,5-trimethyl-6,7-dihydro-5H-pyrrolo[2,3-d]pyrimidin-4-amine (Int-9, 60 mg, 185 μmol) was dissolved in NMP (1.2 mL) and 3-methoxy-4-(3-methyl-1H-1,2,4-triazol-1-yl)aniline (44 mg, 215 μmol), cesium carbonate (125 mg, 384 μmol), 2-dicyclohexylphosphino-2'-(N,N-dimethylamino)biphenyl (15 mg, 38 μmol), and bis(dibenzylideneacetone)palladium(0) (19 mg, 33 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 80:20) to afford the title compound as a light yellow solid (56 mg, 61%). HPLC (method LCMS_fastgradient) $t_R$=1.37 min. $^1$H NMR (CDCl$_3$, 300 MHz): δ 1.42 (s, 6H), 2.50 (s, 3 H), 3.12 (d, J=4.8 Hz, 3H), 3.65 (s, 2H), 3.88 (s, 3H), 4.22-4.30 (m, 1H), 6.98 (s, 1H), 7.06-7.23 (m, 3H), 7.58 (d, J=8.7 Hz, 1H), 7.81 (d, J=2.2 Hz, 1H), 7.86 (ddd, J=2.6, 7.2, 13.5 Hz, 1H), 7.89 (s, 1H). MS (ES+) m/z 493.3 [M+H].

Example 9

7-(3,4-Difluorophenyl)-N2-(3-fluoro-4-(3-methyl-1H-1,2,4-triazol-1-yl)phenyl)-N4,5,5-trimethyl-6,7-dihydro-5H-pyrrolo[2,3-d]pyrimidine-2,4-diamine

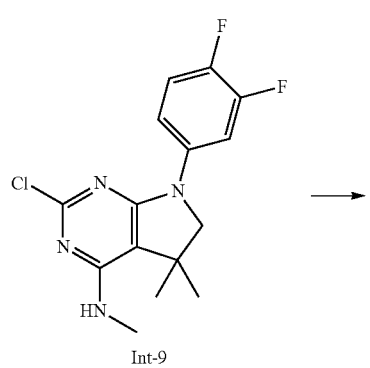

Int-9

Example 10

7-(4-Fluorophenyl)-N4,5,5-trimethyl-N2-(4-(3-methyl-1H-1,2,4-triazol-1-yl)phenyl)-6,7-dihydro-5H-pyrrolo[2,3-d]pyrimidine-2,4-diamine

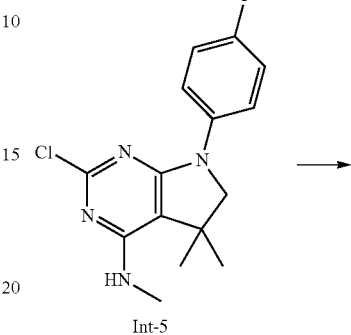

Int-5

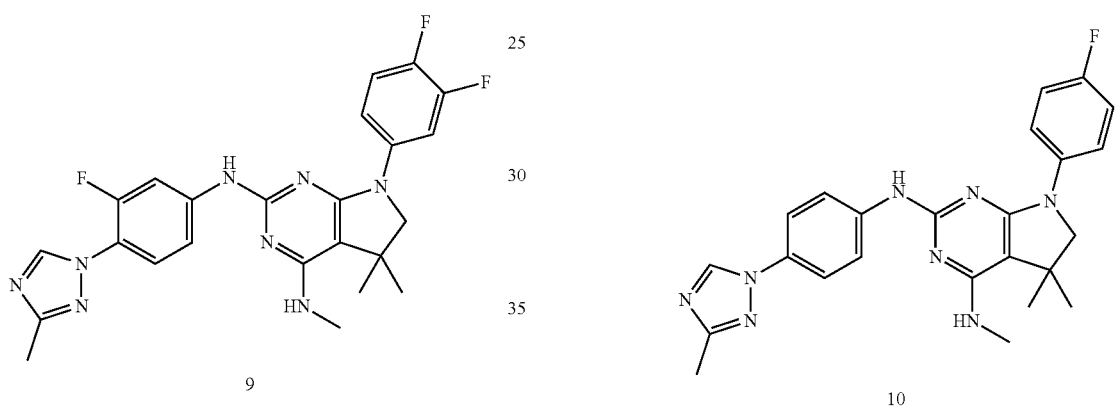

9                                                                                          10

In a 2 mL microwave vial, 2-chloro-7-(3,4-difluorophenyl)-N,5,5-trimethyl-6,7-dihydro-5H-pyrrolo[2,3-d]pyrimidin-4-amine (Int-9, 50 mg, 154 μmol) was dissolved in NMP (1.0 mL) and 3-fluoro-4-(3-methyl-1H-1,2,4-triazol-1-yl)aniline (36 mg, 187 μmol), cesium carbonate (110 mg, 338 μmol), 2-dicyclohexylphosphino-2'-(N,N-dimethylamino)biphenyl (12 mg, 30.5 μmol), and bis(dibenzylideneacetone)palladium(0) (16 mg, 27.8 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 50:50) to yield the title compound as a light yellow solid (33 mg, 45%). HPLC (method LCMS_fastgradient) $t_R$=1.43 min. $^1$H NMR (CDCl$_3$, 300 MHz): δ 1.43 (s, 6H), 2.51 (s, 3H), 3.11 (d, J=4.8 Hz, 3H), 3.65 (s, 2H), 4.24-4.31 (m, 1H), 7.03 (s, 1H), 7.08-7.25 (m, 3H), 7.67 (dd, J=8.8, 8.8 Hz, 1H), 7.81 (ddd, J=2.4, 7.1, 13.4 Hz, 1H), 8.13 (dd, J=2.2, 14.5 Hz, 1H), 8.44 (d, J=2.6 Hz, 1H). MS (ES+) m/z 481.4 [M+H].

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 60 mg, 196 μmol) was dissolved in NMP (1.3 mL) and 4-(3-methyl-1H-1,2,4-triazol-1-yl)aniline (41 mg, 235 μmol), cesium carbonate (140 mg, 430 μmol), 2-dicyclohexylphosphino-2'-(N,N-dimethylamino)biphenyl (16 mg, 41 μmol), and bis(dibenzylideneacetone)palladium(0) (20 mg, 35 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 70:30) to afford the title compound as a light yellow solid (49 mg, 53%). HPLC (method LCMS_fastgradient) $t_R$=1.03 min. $^1$H NMR (CDCl$_3$, 300 MHz): δ 1.42 (s, 6H), 2.51 (s, 3H), 3.10 (d, J=4.8 Hz, 3H), 3.67 (s, 2H), 4.21 (q, J=4.8 Hz, 1H), 6.94 (s, 1H), 7.06 (dd, J=8.4, 9.2 Hz, 2H), 7.53 (d, J=9.1 Hz, 2H), 7.63 (dd, J=4.6, 9.3 Hz, 2H), 7.80 (d, J=8.9 Hz, 2H), 8.36 (s, 1H). MS (ES+) m/z 445.2 [M+H].

Example 11

N2-(4-(2,4-Dimethyl-1H-imidazol-1-yl)-3-fluorophenyl)-7-(4-fluorophenyl)-N4,5,5-trimethyl-6,7-dihydro-5H-pyrrolo[2,3-d]pyrimidine-2,4-diamine

Example 12

7-(4-Fluorophenyl)-N4,5,5-trimethyl-N2-(4-(4-methyl-1H-imidazol-1-yl)phenyl)-6,7-dihydro-5H-pyrrolo[2,3-d]pyrimidine-2,4-diamine

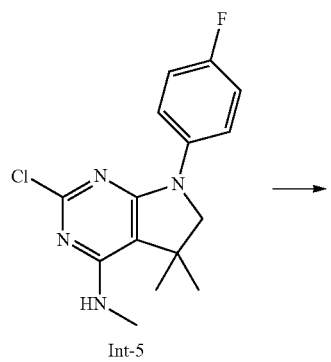

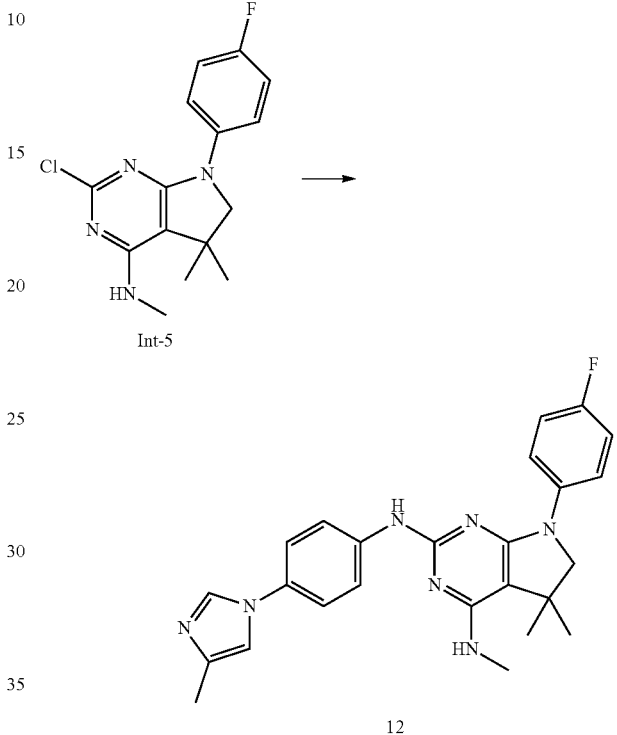

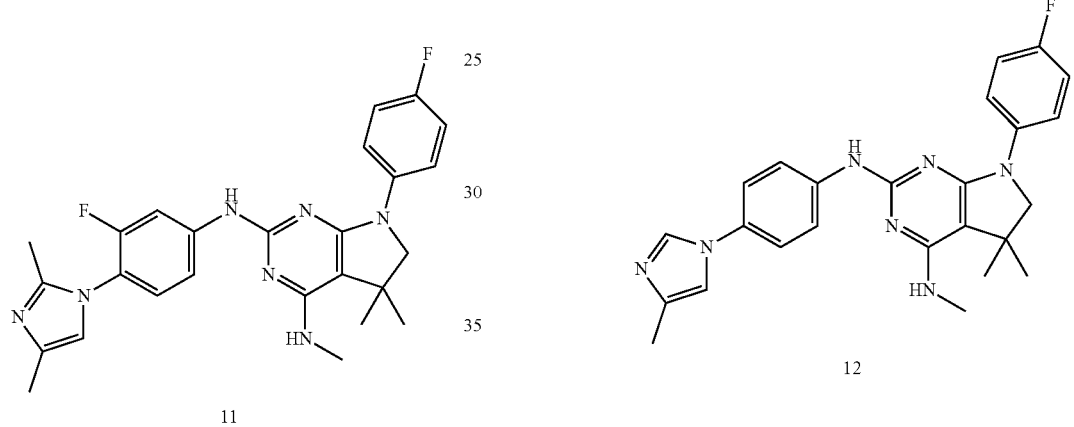

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 60 mg, 196 µmol) was dissolved in NMP (1.3 mL) and 6-(2,4-dimethyl-1H-imidazol-1-yl)-3-fluoroaniline (48 mg, 234 µmol), cesium carbonate (140 mg, 430 µmol), 2-dicyclohexylphosphino-2'-(N,N-dimethylamino)biphenyl (16 mg, 41 µmol), and bis(dibenzylideneacetone)palladium(0) (20 mg, 35 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as a light yellow foam (58 mg, 62%). HPLC (method LCMS_fastgradient) $t_R$=0.97 min. $^1$H NMR (CDCl$_3$, 300 MHz): δ 1.43 (s, 6H), 2.25 (d, J=1.0 Hz, 3H), 2.27 (d, J=0.8 Hz, 3H), 3.11 (d, J=4.8 Hz, 3H), 3.68 (s, 2H), 4.25 (q, J=4.6 Hz, 1H), 6.66 (s, 1H), 7.01 (s, 1H), 7.06 (dd, J=8.4, 9.2 Hz, 2H), 7.11-7.15 (m, 2H), 7.61 (dd, J=4.6, 9.3 Hz, 2H), 8.08-8.15 (m, 1H). MS (ES+) m/z 476.3 [M+H].

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 60 mg, 196 µmol) was dissolved in NMP (1.3 mL) and 4-(4-methyl-1H-imidazol-1-yl)aniline (40 mg, 231 µmol), cesium carbonate (140 mg, 430 µmol), 2-dicyclohexylphosphino-2'-(N,N-dimethylamino)biphenyl (16 mg, 41 µmol), and bis(dibenzylidene-acetone)palladium(0) (20 mg, 35 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95). After concentration of product containing fractions in vacuo, the residue (yellow oil) was triturated with TBME (2 mL) and ethyl acetate (drops) to afford, after filtration and drying in vacuo, the title compound as an off-white solid (47 mg, 54%). HPLC (method LCMS_fastgradient) $t_R$=0.85 min. $^1$H NMR (CDCl$_3$, 300 MHz): δ 1.42 (s, 6H), 2.31 (d, J=1.0 Hz, 3H), 3.10 (d, J=5.0 Hz, 3H), 3.67 (s, 2H), 4.21 (q, J=4.8 Hz, 1H), 6.90 (s, 1H), 6.96-6.98 (m, 1H), 7.05 (dd, J=8.4, 9.2 Hz, 2H), 7.24-7.30 (m, 2H), 7.63 (dd, J=4.8, 9.3 Hz, 2H), 7.70 (d, J=1.4 Hz, 1H), 7.73-7.79 (m, 2H). MS (ES+) m/z 444.2 [M+H].

Example 13

7-(4-Fluorophenyl)-N4,5,5-trimethyl-N2-(6-(3-methyl-1H-1,2,4-triazol-1-yl)pyridin-3-yl)-6,7-dihydro-5H-pyrrolo[2,3-d]pyrimidine-2,4-diamine

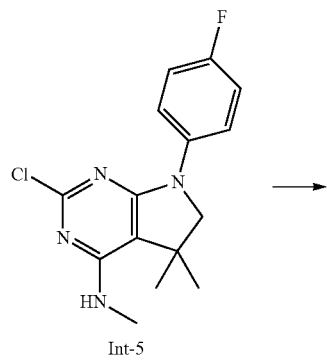

Int-5

→

13

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 60 mg, 196 μmol) was dissolved in NMP (1.3 mL) and 6-(3-methyl-1H-1,2,4-triazol-1-yl)pyridin-3-amine (41 mg, 234 μmol), cesium carbonate (140 mg, 430 μmol), 2-dicyclohexylphosphino-2'-(N,N-dimethylamino)biphenyl (16 mg, 41 μmol), and bis(dibenzylideneacetone)palladium (0) (20 mg, 35 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 70:30) to afford the title compound as a light yellow solid (61 mg, 66%). HPLC (method LCMS_fastgradient) $t_R$=1.11 min. $^1$H NMR (CDCl$_3$, 300 MHz): δ 1.43 (s, 6H), 2.83 (s, 3H), 3.10 (d, J=4.8 Hz, 3H), 3.68 (s, 2H), 4.25 (q, J=4.8 Hz, 1H), 6.97 (s, 1H), 7.06 (dd, J=8.3, 9.3 Hz, 2H), 7.61 (dd, J=4.8, 9.3 Hz, 2H), 7.72 (d, J=8.9 Hz, 1H), 7.91 (s, 1H), 8.42 (dd, J=2.8, 8.9 Hz, 1H), 8.63 (dd, J=0.6, 2.6 Hz, 1H). MS (ES+) m/z 446.3 [M+H].

Example 14

N2-(6-(4-Chloro-1H-imidazol-1-yl)-5-methoxypyridin-3-yl)-7-(3,4-difluorophenyl)-N4,5,5-trimethyl-6,7-dihydro-5H-pyrrolo[2,3-d]pyrimidine-2,4-diamine

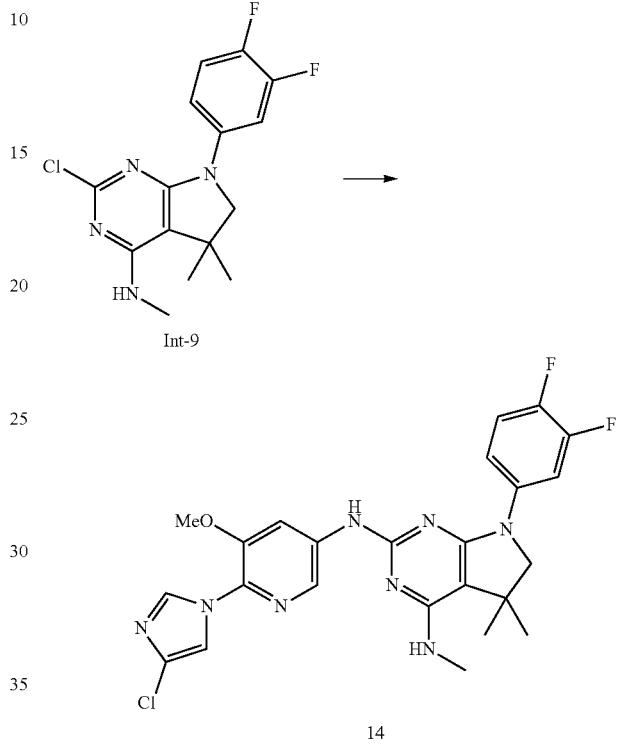

14

In a 2 mL microwave vial, 2-chloro-7-(3,4-difluorophenyl)-N,5,5-trimethyl-6,7-dihydro-5H-pyrrolo[2,3-d]pyrimidin-4-amine (Int-9, 60 mg, 185 μmol) was dissolved in NMP (1.2 mL) and 6-(4-chloro-1H-imidazol-1-yl)-5-methoxypyridine-3-amine (50 mg, 223 μmol), cesium carbonate (130 mg, 399 μmol), 2-dicyclohexylphosphino-2'-(N,N-dimethylamino)biphenyl (15 mg, 38 μmol), and bis(dibenzylideneacetone)palladium(0) (19 mg, 33 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 60:40) to afford the title compound as a light brown solid (53 mg, 56%). HPLC (method LCMS_fastgradient) $t_R$=1.47 min. $^1$H NMR (CDCl$_3$, 300 MHz): δ 1.44 (s, 6H), 3.14 (d, J=4.8 Hz, 3H), 3.67 (s, 2H), 3.89 (s, 3H), 4.28-4.36 (m, 1H), 7.05 (s, 1H), 7.07-7.20 (m, 2H), 7.63 (d, J=1.6 Hz, 1H), 7.79-7.89 (m, 1H), 8.06 (d, J=2.2 Hz, 1H), 8.18 (d, J=1.4 Hz, 1H), 8.36 (d, J=2.0 Hz, 1H). MS (ES+) m/z 513.2 & 515.3 [M+H, Cl isotopes].

Example 15

7-(3,4-Difluorophenyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine

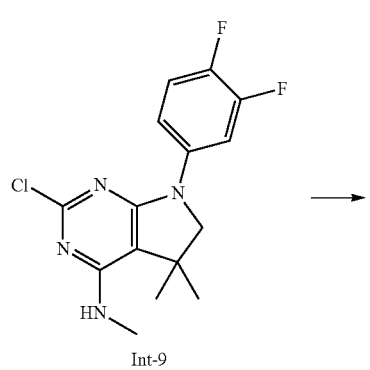

Int-9

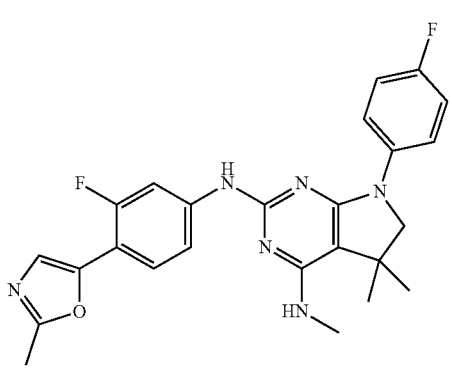

15

In a 2 mL microwave vial, 2-chloro-7-(3,4-difluorophenyl)-N,5,5-trimethyl-6,7-dihydro-5H-pyrrolo[2,3-d]pyrimidin-4-amine (Int-9, 60 mg, 185 μmol) was dissolved in NMP (1.2 mL) and 5-methoxy-6-(4-methyl-1H-imidazol-1-yl)pyridin-3-amine (45 mg, 220 μmol), cesium carbonate (130 mg, 399 μmol), 2-dicyclohexylphosphino-2'-(N,N-dimethylamino)biphenyl (15 mg, 38 μmol), and bis(dibenzylideneacetone)palladium(0) (19 mg, 33 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to yield the title compound as a light yellow solid (73 mg, 76%). HPLC (method LCMS_fastgradient) $t_R$=1.06 min. $^1$H NMR (CDCl$_3$, 300 MHz): δ 1.43 (s, 6H), 2.31 (d, J=1.0 Hz, 3H), 3.13 (d, J=4.8 Hz, 3H), 3.66 (s, 2H), 3.90 (s, 3H), 4.27-4.35 (m, 1H), 7.04 (s, 1H), 7.06-7.21 (m, 2H), 7.40-7.42 (m, 1H), 7.84 (ddd, J=2.6, 7.2, 13.4 Hz, 1H), 8.06 (d, J=2.2 Hz, 1H), 8.20 (d, J=1.2 Hz, 1H), 8.31 (d, J=2.2 Hz, 1H). MS (ES+) m/z 493.2 [M+H].

Example 16

N2-(3-Fluoro-4-(2-methyloxazol-5-yl)phenyl)-7-(4-fluorophenyl)-N4,5,5-trimethyl-6,7-dihydro-5H-pyrrolo[2,3-d]pyrimidine-2,4-diamine

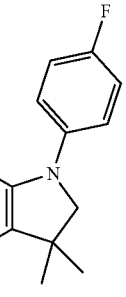

Int-5

16

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 60 mg, 196 μmol) was dissolved in NMP (1.3 mL) and 3-fluoro-4-(2-methyloxazol-5-yl)aniline (45 mg, 234 μmol), cesium carbonate (140 mg, 430 μmol), 2-dicyclohexylphosphino-2'-(N,N-dimethylamino)biphenyl (16 mg, 41 μmol), and bis(dibenzylideneacetone)palladium(0) (20 mg, 35 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 50:50) to afford the title compound as a light yellow foam (59 mg, 65%). HPLC (method LCMS_fastgradient) $t_R$=1.30 min. $^1$H NMR (CDCl$_3$, 300 MHz): δ 1.42 (s, 6H), 2.54 (s, 3H), 3.11 (d, J=4.8 Hz, 3H), 3.67 (s, 2H), 4.19-4.26 (m, 1H), 6.97 (s, 1H), 7.08 (dd, J=8.3, 9.3 Hz, 2H), 7.15 (dd, J=2.1, 8.6 Hz, 1H), 7.24 (d, J=3.8 Hz, 1H), 7.54-7.66 (m, 3H), 8.03 (dd, J=2.0, 14.3 Hz, 1H). MS (ES+) m/z 463.4 [M+H].

Example 17

7-(3,3-Difluorocyclobutyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine

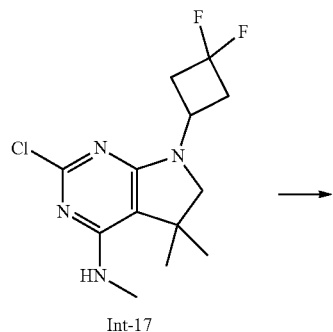

Example 18

7-(3,3-Difluorocyclobutyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine

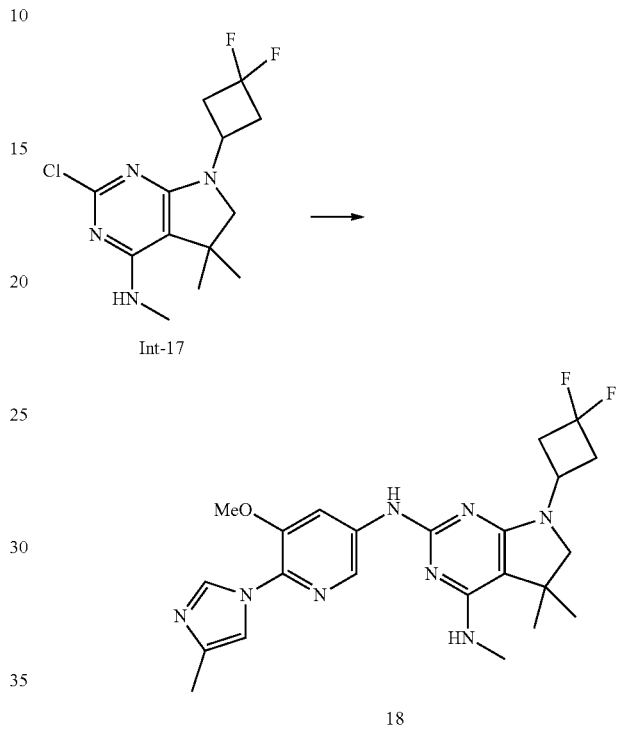

In a 2 mL microwave vial, 2-chloro-7-(3,3-difluorocyclobutyl)-N,5,5-trimethyl-6,7-dihydro-5H-pyrrolo[2,3-d]pyrimidin-4-amine (Int-17, 50 mg, 165 µmol) was dissolved in NMP (1.1 mL) and 3-methoxy-4-(3-methyl-1H-1,2,4-triazol-1-yl)aniline (41 mg, 201 µmol), cesium carbonate (120 mg, 368 µmol), 2-dicyclohexylphosphino-2'-(N,N-dimethylamino)biphenyl (13 mg, 33 µmol), and bis(dibenzylideneacetone)palladium(0) (17 mg, 30 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 70:30) to yield the title compound as a light yellow foam (50 mg, 64%). HPLC (method LCMS_fastgradient) $t_R$=0.95 min. $^1$H NMR (CDCl$_3$, 300 MHz): δ 1.35 (s, 6H), 2.49 (s, 3H), 2.77-2.91 (m, 4H), 3.07 (d, J=4.8 Hz, 3H), 3.20 (s, 2H), 3.92 (s, 3H), 4.05-4.14 (m, 1H), 4.42-4.57 (m, 1H), 6.90 (s, 1H), 6.99 (dd, J=2.2, 8.7 Hz, 1H), 7.54 (d, J=8.7 Hz, 1H), 7.97 (d, J=2.2 Hz, 1H), 8.48 (s, 1H). MS (ES+) m/z 471.3 [M+H].

In a 2 mL microwave vial, 2-chloro-7-(3,3-difluorocyclobutyl)-N,5,5-trimethyl-6,7-dihydro-5H-pyrrolo[2,3-d]pyrimidin-4-amine (Int-17, 45 mg, 149 µmol) was dissolved in NMP (1.0 mL) and 5-methoxy-6-(4-methyl-1H-imidazol-1-yl)pyridine-3-amine (36 mg, 176 µmol), cesium carbonate (110 mg, 338 µmol), 2-dicyclohexylphosphino-2'-(N,N-dimethylamino)biphenyl (12 mg, 30.5 µmol), and bis(dibenzylideneacetone)palladium(0) (16 mg, 27.8 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to afford, after tritiation with ethyl acetate, the title compound as a light yellow solid (44 mg, 60%). HPLC (method LCMS_fastgradient) $t_R$=0.87 min. $^1$H NMR (CDCl$_3$, 300 MHz): δ 1.35 (s, 6H), 2.30 (d, J=1.0 Hz, 3H), 2.77-2.90 (m, 4H), 3.07 (d, J=5.0 Hz, 3H), 3.22 (s, 2H), 3.96 (s, 3H), 4.09-4.18 (m, 1H), 4.44-4.58 (m, 1H), 6.89 (s, 1H), 7.38-7.41 (m, 1H), 7.99 (d, J=2.2 Hz, 1H), 8.18 (d, J=1.2 Hz, 1H), 8.44 (d, J=2.2 Hz, 1H). MS (ES+) m/z 471.2 [M+H].

Example 19

7-(2,4-Difluorophenyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine

Example 20

7-(2,4-Difluorophenyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine

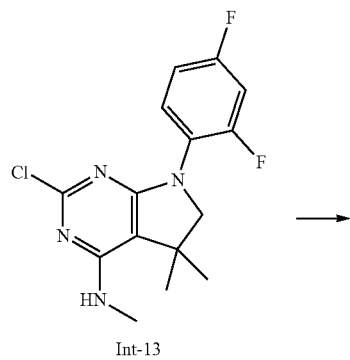

Int-13

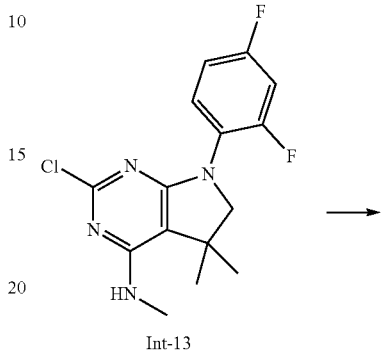

Int-13

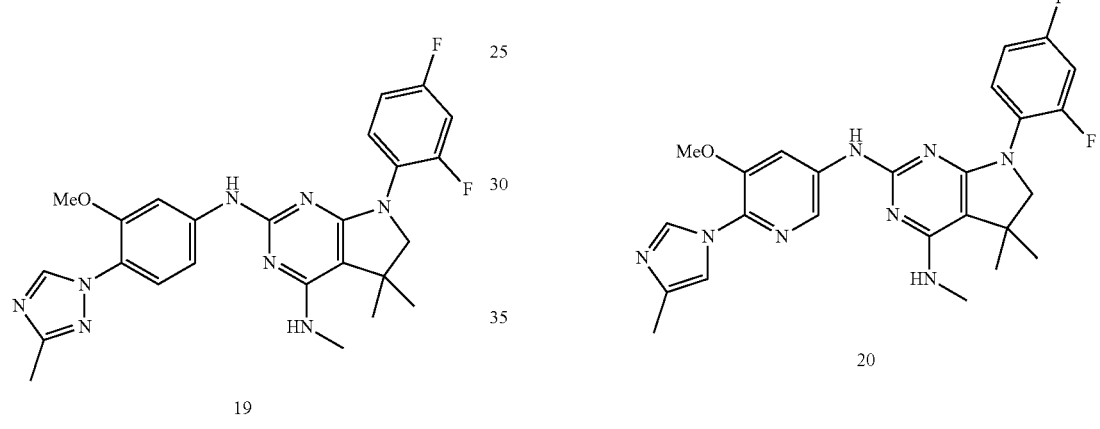

19          20

In a 2 mL microwave vial, 2-chloro-7-(2,4-difluorophenyl)-N,5,5-trimethyl-6,7-dihydro-5H-pyrrolo[2,3-d]pyrimidin-4-amine (Int-13, 55 mg, 169 μmol) was dissolved in NMP (1.1 mL) and 3-methoxy-4-(3-methyl-1H-1,2,4-triazol-1-yl)aniline (41 mg, 201 μmol), cesium carbonate (120 mg, 368 μmol), 2-dicyclohexylphosphino-2'-(N,N-dimethylamino)biphenyl (14 mg, 35.6 μmol), and bis(dibenzylideneacetone)palladium(0) (18 mg, 31.3 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 70:30) to yield the title compound as a light yellow foam (55 mg, 66%). HPLC (method LCMS_fastgradient) $t_R$=1.05 min. $^1$H NMR (CDCl$_3$, 300 MHz): δ 1.42 (s, 6H), 2.48 (s, 3H), 3.11 (d, J=4.8 Hz, 3H), 3.63 (d, J=1.0 Hz, 2H), 3.71 (s, 3H), 4.19-4.26 (m, 1H), 6.85-6.94 (m, 4H), 7.48 (d, J=8.7 Hz, 1H), 7.51-7.60 (m, 1H), 7.90 (d, J=2.2 Hz, 1H), 8.45 (s, 1H). MS (ES+) m/z 493.3 [M+H].

In a 2 mL microwave vial, 2-chloro-7-(2,4-difluorophenyl)-N,5,5-trimethyl-6,7-dihydro-5H-pyrrolo[2,3-d]pyrimidin-4-amine (Int-13, 60 mg, 185 μmol) was dissolved in NMP (1.2 mL) and 5-methoxy-6-(4-methyl-1H-imidazol-1-yl)pyridin-3-amine (45 mg, 220 μmol), cesium carbonate (130 mg, 399 μmol), 2-dicyclohexylphosphino-2'-(N,N-dimethylamino)biphenyl (15 mg, 38 μmol), and bis(dibenzylideneacetone)palladium(0) (19 mg, 33 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to yield the title compound as a light yellow foam (36 mg, 40%). HPLC (method LCMS_fastgradient) $t_R$=0.95 min. $^1$H NMR (CDCl$_3$, 300 MHz): δ 1.43 (s, 6H), 2.29 (d, J=1.0 Hz, 3H), 3.11 (d, J=4.8 Hz, 3H), 3.63 (d, J=0.8 Hz, 2H), 3.72 (s, 3H), 4.22-4.30 (m, 1H), 6.86-6.95 (m, 3H), 7.35-7.37 (m, 1H), 7.47-7.57 (m, 1H), 7.87 (d, J=2.2 Hz, 1H), 8.15 (d, J=1.2 Hz, 1H), 8.38 (d, J=2.2 Hz, 1H). MS (ES+) m/z 493.2 [M+H].

Example 21

N2-(3-Methoxy-4-(3-methyl-1H-1,2,4-triazol-1-yl)phenyl)-N4,5,5-trimethyl-7-(3-(trifluoromethyl)bicyclo[1.1.1]pentan-1-yl)-6,7-dihydro-5H-pyrrolo[2,3-d]pyrimidine-2,4-diamine

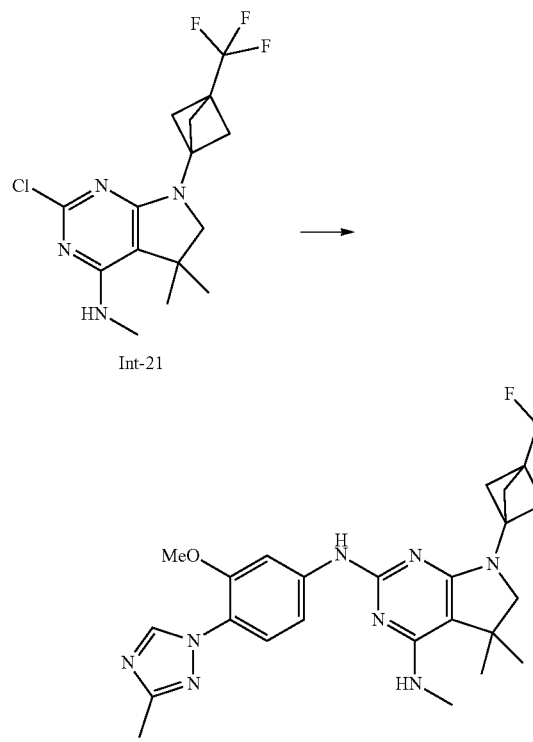

In a 2 mL microwave vial, 2-chloro-N,5,5-trimethyl-7-(3-(trifluoromethyl)-bicyclo[1.1.1]pentan-1-yl)-6,7-dihydro-5H-pyrrolo[2,3-d]pyrimidin-4-amine (Int-21, 60 mg, 173 μmol) was dissolved in NMP (1.2 mL) and 3-methoxy-4-(3-methyl-1H-1,2,4-triazol-1-yl)aniline (42 mg, 206 μmol), cesium carbonate (124 mg, 381 μmol), 2-dicyclohexylphosphino-2'-(N,N-dimethyl-amino)biphenyl (14 mg, 36 μmol), and bis(dibenzylideneacetone)palladium(0) (18 mg, 31 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 70:30) to yield the title compound as a light yellow foam (47 mg, 53%). HPLC (method LCMS_fastgradient) $t_R$=1.17 min. $^1$H NMR (CDCl$_3$, 300 MHz): δ 1.33 (s, 6H), 2.36 (s, 6H), 2.49 (s, 3H), 3.07 (d, J=4.8 Hz, 3H), 3.14 (s, 2H), 3.90 (s, 3H), 4.08-4.15 (m, 1H), 6.95 (s, 1H), 7.11 (dd, J=2.0, 8.7 Hz, 1H), 7.53 (d, J=8.7 Hz, 1H), 7.75 (d, J=2.0 Hz, 1H), 8.47 (s, 1H). MS (ES+) m/z 515.3 [M+H].

Example 22

N2-(5-Methoxy-6-(4-methyl-1H-imidazol-1-yl)pyridin-3-yl)-N4,5,5-trimethyl-7-(3-(trifluoromethyl)bicyclo[1.1.1]pentan-1-yl)-6,7-dihydro-5H-pyrrolo[2,3-d]pyrimidine-2,4-diamine

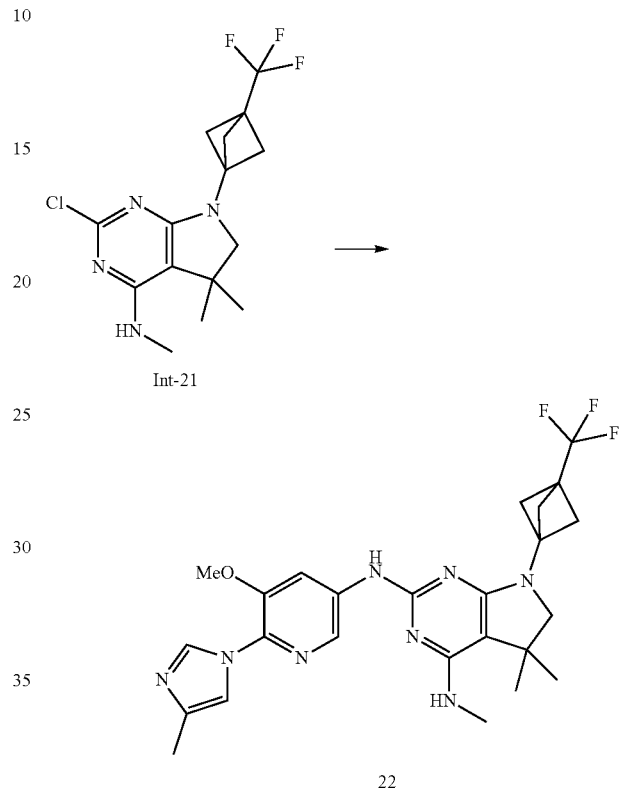

In a 2 mL microwave vial, 2-chloro-N,5,5-trimethyl-7-(3-(trifluoromethyl)-bicyclo[1.1.1]pentan-1-yl)-6,7-dihydro-5H-pyrrolo[2,3-d]pyrimidin-4-amine (Int-21, 60 mg, 173 μmol) was dissolved in NMP (1.2 mL) and 5-methoxy-6-(4-methyl-1H-imidazol-1-yl)pyridine-3-amine (42 mg, 206 μmol), cesium carbonate (124 mg, 381 μmol), 2-dicyclohexylphosphino-2'-(N,N-dimethylamino)biphenyl (14 mg, 36 μmol), and bis(dibenzylideneacetone)palladium(0) (18 mg, 31 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to afford the title compound as an off-white solid (64 mg, 72%). HPLC (method LCMS_fastgradient) $t_R$=1.10 min. $^1$H NMR (CDCl$_3$, 300 MHz): δ 1.34 (s, 6H), 2.30 (d, J=1.0 Hz, 3H), 2.36 (s, 6H), 3.08 (d, J=4.8 Hz, 3H), 3.15 (s, 2H), 3.94 (s, 3H), 4.11-4.19 (m, 1H), 6.93 (s, 1H), 7.38-7.40 (m, 1H), 8.04 (d, J=2.2 Hz, 1H), 8.18 (d, J=1.4 Hz, 1H), 8.29 (d, J=2.2 Hz, 1H). MS (ES+) m/z 515.3 [M+H].

Example 23

N2-(6-(4-Chloro-1H-imidazol-1-yl)-5-methoxypyridin-3-yl)-7-(2,4-difluorophenyl)-N4,5,5-trimethyl-6,7-dihydro-5H-pyrrolo[2,3-d]pyrimidine-2,4-diamine

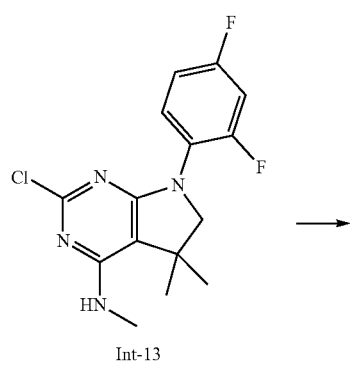

Int-13

Example 24

7-(2,4-Difluorophenyl)-N2-(3-fluoro-4-(3-methyl-1H-1,2,4-triazol-1-yl)phenyl)-N4,5,5-trimethyl-6,7-dihydro-5H-pyrrolo[2,3-d]pyrimidine-2,4-diamine

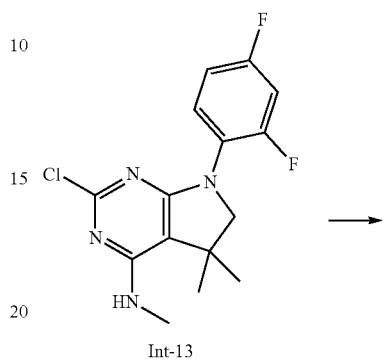

Int-13

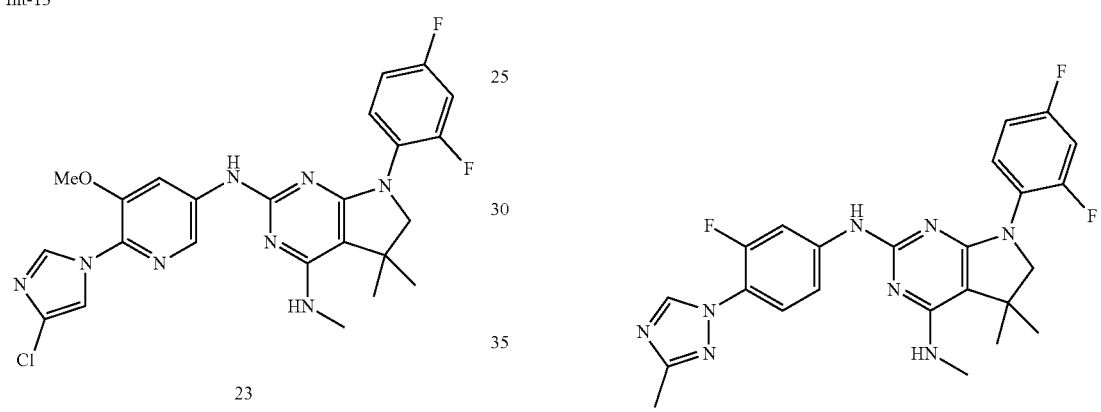

23

24

In a 2 mL microwave vial, 2-chloro-7-(2,4-difluorophenyl)-N,5,5-trimethyl-6,7-dihydro-5H-pyrrolo[2,3-d]pyrimidin-4-amine (Int-13, 60 mg, 185 µmol) was dissolved in NMP (1.2 mL) and 6-(4-chloro-1H-imidazol-1-yl)-5-methoxypyridin-3-amine (50 mg, 223 µmol), cesium carbonate (130 mg, 300 µmol), 2-dicyclohexylphosphino-2'-(N,N-dimethylamino)biphenyl (15 mg, 38 µmol), and bis(dibenzylideneacetone)palladium(0) (19 mg, 33 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with ethyl acetate/n-heptane, gradient 0:100 to 70:30) to yield the title compound as a light yellow foam (58 mg, 58%). HPLC (method LCMS_fastgradient) $t_R$=1.32 min. $^1$H NMR (CDCl$_3$, 300 MHz): δ 1.44 (s, 6H), 3.11 (d, J=4.8 Hz, 3H), 3.64 (d, J=0.8 Hz, 2H), 3.73 (s, 3H), 4.23-4.31 (m, 1H), 6.86-6.99 (m, 3H), 7.46-7.56 (m, 1H), 7.58 (d, J=1.6 Hz, 1H), 7.87 (d, J=2.2 Hz, 1H), 8.13 (d, J=1.6 Hz, 1H), 8.43 (d, J=2.2 Hz, 1H). MS (ES+) m/z 513.3 [M+H].

In a 2 mL microwave vial, 2-chloro-7-(2,4-difluorophenyl)-N,5,5-trimethyl-6,7-dihydro-5H-pyrrolo[2,3-d]pyrimidin-4-amine (Int-13, 50 mg, 154 µmol) was dissolved in NMP (1.1 mL) and 3-fluoro-6-(3-methyl-1H-1,2,4-triazol-1-yl)aniline (32 mg, 166 µmol), cesium carbonate (120 mg, 368 µmol), 2-dicyclohexylphosphino-2'-(N,N-dimethylamino)biphenyl (12 mg, 30.5 µmol), and bis(dibenzylideneacetone)palladium(0) (16 mg, 28 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, ethyl acetate/n-heptane, gradient 0:100 to 60:40) to yield the title compound as a light yellow foam (34 mg, 44%). HPLC (method LCMS_fastgradient) $t_R$=1.19 min. $^1$H NMR (CDCl$_3$, 300 MHz): δ 1.43 (s, 6H), 2.50 (s, 3H), 3.10 (d, J=4.8 Hz, 3H), 3.66 (d, J=1.0 Hz, 2H), 4.21-4.29 (m, 1H), 6.86-6.98 (m, 3H), 7.10 (ddd, J=1.0, 2.4, 8.9 Hz, 1H), 7.51-7.62 (m, 2H), 8.10 (dd, J=2.2, 14.7 Hz, 1H), 8.41 (d, J=2.6 Hz, 1H). MS (ES+) m/z 481.3 [M+H].

Example 25

N2-(5-Fluoro-6-(4-methyl-1H-imidazol-1-yl)pyridin-3-yl)-7-(4-fluorophenyl)-N4,5,5-trimethyl-6,7-dihydro-5H-pyrrolo[2,3-d]pyrimidine-2,4-diamine

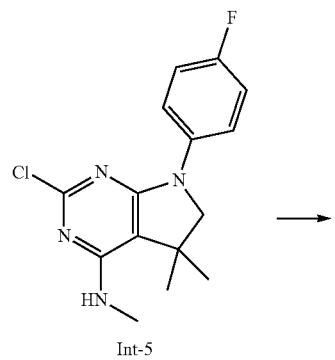

Int-5

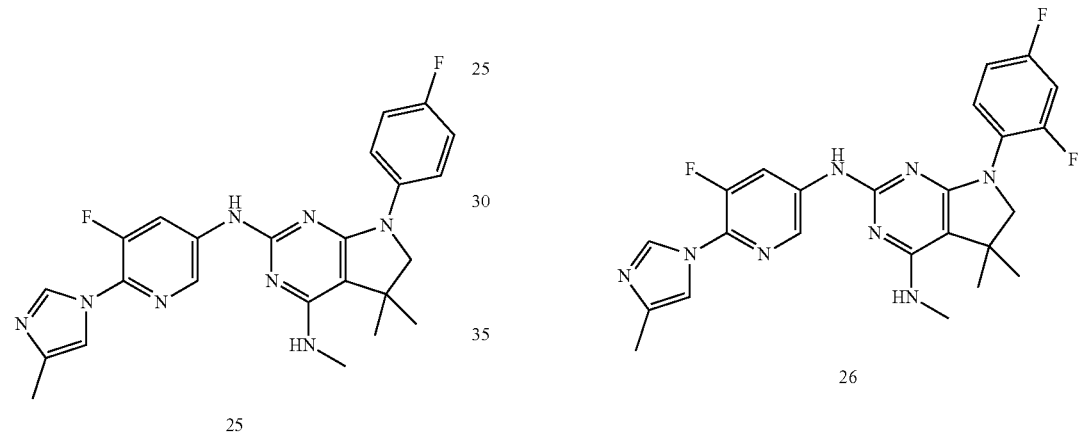

25

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 60 mg, 196 μmol) was dissolved in NMP (1.3 mL) and 5-fluoro-6-(4-methyl-1H-imidazol-1-yl)pyridin-3-amine (45 mg, 234 μmol), cesium carbonate (140 mg, 430 μmol), 2-dicyclohexylphosphino-2'-(N,N-dimethylamino)biphenyl (15 mg, 38 μmol), and bis(dibenzylideneacetone)palladium(0) (20 mg, 35 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to yield the title compound as a light yellow solid (60 mg, 66%). HPLC (method LCMS_fastgradient) $t_R$=1.10 min. $^1$H NMR (CDCl$_3$, 300 MHz): δ 1.43 (s, 6H), 2.32 (d, J=1.0 Hz, 3H), 3.11 (d, J=4.8 Hz, 3H), 3.69 (s, 2H), 4.24-4.31 (m, 1H), 7.02 (s, 1H), 7.08 (dd, J=8.4, 9.2 Hz, 2H), 7.39-7.42 (m, 1H), 7.55-7.63 (m, 2H), 8.16-8.19 (m, 2H), 8.64 (dd, J=2.2, 14.1 Hz, 1H). MS (ES+) m/z 463.3 [M+H].

Example 26

7-(2,4-Difluorophenyl)-N2-(5-fluoro-6-(4-methyl-1H-imidazol-1-yl)pyridin-3-yl)-N4,5,5-trimethyl-6,7-dihydro-5H-pyrrolo[2,3-d]pyrimidine-2,4-diamine

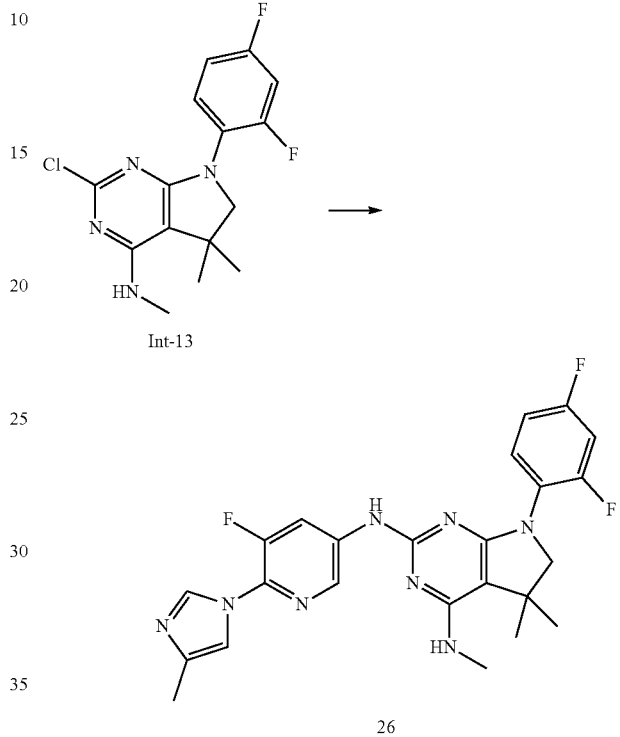

In a 2 mL microwave vial, 2-chloro-7-(2,4-difluorophenyl)-N,5,5-trimethyl-6,7-dihydro-5H-pyrrolo[2,3-d]pyrimidin-4-amine (Int-13, 60 mg, 185 μmol) was dissolved in NMP (1.2 mL) and 5-fluoro-6-(4-methyl-1H-imidazol-1-yl)pyridin-3-amine (42 mg, 219 μmol), cesium carbonate (130 mg, 399 μmol), 2-dicyclohexylphosphino-2'-(N,N-dimethylamino)biphenyl (15 mg, 38 μmol), and bis(dibenzylideneacetone)palladium(0) (19 mg, 33 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to yield the title compound as an off-white solid (45 mg, 51%). HPLC (method LCMS_fastgradient) $t_R$=1.06 min. $^1$H NMR (CDCl$_3$, 300 MHz): δ 1.43 (s, 6H), 2.31 (d, J=1.0 Hz, 3H), 3.10 (d, J=4.8 Hz, 3H), 3.67 (d, J=0.8 Hz, 2H), 4.24-4.32 (m, 1H), 6.87-6.96 (m, 2H), 7.01 (s, 1H), 7.36-7.39 (m, 1H), 7.47-7.56 (m, 1H), 8.08-8.11 (m, 1H), 8.13-8.16 (m, 1H), 8.56 (dd, J=2.2, 14.3 Hz, 1H). MS (ES+) m/z 481.3 [M+H].

Example 27

7-(4-Fluorophenyl)-N2-(3-methoxy-4-(5-methyl-1,3,4-oxadiazol-2-yl)phenyl)-N4,5,5-trimethyl-6,7-dihydro-5H-pyrrolo[2,3-d]pyrimidine-2,4-diamine

Example 28

2-((7-(4-Fluorophenyl)-2-((3-methoxy-4-(3-methyl-1H-1,2,4-triazol-1-yl)phenyl)amino)-5,5-dimethyl-6,7-dihydro-5H-pyrrolo[2,3-d]pyrimidin-4-yl)amino)ethanol

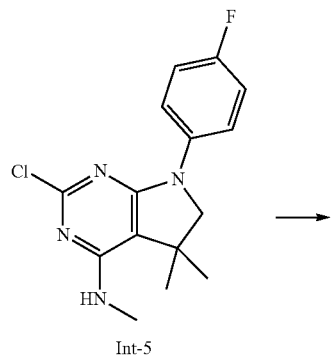

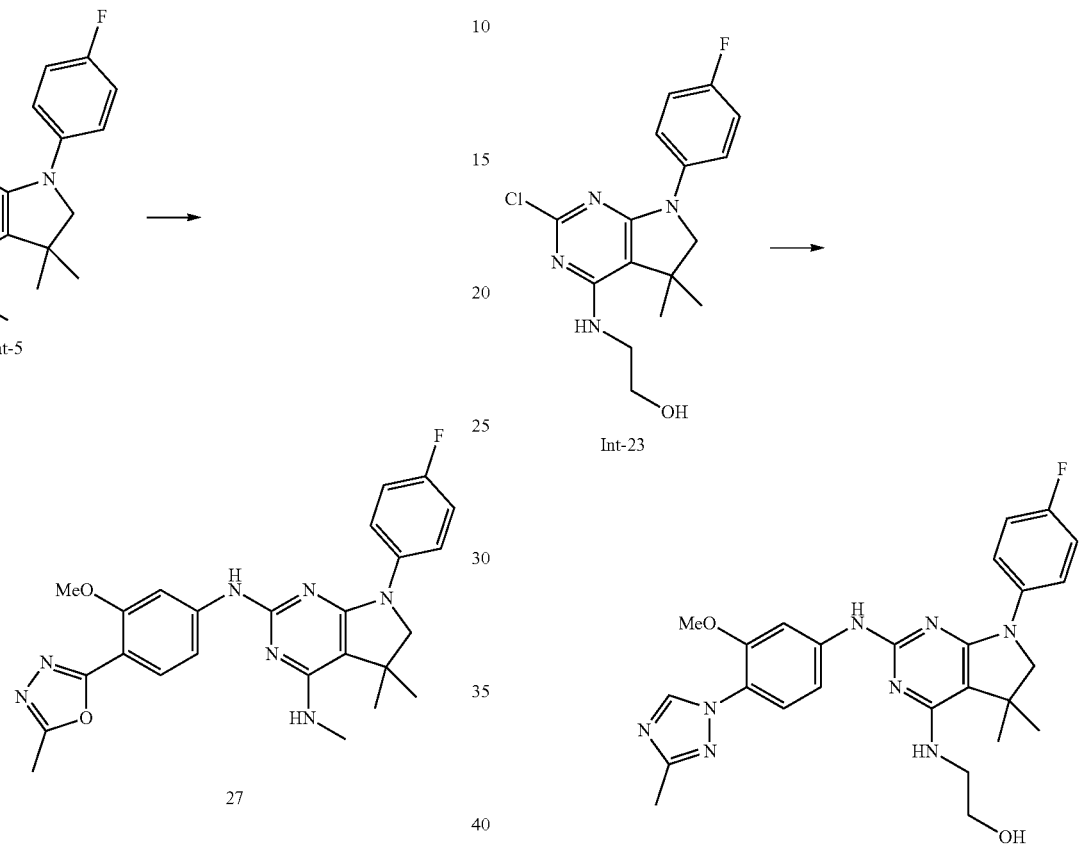

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 60 mg, 196 μmol) was dissolved in NMP (1.3 mL) and 3-methoxy-4-(5-methyl-1,3,4-oxadiazol-2-yl)aniline (48 mg, 234 μmol), cesium carbonate (140 mg, 430 μmol), 2-dicyclohexylphosphino-2'-(N,N-dimethylamino)biphenyl (15 mg, 38 μmol), and bis(dibenzylideneacetone)palladium(0) (20 mg, 35 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, ethyl acetate/n-heptane, gradient 0:100 to 100:0) to afford the title compound as a light yellow foam (66 mg, 67%). HPLC (method LCMS_fastgradient) $t_R$=1.19 min. $^1$H NMR (CDCl$_3$, 300 MHz): δ 1.43 (s, 6H), 2.60 (s, 3H), 3.13 (d, J=4.8 Hz, 3H), 3.68 (s, 2H), 3.92 (s, 3H), 4.21-4.28 (m, 1H), 7.02-7.10 (m, 4H), 7.58-7.65 (m, 2H), 7.79 (d, J=8.7 Hz, 1H), 7.87 (d, J=2.0 Hz, 1H). MS (ES+) m/z 476.3 [M+H].

In a 2 mL microwave vial, 2-((2-chloro-7-(4-fluorophenyl)-5,5-dimethyl-6,7-dihydro-5H-pyrrolo[2,3-d]pyrimidin-4-yl)amino)ethanol (Int-23, 60 mg, 178 μmol) was dissolved in NMP (1.2 mL) and 3-methoxy-4-(3-methyl-1H-1,2,4-triazol-1-yl)aniline (43 mg, 211 μmol), cesium carbonate (130 mg, 399 μmol), 2-dicyclohexylphosphino-2'-(N,N-dimethylamino)biphenyl (14 mg, 36 μmol), and bis(dibenzylideneacetone)palladium(0) (18 mg, 31 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with ethyl acetate/n-heptane, gradient 0:100 to 100:0, followed by methanol/dichloromethane, gradient 0:100 to 10:90) to afford the title compound as a light yellow foam (29 mg, 32%). HPLC (method LCMS_fastgradient) $t_R$=1.07 min. $^1$H NMR (CDCl$_3$, 300 MHz): δ 1.45 (s, 6H), 2.49 (s, 3H), 3.46 (br s, 1H), 3.68-3.75 (m, 2H), 3.70 (s, 2H), 3.79 (s, 3H), 3.82-3.87 (m, 2H), 4.70 (t, J=5.6 Hz, 1H), 6.88

(s, 1H), 7.05 (dd, J=8.4, 9.2 Hz, 2H), 7.08 (dd, J=2.2, 8.7 Hz, 1H), 7.54-7.63 (m, 4H), 8.49 (s, 1H). MS (ES+) m/z 505.4 [M+H].

Example 29

2-((7-(4-Fluorophenyl)-2-((5-methoxy-6-(4-methyl-1H-imidazol-1-yl)pyridin-3-yl)amino)-5,5-dimethyl-6,7-dihydro-5H-pyrrolo[2,3-d]pyrimidin-4-yl)amino)ethanol

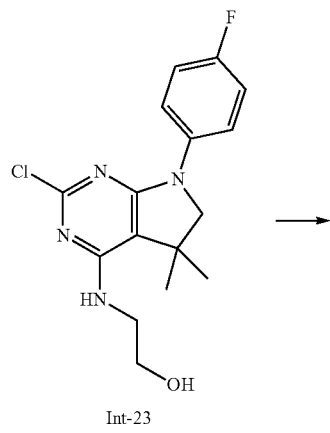

Int-23

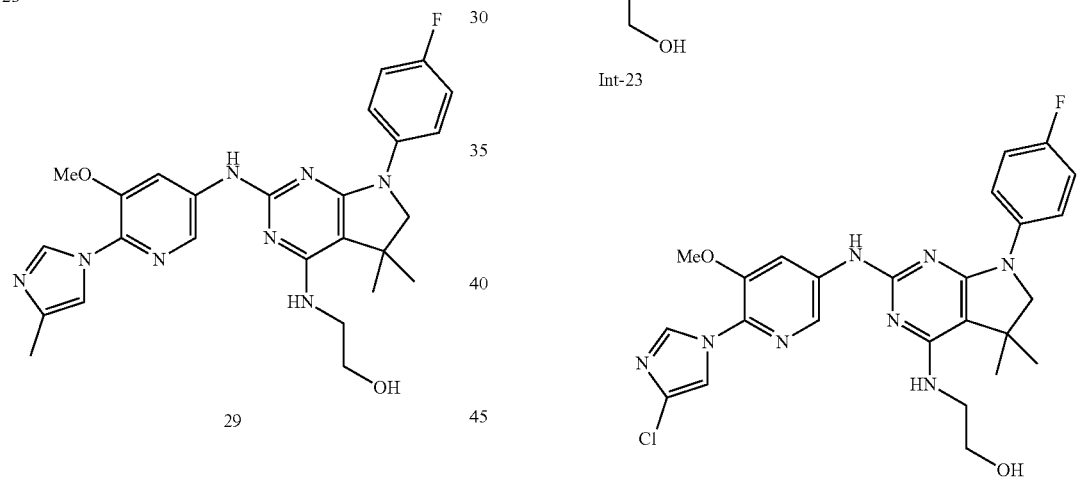

29

In a 2 mL microwave vial, 2-((2-chloro-7-(4-fluorophenyl)-5,5-dimethyl-6,7-dihydro-5H-pyrrolo[2,3-d]pyrimidin-4-yl)amino)ethanol (Int-23, 60 mg, 178 µmol) was dissolved in NMP (1.2 mL) and 5-methoxy-6-(4-methyl-1H-imidazol-1-yl)pyridin-3-amine (43 mg, 211 µmol), cesium carbonate (130 mg, 399 µmol), 2-dicyclohexylphosphino-2'-(N,N-dimethylamino)biphenyl (14 mg, 36 µmol), and bis(dibenzylideneacetone)palladium(0) (18 mg, 31 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95) to yield the title compound as a light yellow foam (34 mg, 36%). HPLC (method LCMS_fastgradient) $t_R$=0.99 min. $^1$H NMR (CDCl$_3$, 300 MHz): δ 1.45 (s, 6H), 2.30 (d, J=1.0 Hz, 3H), 3.39 (br s, 1H), 3.68-3.75 (m, 2H), 3.70 (s, 2H), 3.80 (s, 3H), 3.83-3.89 (m, 2H), 4.73 (t, J=5.6 Hz, 1H), 6.88 (s, 1H), 7.05 (dd, J=8.4, 9.2 Hz, 2H), 7.39-7.42 (m, 1H), 7.54-7.61 (m, 2H), 7.99 (d, J=2.2 Hz, 1H), 8.14 (d, J=2.2 Hz, 1H), 8.19 (d, J=1.2 Hz, 1H). MS (ES+) m/z 505.4 [M+H].

Example 30

2-((2-((6-(4-Chloro-1H-imidazol-1-yl)-5-methoxypyridin-3-yl)amino)-7-(4-fluorophenyl)-5,5-dimethyl-6,7-dihydro-5H-pyrrolo[2,3-d]pyrimidin-4-yl)amino)ethanol

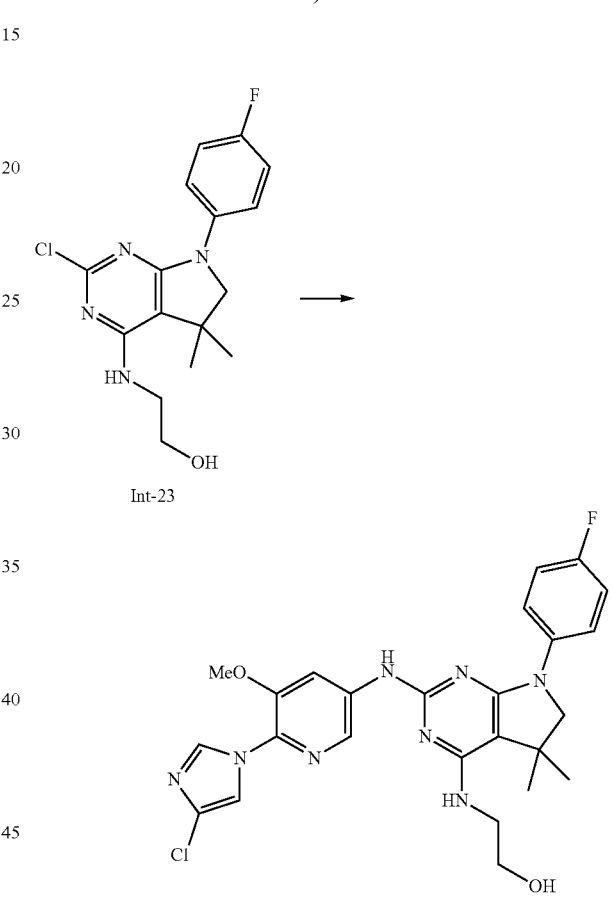

30

In a 2 mL microwave vial, 2-((2-chloro-7-(4-fluorophenyl)-5,5-dimethyl-6,7-dihydro-5H-pyrrolo[2,3-d]pyrimidin-4-yl)amino)ethanol (Int-23, 60 mg, 178 µmol) was dissolved in NMP (1.2 mL) and 6-(4-chloro-1H-imidazol-1-yl)-5-methoxypyridin-3-amine (40 mg, 178 µmol), cesium carbonate (130 mg, 399 µmol), 2-dicyclohexylphosphino-2'-(N,N-dimethylamino)biphenyl (14 mg, 36 µmol), and bis(dibenzylideneacetone)palladium(0) (18 mg, 31 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as a brown solid (50 mg, 53%). HPLC (method LCMS_fastgradient) $t_R$=1.21 min. $^1$H NMR (CDCl$_3$, 300 MHz): δ 1.46 (s, 6H), 3.16 (br s, 1H), 3.69-3.76 (m, 2H), 3.71 (s, 3H), 3.81 (s, 3H), 3.84-3.89 (m, 2H), 4.74 (t, J=5.6 Hz, 1H), 6.90 (s, 1H), 7.06 (dd, J=8.3, 9.1 Hz, 2H), 7.54-7.60 (m, 2H), 7.62 (d, J=1.6 Hz, 1H), 8.00 (d, J=2.2 Hz, 1H), 8.18 (d, J=1.4 Hz, 1H), 8.19 (d, J=2.0 Hz, 1H). MS (ES+) m/z 525.2 [M+H].

Example 31

2-((2-((3-Fluoro-4-(3-methyl-1H-1,2,4-triazol-1-yl)phenyl)amino)-7-(4-fluorophenyl)-5,5-dimethyl-6,7-dihydro-5H-pyrrolo[2,3-d]pyrimidin-4-yl)amino)ethanol (sodium sulfate) and concentrated in vacuo. The crude product was purified by column chromatography (silica gel, 12 g, eluting with methanol/dichloromethane, gradient 0:100 to 5:95) to yield the title compound as a light brown solid (39 mg, 44%). HPLC (method LCMS_fastgradient) $t_R$=1.14 min. $^1$H NMR (CDCl$_3$, 300 MHz): δ 1.45 (s, 6H), 2.51 (s, 3H), 3.20 (br s, 1H), 3.67-3.74 (m, 2H), 3.71 (s, 2H), 3.85-3.90 (m, 2H), 4.72 (t, J=5.7 Hz, 1H), 6.92 (s, 1H), 7.09 (dd, J=8.4, 9.2 Hz, 2H), 7.12-7.18 (m, 1H), 7.56-7.69 (m, 3H), 8.07 (dd, J=2.4, 14.5 Hz, 1H), 8.44 (d, J=2.6 Hz, 1H). MS (ES+) m/z 493.2 [M+H].

Example 32

7-(4-Fluorophenyl)-N2-(3-methoxy-4-(3-methyl-1H-1,2,4-triazol-1-yl)phenyl)-N4-methyl-6,7-dihydro-5H-pyrrolo[2,3-d]pyrimidine-2,4-diamine

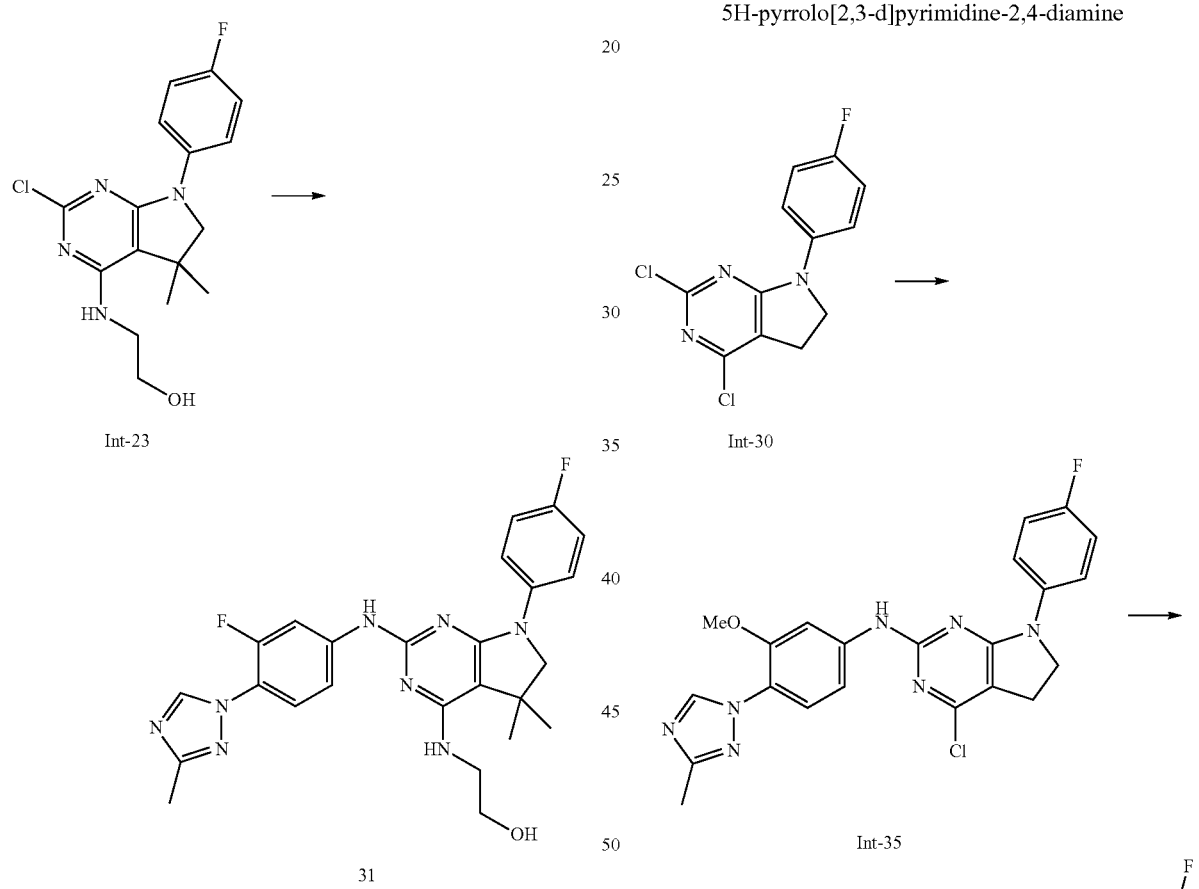

In a 2 mL microwave vial, 2-((2-chloro-7-(4-fluorophenyl)-5,5-dimethyl-6,7-dihydro-5H-pyrrolo[2,3-d]pyrimidin-4-yl)amino)ethanol (Int-23, 60 mg, 178 μmol) was dissolved in NMP (1.2 mL) and 3-fluoro-4-(3-methyl-1H-1,2,4-triazol-1-yl)aniline (41 mg, 213 μmol), cesium carbonate (130 mg, 399 μmol), 2-dicyclohexylphosphino-2'-(N,N-dimethylamino)biphenyl (14 mg, 36 μmol), and bis(dibenzylideneacetone)palladium(0) (18 mg, 31 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried

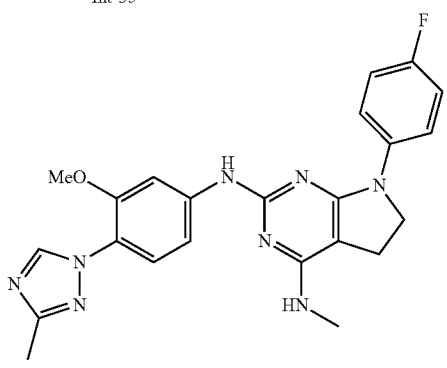

Step 1: 4-Chloro-7-(4-fluorophenyl)-N-(3-methoxy-4-(3-methyl-1H-1,2,4-triazol-1-yl)phenyl)-6,7-dihydro-5H-pyrrolo[2,3-d]pyrimidin-2-amine (Int-35)

In a screw-cap vial, 2,4-dichloro-7-(4-fluorophenyl)-6,7-dihydro-5H-pyrrolo[2,3-d]pyrimidine (Int-30, 70 mg, 246 µmol) was suspended in NMP (0.5 mL) and 3-methoxy-4-(3-methyl-1H-1,2,4-triazol-1-yl)aniline (55 mg, 269 µmol) followed by N,N-diisopropylethylamine (96.2 mg, 744 µmol) were added. The vial was flushed with Argon, closed and the mixture was stirred at 160° C. for 66 h. After cooling to room temperature, ethanol was distilled off, water (3 mL) was added and the mixture was extracted with tertbutylmethyl ether (TBME, 2×30 mL). The organic layers were washed with water (4×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 70:30) to afford the title compound as a light yellow solid (38 mg, 27%). HPLC (method LCMS_fastgradient) $t_R$=1.38 min. $^1$H NMR (CDCl$_3$, 300 MHz): δ 2.50 (s, 3H), 3.14 (t, J=8.5 Hz, 2H), 3.82 (s, 3H), 4.12 (t, J=8.6 Hz, 2H), 6.99 (dd, J=2.2, 8.7 Hz, 1H), 7.06-7.14 (m, 2H), 7.60 (d, J=8.7 Hz, 1H), 7.64-7.69 (m, 2H), 7.77 (d, J=2.0 Hz, 1H), 8.52 (s, 1H). MS (ES+) m/z 452.2, 454.2 [M+H, Cl isotopes].

Step 2: 7-(4-Fluorophenyl)-N2-(3-methoxy-4-(3-methyl-1H-1,2,4-triazol-1-yl)phenyl)-N4-methyl-6,7-dihydro-5H-pyrrolo[2,3-d]pyrimidine-2,4-diamine (32)

In a screw-cap vial, 4-chloro-7-(4-fluorophenyl)-N-(3-methoxy-4-(3-methyl-1H-1,2,4-triazol-1-yl)phenyl)-6,7-dihydro-5H-pyrrolo[2,3-d]pyrimidin-2-amine (Int-35, 55 mg, 97 µmol) was dissolved in NMP (0.3 mL) and a solution of methylamine in ethanol (33% m/m, 302 mg, 0.4 mL, 3.21 mmol) was added. The vial was flushed with Argon and closed, the mixture was stirred at 120° C. for 18 h. After cooling to room temperature, water (3 mL) was added and the mixture was extracted with tertbutylmethyl ether (TBME, 2×40 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 100:0) to yield the title compound as an off-white solid (21 mg, 46%). HPLC (method LCMS_fastgradient) $t_R$=0.99 min. $^1$H NMR (CDCl$_3$, 300 MHz): δ 2.50 (s, 3H), 2.90 (t, J=8.7 Hz, 2H), 3.12 (d, J=4.8 Hz, 3H), 3.85 (s, 3H), 4.04 (t, J=8.7 Hz, 2H), 4.08-4.15 (m, 1H), 6.95 (s, 1H), 7.02-7.10 (m, 3H), 7.56 (d, J=8.7 Hz, 1H), 7.62-7.69 (m, 2H), 7.89 (d, J=2.0 Hz, 1H), 8.49 (s, 1H). MS (ES+) m/z 447.3 [M+H].

Example 33

7-(4-Fluorophenyl)-N2-(5-methoxy-6-(4-methyl-1H-imidazol-1-yl)pyridin-3-yl)-N4-methyl-6,7-dihydro-5H-pyrrolo[2,3-d]pyrimidine-2,4-diamine

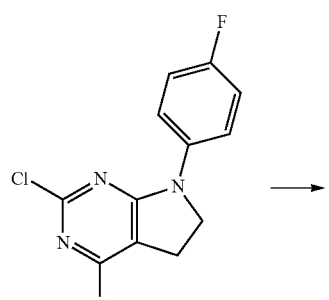

Int-30

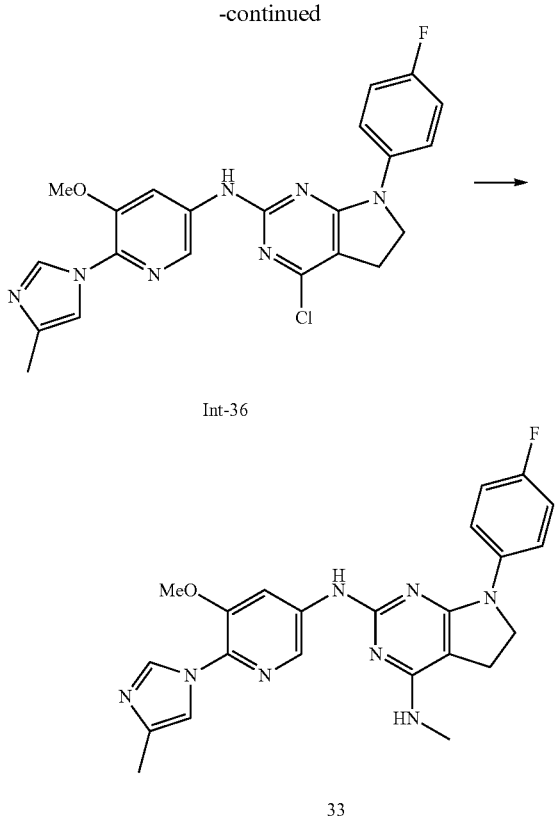

Int-36

33

Step 1: 4-Chloro-7-(4-fluorophenyl)-N-(5-methoxy-6-(4-methyl-1H-imidazol-1-yl)pyridin-3-yl)-6,7-dihydro-5H-pyrrolo[2,3-d]pyrimidin-2-amine (Int-36)

2,4-Dichloro-7-(4-fluorophenyl)-6,7-dihydro-5H-pyrrolo[2,3-d]pyrimidine (Int-30, 80 mg, 282 µmol) and 5-methoxy-6-(4-methyl-1H-imidazol-1-yl)pyridin-3-amine (70 mg, 343 µmol) were suspended in THF (1.0 mL) and a solution of lithium bis(trimethylsilyl)amide in THF/ethylbenzene (1.0 M, 290 µL, 290 µmol) was added at room temperature. The mixture was stirred at 55° C. for 5 h, followed by 10 h at room temperature. Then, water (3 mL) was added and the mixture was extracted with ethyl acetate (2×40 mL). The organic layers were washed with water (1×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to afford the title compound as a light yellow solid (46 mg, 36%). HPLC (method LCMS_fastgradient) $t_R$=1.09 min. $^1$H NMR (DMSO-d$_6$, 300 MHz): δ 2.16 (d, J=1.0 Hz, 3H), 3.08 (dd, J=7.8, 8.9 Hz, 2H), 3.82 (s, 3H), 4.16 (t, J=8.4 Hz, 2H), 7.27 (dd, J=8.7, 9.1 Hz, 2H), 7.41-7.44 (m, 1H), 7.82-7.88 (m, 2H), 8.10 (d, J=1.4 Hz, 1H), 8.13 (d, J=1.8 Hz, 1H), 8.35 (d, J=2.0 Hz, 1H). MS (ES+) m/z 452.2, 454.2 [M+H, Cl isotopes].

Step 2: 7-(4-Fluorophenyl)-N2-(5-methoxy-6-(4-methyl-1H-imidazol-1-yl)pyridin-3-yl)-N4-methyl-6,7-dihydro-5H-pyrrolo[2,3-d]pyrimidine-2,4-diamine (33)

In a screw-cap vial, 4-chloro-7-(4-fluorophenyl)-N-(5-methoxy-6-(4-methyl-1H-imidazol-1-yl)pyridin-3-yl)-6,7- dihydro-5H-pyrrolo[2,3-d]pyrimidin-2-amine (Int-36, 44 mg, 97 μmol) was dissolved in NMP (0.4 mL) and a solution of methylamine in ethanol (33% m/m, 302 mg, 0.4 mL, 3.21 mmol) was added. The vial was flushed with Argon and closed, the mixture was stirred at 130° C. for 18 h. Then a second portion of a solution of methylamine in ethanol (33% m/m, 302 mg, 0.4 mL, 3.21 mmol) was added. The vial was flushed again with Argon and closed, the mixture was stirred at 130° C. for 24 h. After cooling to room temperature, water (3 mL) was added and the mixture was extracted with a mixture of ethyl acetate/tertbutylmethyl ether (1:1 v/v, 2×40 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to afford the title compound as an off-white solid (25 mg, 57%). HPLC (method LCMS_fastgradient) $t_R$=0.90 min. $^1$H NMR (DMSO-d6, 300 MHz): δ 2.16 (d, J=1.0 Hz, 3H), 2.84 (dd, J=8.3, 8.9 Hz, 2H), 2.96 (d, J=4.6 Hz, 3H), 3.87 (s, 3H), 3.98 (t, J=8.6 Hz, 2H), 6.55-6.63 (m, 1H), 7.16 (dd, J=8.9, 9.1 Hz, 2H), 7.38-7.40 (m, 1H), 7.80-7.86 (m, 2H), 8.06 (d, J=1.2 Hz, 1H), 8.36 (d, J=2.0 Hz, 1H), 8.49 (d, J=1.6 Hz, 1H). MS (ES+) m/z 447.1 [M+H].

Example 34

N2-(3-Fluoro-4-(4-methyl-1H-imidazol-1-yl)phenyl)-7-(4-fluorophenyl)-N4,5,5-trimethyl-6,7-dihydro-5H-pyrrolo[2,3-d]pyrimidine-2,4-diamine

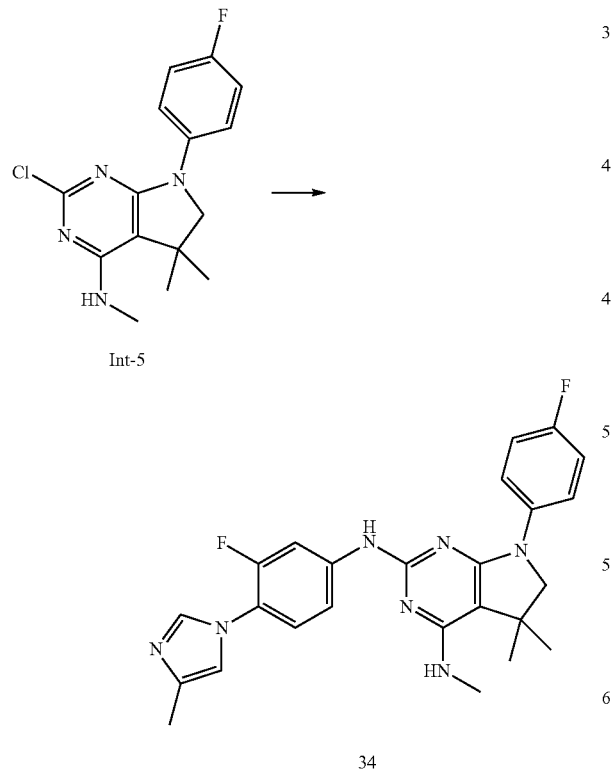

34

In a 2 mL microwave vial, 2-chloro-7-(4-fluorophenyl)-N,5,5-trimethyl-6,7-dihydro-5H-pyrrolo[2,3-d]pyrimidin-4-amine (Int-5, 60 mg, 196 μmol) was dissolved in NMP (1.3 mL) and 3-fluoro-4-(4-methyl-1H-imidazol-1-yl)aniline (45 mg, 235 μmol), cesium carbonate (140 mg, 430 μmol), 2-dicyclohexylphosphino-2'-(N,N-dimethylamino)biphenyl (15 mg, 38 μmol), and bis(dibenzylideneacetone)palladium (0) (20 mg, 35 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 25 g, eluting with methanol/dichloromethane, gradient 0:100 to 5:95), followed by reversed phase prep HPLC (Gemini NX 3u 50×4.6 mm, flow 1.4 mL/min, eluting with acetonitrile/(water+0.05% triethyl amine) 40:60) to yield the title compound as a light yellow foam (55 mg, 61%). HPLC (method LCMS_fastgradient) $t_R$=1.01 min. $^1$H NMR (CDCl$_3$, 300 MHz): δ 1.43 (s, 6H), 2.31 (d, J=1.0 Hz, 3H), 3.11 (d, J=4.8 Hz, 3H), 3.68 (s, 2H), 4.21-4.28 (m, 1H), 6.92-6.94 (m, 1H), 7.00 (br s, 1H), 7.02-7.11 (m, 2H), 7.12-7.25 (m, 2H), 7.57-7.64 (m, 2H), 7.65-7.67 (m, 1H), 8.12 (dd, J=2.4, 14.1 Hz, 1H). MS (ES+) m/z 462.4 [M+H].

Example 35

8-(4-Fluorophenyl)-N2-(3-methoxy-4-(3-methyl-1H-1,2,4-triazol-1-yl)phenyl)-N4,5,5-trimethyl-5,6,7,8-tetrahydropyrido[2,3-d]pyrimidine-2,4-diamine

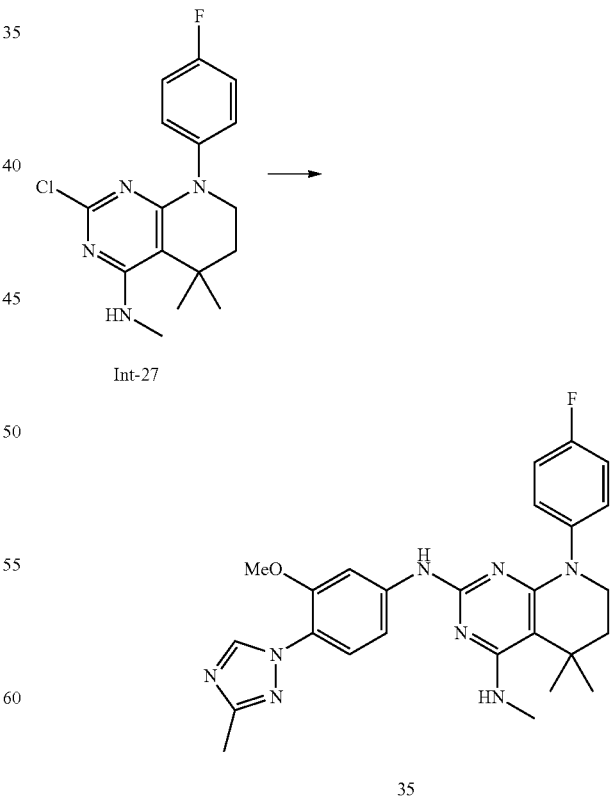

35

In a 2 mL microwave vial, 2-chloro-8-(4-fluorophenyl)-N,5,5-trimethyl-5,6,7,8-tetrahydro-pyrido[2,3-d]pyrimidin- 4-amine (Int-27, 50 mg, 156 μmol) was dissolved in NMP (1.0 mL) and 3-methoxy-4-(3-methyl-1H-1,2,4-triazol-1-yl) aniline (39 mg, 191 μmol), cesium carbonate (112 mg, 344 μmol), 2-dicyclohexylphosphino-2'-(N,N-dimethylamino)biphenyl (13 mg, 33 μmol), and bis(dibenzylideneacetone)palladium(0) (16 mg, 28 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 80:20) to afford the title compound as an off-white foam (46 mg, 60%). HPLC (method LCMS_fastgradient) $t_R$=0.99 min. $^1$H NMR (CDCl$_3$, 300 MHz): δ 1.42 (s, 6H), 1.88-1.95 (m, 2H), 2.48 (s, 3H), 3.08 (d, J=4.6 Hz, 3H), 3.59-3.64 (m, 2H), 3.63 (s, 3H), 4.54-4.62 (m, 1H), 6.65 (s, 1H), 6.90 (dd, J=2.2, 8.7 Hz, 1H), 7.02-7.10 (m, 2H), 7.20-7.26 (m, 2H), 7.37 (d, J=8.7 Hz, 1H), 7.49 (d, J=2.0 Hz, 1H), 8.40 (s, 1H). MS (ES+) m/z 489.3 [M+H].

Example 36

N2-(5-Fluoro-6-(4-methyl-1H-imidazol-1-yl)pyridin-3-yl)-8-(4-fluorophenyl)-N4,5,5-trimethyl-5,6,7,8-tetrahydropyrido[2,3-d]pyrimidine-2,4-diamine (1.0 mL) and 5-fluoro-6-(4-methyl-1H-imidazol-1-yl)pyridin-3-amine (36 mg, 187 μmol), cesium carbonate (120 mg, 368 μmol), 2-dicyclohexylphosphino-2'-(N,N-dimethylamino)biphenyl (12 mg, 31 μmol), and bis(dibenzylideneacetone)palladium(0) (16 mg, 28 μmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (2×30 mL). The organic layers were washed with water (5×3 mL) and brine (1×3 mL), combined, dried (sodium sulfate) and concentrated in vacuo. The crude product was purified by column chromatography (silica gel, 25 g, eluting with ethyl acetate/n-heptane, gradient 0:100 to 80:20) to yield the title compound as a light yellow foam (42 mg, 54%). HPLC (method LCMS_fastgradient) $t_R$=0.97 min. $^1$H NMR (CDCl$_3$, 300 MHz): δ 1.43 (s, 6H), 1.91-1.98 (m, 2H), 2.30 (d, J=1.0 Hz, 3H), 3.05 (d, J=4.6 Hz, 3H), 3.59-3.66 (m, 2H), 4.57-4.64 (m, 1H), 6.81 (s, 1H), 7.07-7.16 (m, 2H), 7.18-7.25 (m, 2H), 7.30-7.34 (m, 1H), 7.86 (d, J=1.8 Hz, 1H), 8.08 (dd, J=2.2, 11.3 Hz, 1H), 8.10 (d, J=1.4 Hz, 1H). MS (ES+) m/z 477.4 [M+H].

Example 37

N2-(3-Fluoro-4-(4-methyl-1H-imidazol-1-yl)phenyl)-8-(4-fluorophenyl)-N4,5,5-trimethyl-5,6,7,8-tetrahydropyrido[2,3-d]pyrimidine-2,4-diamine

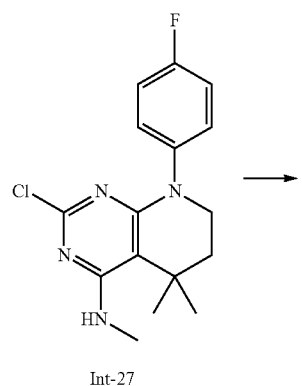

Int-27

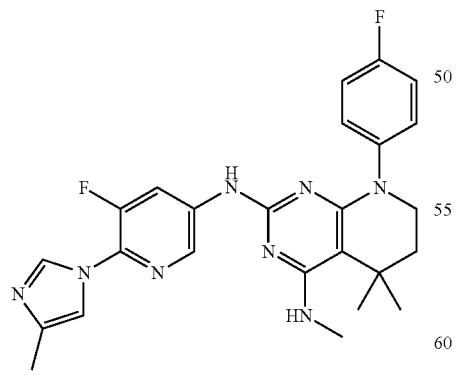

36

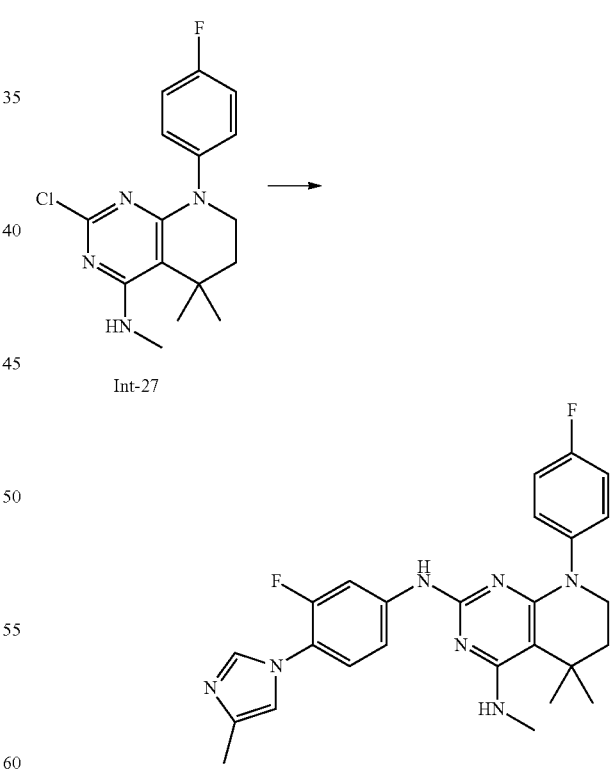

37

In a 2 mL microwave vial, 2-chloro-8-(4-fluorophenyl)-N,5,5-trimethyl-5,6,7,8-tetrahydro-pyrido[2,3-d]pyrimidin-4-amine (Int-27, 50 mg, 156 μmol) was dissolved in NMP In a 2 mL microwave vial, 2-chloro-8-(4-fluorophenyl)-N,5,5-trimethyl-5,6,7,8-tetrahydro-pyrido[2,3-d]pyrimidin-4-amine (Int-27, 50 mg, 156 μmol) was dissolved in NMP (1.0 mL) and 3-fluoro-4-(4-methyl-1H-imidazol-1-yl)aniline (36 mg, 188 µmol), cesium carbonate (120 mg, 368 µmol), 2-dicyclohexylphosphino-2'-(N,N-dimethylamino)biphenyl (12 mg, 31 µmol), and bis(dibenzylideneacetone)palladium(0) (16 mg, 28 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (2×30 mL). The organic layers were washed with water (5×3 mL) and brine (1×3 mL), combined, dried (sodium sulfate) and concentrated in vacuo. The crude product was purified by column chromatography (silica gel, 24 g, eluting with ethyl acetate/n-heptane, gradient 0:100 to 80:20) to afford the title compound as an off-white solid (36 mg, 46%). HPLC (method LCMS_fastgradient) $t_R$=0.88 min. $^1$H NMR (CDCl$_3$, 300 MHz): δ 1.42 (s, 6H), 1.90-1.97 (m, 2H), 2.30 (d, J=0.8 Hz, 3H), 3.05 (d, J=4.8 Hz, 3H), 3.59-3.66 (m, 2H), 4.53-4.61 (m, 1H), 6.70 (s, 1H), 6.82-6.88 (m, 2H), 6.99-7.14 (m, 3H), 7.19-7.26 (m, 2H), 7.56-7.64 (m, 2H). MS (ES+) m/z 476.2 [M+H].

Example 38

N2-(3-Fluoro-4-(4-methyl-1H-imidazol-1-yl)phenyl)-7-(4-fluorophenyl)-N4-methyl-6,7-dihydro-5H-pyrrolo[2,3-d]pyrimidine-2,4-diamine

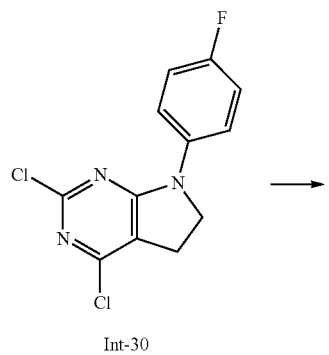

Int-30

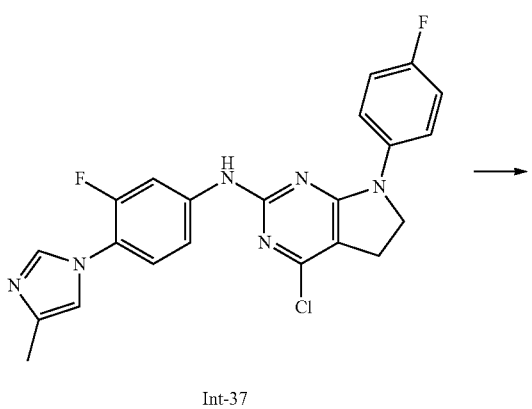

Int-37

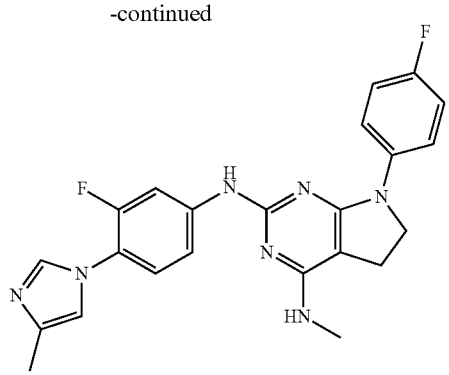

38

Step 1: 4-Chloro-N-(3-fluoro-4-(4-methyl-1H-imidazol-1-yl)phenyl)-7-(4-fluorophenyl)-6,7-dihydro-5H-pyrrolo[2,3-d]pyrimidin-2-amine (Int-37)

2,4-Dichloro-7-(4-fluorophenyl)-6,7-dihydro-5H-pyrrolo[2,3-d]pyrimidine (Int-30, 75 mg, 264 µmol) and 3-fluoro-4-(4-methyl-1H-imidazol-1-yl)aniline (56 mg, 293 µmol) were dissolved in THF (1.0 mL) and a solution of lithium bis(trimethylsilyl)amide in THF/ethylbenzene (1.0 M, 280 µL, 280 µmol) was added at room temperature. The mixture was stirred for 1 h at room temperature. Then, water (3 mL) was added and the mixture was extracted with ethyl acetate (2×40 mL). The organic layers were washed with water (1×3 mL) and brine (1×3 mL), combined, dried (sodium sulfate) and concentrated in vacuo. The crude product was purified by column chromatography (silica gel, 24 g, eluting with methanol/dichloromethane, gradient 0:100 to 5:95) to afford the title compound as a light yellow solid (43 mg, 37%). HPLC (method LCMS_fastgradient) $t_R$=1.06 min. $^1$H NMR (CDCl3, 300 MHz): δ 2.32 (d, J=1.0 Hz, 3H), 3.12-3.20 (m, 2H), 4.11-4.18 (m, 2H), 6.93-6.95 (m, 1H), 7.09-7.18 (m, 4H), 7.26 (dd, J=8.5, 8.5 Hz, 1H), 7.64-7.70 (m, 3H), 7.94 (dd, J=2.3, 13.4 Hz, 1H). MS (ES+) m/z 439.1, 441.0 [M+H, Cl isotopes].

Step 2: N2-(3-Fluoro-4-(4-methyl-1H-imidazol-1-yl)phenyl)-7-(4-fluorophenyl)-N4-methyl-6,7-dihydro-5H-pyrrolo[2,3-d]pyrimidine-2,4-diamine (38)

In a screw-cap vial, 4-chloro-N-(3-fluoro-4-(4-methyl-1H-imidazol-1-yl)phenyl)-7-(4-fluorophenyl)-6,7-dihydro-5H-pyrrolo[2,3-d]pyrimidin-2-amine (Int-37, 39 mg, 89 µmol) was suspended in NMP (0.3 mL) and a solution of methylamine in ethanol (33% m/m, 333 mg, 0.44 mL, 3.53 mmol) was added. The vial was flushed with Argon and closed, the mixture was stirred at 120° C. for 18 h. After cooling to room temperature, water (3 mL) was added and the mixture was extracted with tertbutylmethyl ether (2×40 mL). The organic layers were washed with water (4×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as an off-white solid (22 mg, 57%). HPLC (method LCMS_fastgradient) $t_R$=0.88 min. $^1$H NMR (CDCl3, 300 MHz): δ 2.32 (d, J=1.0 Hz, 3H), 2.88-2.95 (m, 2H), 3.11 (d, J=4.8 Hz, 3H), 4.01-4.08 (m, 2H), 4.12-4.19

(m, 1H), 6.92-6.94 (m, 1H), 6.95 (br s, 1H), 7.03-7.12 (m, 2H), 7.12-7.17 (m, 1H), 7.22 (dd, J=8.5, 8.5 Hz, 1H), 7.60-7.67 (m, 3H), 8.12 (dd, J=2.2, 13.9 Hz, 1H). MS (ES+) m/z 434.1 [M+H].

Example 39

7-(4-Fluorophenyl)-N2-(3-methoxy-4-(3-methyl-1H-1,2,4-triazol-1-yl)phenyl)-N4,5-dimethyl-6,7-dihydro-5H-pyrrolo[2,3-d]pyrimidine-2,4-diamine

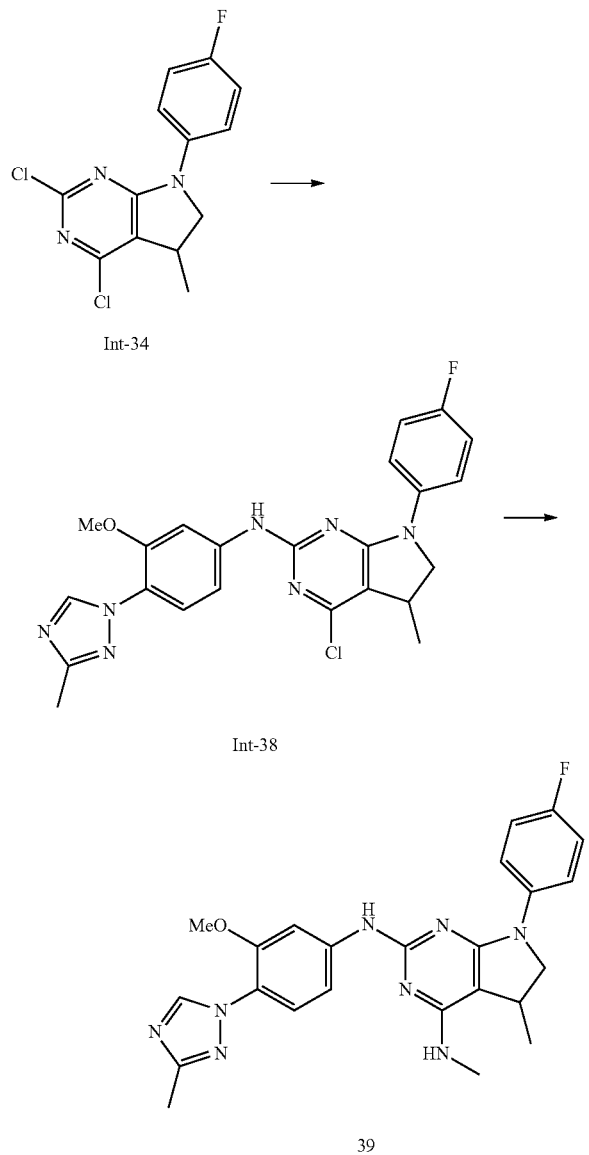

Step 1: 4-Chloro-7-(4-fluorophenyl)-N-(3-methoxy-4-(3-methyl-1H-1,2,4-triazol-1-yl)phenyl)-5-methyl-6,7-dihydro-5H-pyrrolo[2,3-d]pyrimidin-2-amine (Int-38)

2,4-Dichloro-7-(4-fluorophenyl)-5-methyl-6,7-dihydro-5H-pyrrolo[2,3-d]pyrimidine (Int-34, 185 mg, 621 μmol) and 3-methoxy-4-(3-methyl-1H-1,2,4-triazol-1-yl)aniline (185 mg, 906 μmol) were suspended in dry THF (10.0 mL) and a solution of lithium bis(trimethylsilyl)amide in THF/ethylbenzene (1.0 M, 860 μL, 860 μmol) was added at room temperature. The mixture was stirred at room temperature for 40 min. Then, a second portion of the solution of lithium bis(trimethylsilyl)amide in THF/ethylbenzene (1.0 M, 700 μL, 700 μmol) was added and the resulting mixture stirred for further 30 min at room temperature. After that, saturated aqueous ammonium chloride solution (100 mL) was added, the mixture was extracted with ethyl acetate (2×80 mL), the combined organics washed with brine (1×100 mL), dried (sodium sulfate) and concentrated in vacuo. The crude product was purified by column chromatography (silica gel, 80 g, eluting with 2N ammonia in methanol/dichloromethane, gradient 0:100 to 3:97) to afford the title compound as a yellow solid (205 mg, 61%). HPLC (method LCMS_fastgradient) $t_R$=1.09 min. $^1$H NMR (DMSO-d6, 300 MHz): δ 1.35 (d, J=6.8 Hz, 3H), 2.33 (s, 3H), 3.40-3.52 (m, 1H), 3.70 (dd, J=4.3, 10.0 Hz, 1H), 3.74 (s, 3H), 4.30 (dd, J=9.9, 9.9 Hz, 1H), 7.22-7.31 (m, 2H), 7.38 (dd, J=2.0, 8.7 Hz, 1H), 7.47 (d, J=8.7 Hz, 1H), 7.71 (d, J=1.6 Hz, 1H), 7.81-7.88 (m, 2H), 8.66 (s, 1H), 9.83 (s, 1H). MS (ES+) m/z 466.2, 468.2 [M+H, Cl isotopes].

Step 2: 7-(4-Fluorophenyl)-N2-(3-methoxy-4-(3-methyl-1H-1,2,4-triazol-1-yl)phenyl)-N4,5-dimethyl-6,7-dihydro-5H-pyrrolo[2,3-d]pyrimidine-2,4-diamine (39)

In a screw-cap pressure vial, 4-chloro-7-(4-fluorophenyl)-N-(3-methoxy-4-(3-methyl-1H-1,2,4-triazol-1-yl)phenyl)-5-methyl-6,7-dihydro-5H-pyrrolo[2,3-d]pyrimidin-2-amine (Int-38, 100 mg, 215 μmol) was dissolved in NMP (1.0 mL) and a solution of methylamine in ethanol (33% m/m, 4.7 g, 50 mmol) was added. The vial was flushed with Argon and closed, the mixture was stirred at 120° C. for 16 h. After cooling to room temperature, the reaction mixture was concentrated in high vacuo at 60° C. The crude product was purified by column chromatography (silica gel, 24 g, eluting with 2N ammonia in methanol/dichloromethane, gradient 1:99 to 2:98) to yield the title compound as a light yellow solid (83 mg, 82%). HPLC (method LCMS_fastgradient) $t_R$=1.02 min. $^1$H NMR (DMSO-d6, 300 MHz): δ 1.19 (d, J=6.7 Hz, 3H), 2.32 (s, 3H), 2.95 (d, J=4.6 Hz, 3H), 3.26-3.33 (m, 1H), 3.51 (dd, J=3.4, 9.8 Hz, 1H), 3.79 (s, 3H), 4.09 (dd, J=9.7, 9.7 Hz, 1H), 6.44-6.48 (m, 1H), 7.13-7.17 (m, 2H), 7.36-7.40 (m, 2H), 7.80-7.84 (m, 2H), 8.03 (br s, 1H), 8.62 (s, 1H), 9.10 (br s, 1H). MS (ES+) m/z 461.3 [M+H].

Example 40

7-(4-Fluorophenyl)-N2-(5-methoxy-6-(4-methyl-1H-imidazol-1-yl)pyridin-3-yl)-N4,5-dimethyl-6,7-dihydro-5H-pyrrolo[2,3-d]pyrimidine-2,4-diamine

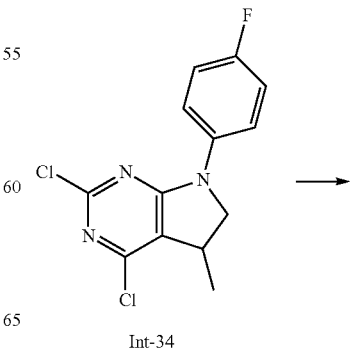

-continued

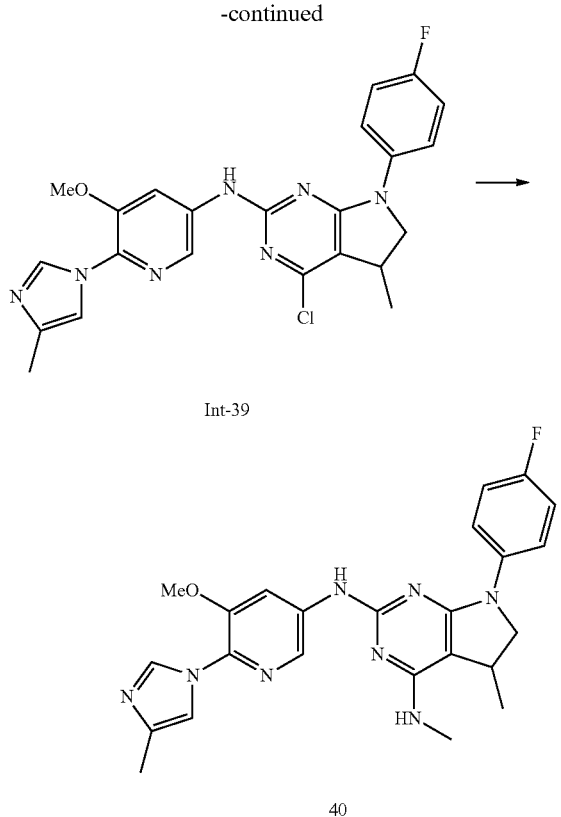

Int-39

40

Step 1: 4-Chloro-7-(4-fluorophenyl)-N-(5-methoxy-6-(4-methyl-1H-imidazol-1-yl)pyridin-3-yl)-5-methyl-6,7-dihydro-5H-pyrrolo[2,3-d]pyrimidin-2-amine (Int-39)

2,4-Dichloro-7-(4-fluorophenyl)-5-methyl-6,7-dihydro-5H-pyrrolo[2,3-d]pyrimidine (Int-34, 193 mg, 647 µmol) and 5-methoxy-6-(4-methyl-1H-imidazol-1-yl)pyridine-3-amine (193 mg, 945 µmol) were suspended in dry THF (10.0 mL) and a solution of lithium bis(trimethylsilyl)amide in THF/ethylbenzene (1.0 M, 900 µL, 900 µmol) was added at room temperature. The mixture was stirred at room temperature for 30 min. Then, a second portion of the solution of lithium bis(trimethylsilyl)amide in THF/ethylbenzene (1.0 M, 900 µL, 900 µmol) was added and the resulting mixture stirred for further 50 min at room temperature. After that, saturated aqueous ammonium chloride solution (100 mL) was added, the mixture was extracted with ethyl acetate (2×80 mL), the combined organics washed with brine (1×100 mL), dried (sodium sulfate) and concentrated in vacuo. The crude product was purified by column chromatography (silica gel, 80 g, eluting with 2N ammonia in methanol/dichloromethane, gradient 1:99 to 4:96) to afford the title compound as a yellow solid (266 mg, 83%). HPLC (method LCMS_fastgradient) $t_R$=1.07 min. $^1$H NMR (DMSO-d6, 300 MHz): δ 1.35 (d, J=6.8 Hz, 3H), 2.16 (d, J=1.0 Hz, 3H), 3.40-3.52 (m, 1H), 3.70 (dd, J=4.3, 10.0 Hz, 1H), 3.81 (s, 3H), 4.30 (dd, J=9.8, 9.8 Hz, 1H), 7.21-7.30 (m, 2H), 7.40-7.43 (m, 1H), 7.80-7.87 (m, 2H), 8.10 (d, J=1.2 Hz, 1H), 8.33 (d, J=1.8 Hz, 1H), 9.94 (br s, 1H). MS (ES+) m/z 466.2, 468.2 [M+H, Cl isotopes].

Step 2: 7-(4-Fluorophenyl)-N2-(5-methoxy-6-(4-methyl-1H-imidazol-1-yl)pyridin-3-yl)-N4,5-dimethyl-6,7-dihydro-5H-pyrrolo[2,3-d]pyrimidine-2,4-diamine (40)

In a screw-cap pressure vial, 4-chloro-7-(4-fluorophenyl)-N-(5-methoxy-6-(4-methyl-1H-imidazol-1-yl)pyridin-3-yl)-5-methyl-6,7-dihydro-5H-pyrrolo[2,3-d]pyrimidin-2-amine (Int-39, 55 mg, 118 µmol) was dissolved in NMP (0.3 mL) and a solution of methylamine in ethanol (33% m/m, 4.7 g, 50 mmol) was added. The vial was flushed with Argon and closed, the mixture was stirred at 120° C. for 16 h. After cooling to room temperature, the reaction mixture was concentrated in high vacuo at 60° C. The crude product was purified by column chromatography (silica gel, 12 g, eluting with 2N ammonia in methanol/dichloromethane, gradient 1:99 to 6:94) to yield the title compound as an off-white solid (46 mg, 82%). HPLC (method LCMS_fastgradient) $t_R$=0.93 min. $^1$H NMR (DMSO-d6, 300 MHz): δ 1.19 (d, J=6.7 Hz, 3H), 2.16 (d, J=0.7 Hz, 3H), 2.96 (d, J=4.6 Hz, 3H), 3.28-3.33 (m, 1H), 3.52 (dd, J=3.4, 9.7 Hz, 1H), 3.87 (s, 3H), 4.09 (dd, J=9.7, 9.7 Hz, 1H), 6.50-6.54 (m, 1H), 7.13-7.18 (m, 2H), 7.39-7.40 (m, 1H), 7.80-7.83 (m, 2H), 8.08 (d, J=0.8 Hz, 1H), 8.35 (d, J=2.1 Hz, 1H), 8.48 (br s, 1H). MS (ES+) m/z 461.3 [M+H].

Example 41

7-(2,3-Difluorophenyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine

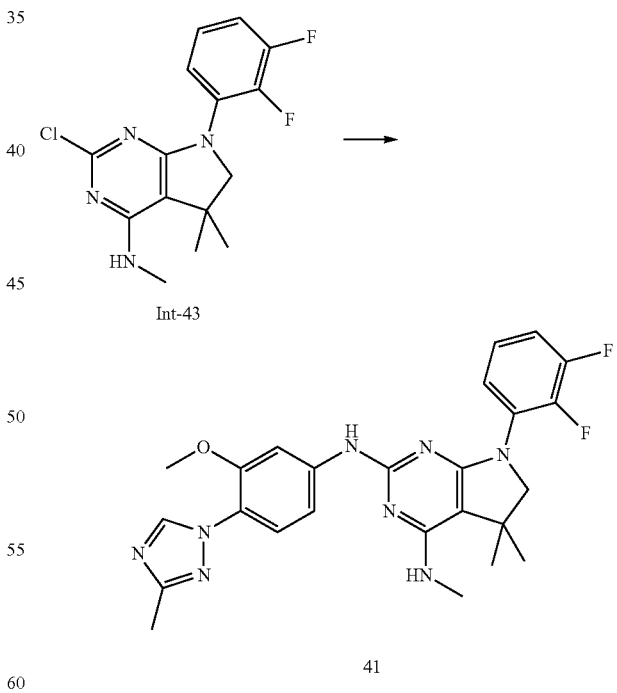

In a 2 mL microwave vial, 2-chloro-7-(2,3-difluorophenyl)-N,5,5-trimethyl-6,7-dihydro-5H-pyrrolo[2,3-d]pyrimidin-4-amine (Int-43, 50 mg, 154 µmol) was dissolved in NMP (1.0 mL) and 3-methoxy-4-(3-methyl-1H-1,2,4-triazol-1-yl)aniline (35 mg, 171 µmol), cesium carbonate (120 mg, 368 µmol), 2-dicyclohexylphosphino-2'-(N,N-dimethylamino)biphenyl (12 mg, 30.5 µmol), and bis(dibenzylideneacetone)palladium(0) (16 mg, 28 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 60:40) to yield the title compound as a light yellow foam (44 mg, 58%). HPLC (method LCMS_fastgradient) $t_R$=1.13 min. $^1$H NMR (CDCl$_3$, 300 MHz): δ 1.43 (s, 6H), 2.48 (s, 3H), 3.11 (d, J=4.8 Hz, 3H), 3.72 (d, J=1.6 Hz, 2H), 3.73 (s, 3H), 4.22-4.30 (m, 1H), 6.90-7.10 (m, 4H), 7.40-7.47 (m, 1H), 7.50 (d, J=8.7 Hz, 1H), 7.90 (d, J=2.2 Hz, 1H), 8.45 (s, 1H). MS (ES+) m/z 493.2 [M+H].

Example 42

7-(2,3-Difluorophenyl)-N2-(5-fluoro-6-(4-methyl-1H-imidazol-1-yl)pyridin-3-yl)-N4,5,5-trimethyl-6,7-dihydro-5H-pyrrolo[2,3-d]pyrimidine-2,4-diamine

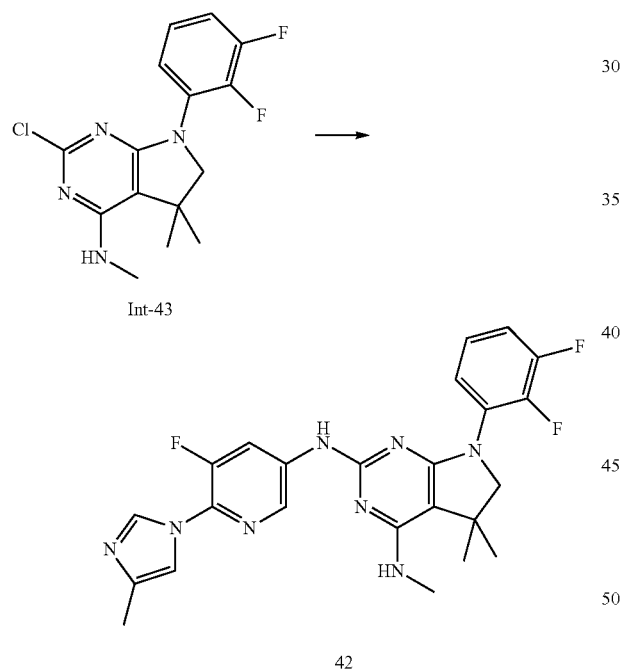

42

In a 2 mL microwave vial, 2-chloro-7-(2,3-difluorophenyl)-N,5,5-trimethyl-6,7-dihydro-5H-pyrrolo[2,3-d]pyrimidin-4-amine (Int-43, 50 mg, 154 µmol) was dissolved in NMP (1.0 mL) and 5-fluoro-6-(4-methyl-1H-imidazol-1-yl)pyridine-3-amine (33 mg, 172 µmol), cesium carbonate (120 mg, 368 µmol), 2-dicyclohexylphosphino-2'-(N,N-dimethylamino)biphenyl (12 mg, 30.5 µmol), and bis(dibenzylideneacetone)palladium(0) (16 mg, 28 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 70:30), followed by trituration with TBME/ethyl acetate to afford the title compound as an off-white solid (35 mg, 45%). HPLC (method LCMS_fastgradient) $t_R$=1.10 min. $^1$H NMR (CDCl$_3$, 300 MHz): δ 1.44 (s, 6H), 2.31 (d, J=0.8 Hz, 3H), 3.10 (d, J=4.8 Hz, 3H), 3.75 (d, J=1.4 Hz, 2H), 4.27-4.35 (m, 1H), 6.95-7.14 (m, 3H), 7.35-7.43 (m, 2H), 8.11 (dd, J=0.6, 2.2 Hz, 1H), 8.14 (dd, J=1.4, 1.4 Hz, 1H), 8.58 (dd, J=2.2, 14.3 Hz, 1H). MS (ES+) m/z 481.7 [M+H].

Example 43

7-(2,3-Difluorophenyl)-N2-(3-fluoro-4-(4-methyl-1H-imidazol-1-yl)phenyl)-N4,5,5-trimethyl-6,7-dihydro-5H-pyrrolo[2,3-d]pyrimidine-2,4-diamine

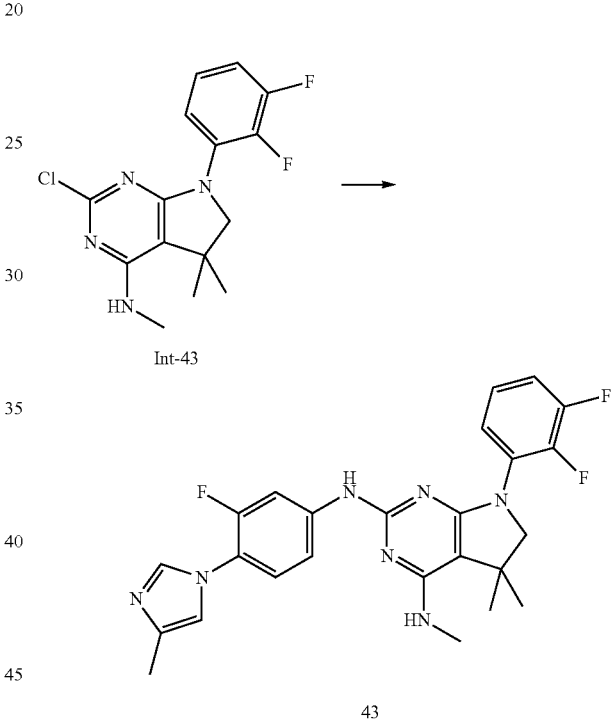

43

In a 2 mL microwave vial, 2-chloro-7-(2,3-difluorophenyl)-N,5,5-trimethyl-6,7-dihydro-5H-pyrrolo[2,3-d]pyrimidin-4-amine (Int-43, 50 mg, 154 µmol) was dissolved in NMP (1.0 mL) and 3-fluoro-4-(4-methyl-1H-imidazol-1-yl)aniline (33 mg, 173 µmol), cesium carbonate (120 mg, 368 µmol), 2-dicyclohexylphosphino-2'-(N,N-dimethylamino)biphenyl (12 mg, 30.5 µmol), and bis(dibenzylideneacetone)palladium(0) (16 mg, 28 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 80:20) to yield the title compound as a light yellow foam (49 mg, 66%). HPLC (method LCMS_fastgradient) $t_R$=0.99 min. $^1$H NMR (CDCl₃, 300 MHz): δ 1.43 (s, 6H), 2.30 (d, J=1.0 Hz, 3H), 3.11 (d, J=4.8 Hz, 3H), 3.74 (d, J=1.6 Hz, 2H), 4.23-4.33 (m, 1H), 6.88-7.21 (m, 6H), 7.40-7.48 (m, 1H), 7.63 (dd, J=1.5, 1.5 Hz, 1H), 8.06 (dd, J=2.3, 14.0 Hz, 1H). MS (ES+) m/z 480.4 [M+H].

Example 44

7-(2,3-Difluorophenyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine

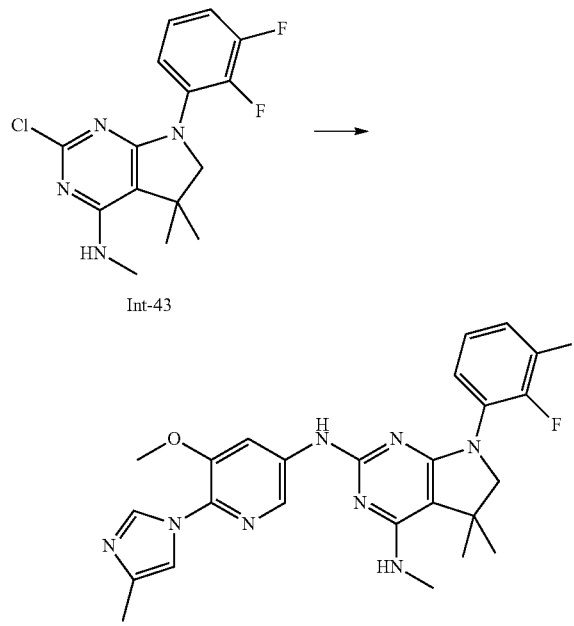

Int-43

44

In a 2 mL microwave vial, 2-chloro-7-(2,3-difluorophenyl)-N,5,5-trimethyl-6,7-dihydro-5H-pyrrolo[2,3-d]pyrimidin-4-amine (Int-43, 50 mg, 154 µmol) was dissolved in NMP (1.0 mL) and 5-methoxy-6-(4-methyl-1H-imidazol-1-yl)pyridin-3-amine (35 mg, 171 µmol), cesium carbonate (120 mg, 368 µmol), 2-dicyclohexylphosphino-2'-(N,N-dimethylamino)biphenyl (12 mg, 30.5 µmol), and bis(dibenzylideneacetone)palladium(0) (16 mg, 28 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with methanol/dichloromethane, gradient 0:100 to 5:95) to yield the title compound as a light yellow foam (51 mg, 67%). HPLC (method LCMS_fastgradient) t_R=1.00 min. ¹H NMR (CDCl₃, 300 MHz): δ 1.44 (s, 6H), 2.29 (d, J=1.0 Hz, 3H), 3.11 (d, J=4.8 Hz, 3H), 3.72 (d, J=1.4 Hz, 2H), 3.74 (s, 3H), 4.25-4.34 (m, 1H), 6.93-7.12 (m, 3H), 7.34-7.43 (m, 2H), 7.89 (d, J=2.2 Hz, 1H), 8.16 (d, J=1.2 Hz, 1H), 8.38 (d, J=2.2 Hz, 1H). MS (ES+) m/z 493.4 [M+H].

Example 45

7-(2-Chloro-4-fluorophenyl)-N2-(3-fluoro-4-(4-methyl-1H-imidazol-1-yl)phenyl)-N4,5,5-trimethyl-6,7-dihydro-5H-pyrrolo[2,3-d]pyrimidine-2,4-diamine

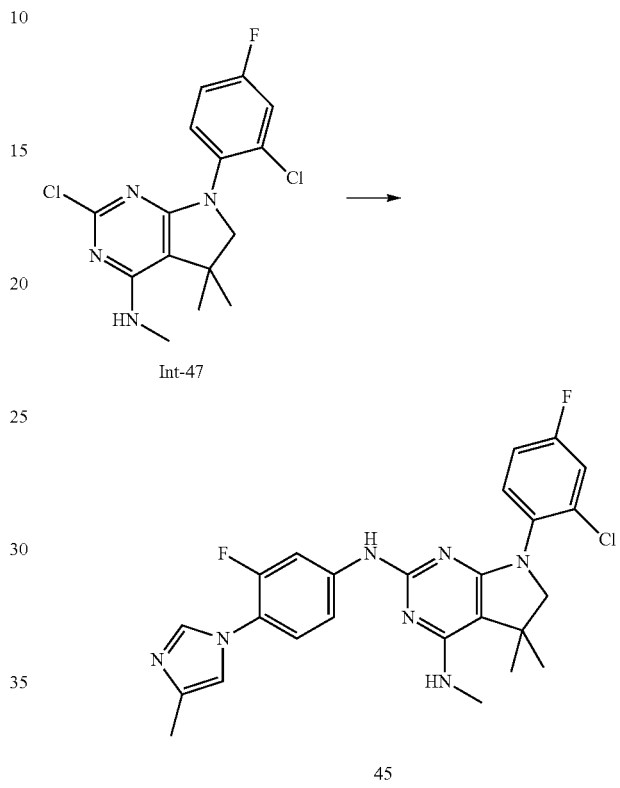

Int-47

45

In a 2 mL microwave vial, 2-chloro-7-(2-chloro-4-fluorophenyl)-N,5,5-trimethyl-6,7-dihydro-5H-pyrrolo[2,3-d]pyrimidin-4-amine (Int-47, 42 mg, 123 µmol) was dissolved in NMP (0.8 mL) and 3-fluoro-4-(4-methyl-1H-imidazol-1-yl)aniline (26 mg, 136 µmol), cesium carbonate (90 mg, 276 µmol), 2-dicyclohexylphosphino-2'-(N,N-dimethylamino)biphenyl (10 mg, 25.4 µmol), and bis(dibenzylideneacetone)palladium(0) (13 mg, 23 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The organic layers were washed with water (5×3 mL) and brine (1×3 mL), combined, dried (sodium sulfate) and concentrated in vacuo. The crude product was purified by column chromatography (silica gel, 12 g, eluting with ethyl acetate/n-heptane, gradient 0:100 to 80:20), followed by preparative SFC (RP_ID: G-9989; column: *Viridis* Silica 2-Ethylpyridine; 15% methanol, isocratic) to afford the title compound as an off-white solid (17 mg, 26%). HPLC (method LCMS_fastgradient) t_R=1.03 min. ¹H NMR (CDCl₃, 300 MHz): δ 1.46 (s, 6H), 2.31 (s, 3H), 3.16 (d, J=4.8 Hz, 3H), 3.64 (s, 2H), 4.30-4.41 (m, 1H), 6.90 (s, 1H), 7.03-7.19 (m, 3H), 7.22-7.28 (m, 2H), 7.41 (dd, J=5.6, 8.9 Hz, 1H), 7.67 (s, 1H), 7.99 (dd, J=2.1, 14.0 Hz, 1H). MS (ES+) m/z 496.4 [M+H].

Example 46p (S)- or (R)—N2-(3-Fluoro-4-(4-methyl-1H-imidazol-1-yl)phenyl)-7-(4-fluorophenyl)-N4,5-dimethyl-6,7-dihydro-5H-pyrrolo[2,3-d]pyrimidine-2,4-diamine

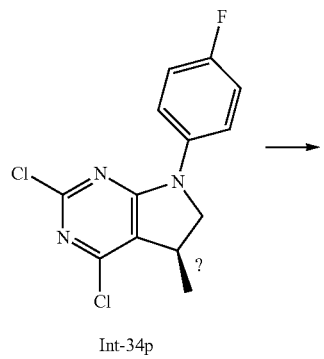

Int-34p

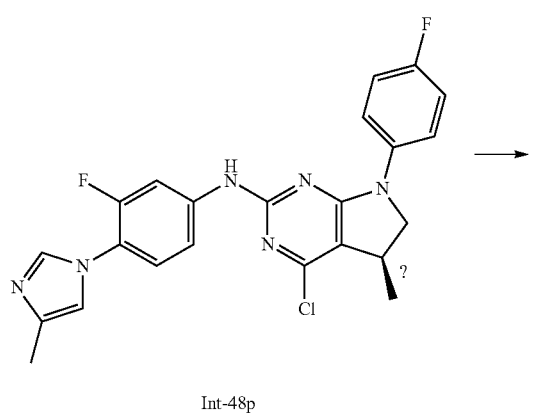

Int-48p

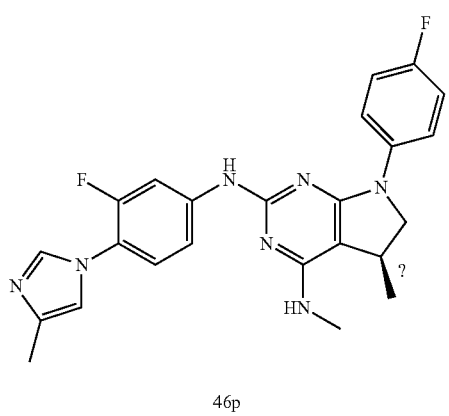

46p

Step 1: (S)- or (R)-4-Chloro-N-(3-fluoro-4-(4-methyl-1H-imidazol-1-yl)phenyl)-7-(4-fluorophenyl)-5-methyl-6,7-dihydro-5H-pyrrolo[2,3-d]pyrimidin-2-amine (Int-48p)

(−)-2,4-Dichloro-7-(4-fluorophenyl)-5-methyl-6,7-dihydro-5H-pyrrolo[2,3-d]pyrimidine (Int-34p, 65 mg, 218 µmol) and 3-fluoro-4-(4-methyl-1H-imidazol-1-yl)aniline (45.9 mg, 240 µmol) were dissolved in THF (3.0 mL) and a solution of lithium bis(trimethylsilyl)amide in THF/ethylbenzene (1.0 M, 262 µL, 262 µmol) was added at room temperature. The mixture was stirred for 30 min at room temperature. Then, a second portion of lithium bis(trimethylsilyl)amide in THF/ethylbenzene (1.0 M, 65 µL, 65 µmol) was added the mixture was stirred for further 90 min at room temperature. After that, the dark reaction mixture was poured into cooled (0-4° C., ice bath) aqueous saturated solution of ammonium chloride (5 mL) and extracted with ethyl acetate (2×10 mL). The combined organic phases were washed with brine (10 mL), dried (sodium sulfate) and concentrated in vacuo. The crude product was purified by column chromatography (silica gel, 12 g, eluting with methanol/dichloromethane, gradient 0:100 to 10:90) to afford the title compound as an off-white solid (68 mg, 64%). HPLC (method LCMS_fastgradient) $t_R$=1.13 min. $^1$H NMR (DMSO-d6, 300 MHz): δ 1.35 (d, J=6.8 Hz, 3H), 2.17 (d, J=0.8 Hz, 3H), 3.41-3.53 (m, 1H), 3.71 (dd, J=4.4, 10.1 Hz, 1H), 4.32 (dd, J=9.9, 9.9 Hz, 1H), 7.16-7.21 (m, 1H), 7.27 (dd, J=8.7, 9.1 Hz, 2H), 7.45-7.55 (m, 2H), 7.79-7.87 (m, 3H), 7.92-8.00 (m, 1H), 10.0 (s, 1H). MS (ES+) m/z 453.7, 455.7 [M+H, Cl isotopes].

Step 2: (S)- or (R)—N2-(3-Fluoro-4-(4-methyl-1H-imidazol-1-yl)phenyl)-7-(4-fluorophenyl)-N4,5-dimethyl-6,7-dihydro-5H-pyrrolo[2,3-d]pyrimidine-2,4-diamine (46p)

In a screw-cap vial, (S)- or (R)-4-chloro-N-(3-fluoro-4-(4-methyl-1H-imidazol-1-yl)phenyl)-7-(4-fluorophenyl)-5-methyl-6,7-dihydro-5H-pyrrolo[2,3-d]pyrimidin-2-amine (Int-48p, 68 mg, 150 µmol) was suspended in NMP (0.6 mL) and a solution of methylamine in ethanol (33% m/m, 707 mg, 935 µL, 7.51 mmol) was added. The vial was flushed with Argon and closed, the mixture was stirred at 120° C. for 18 h. After cooling to room temperature, water (20 mL) was added and the mixture was extracted with tertbutylmethyl ether (2×50 mL). The organic layers were combined, washed with brine (1×20 mL), dried (sodium sulfate) and concentrated in vacuo. The crude product was purified by column chromatography (silica gel, 12 g, eluting with methanol/dichloromethane, gradient 0:100 to 5:95) to yield the title compound as a light yellow foam (21 mg, 30%). HPLC (method LCMS_fastgradient) $t_R$=0.93 min. $^1$H NMR (CDCl3, 300 MHz): δ 1.31 (d, J=6.6 Hz, 3H), 2.32 (d, J=1.0 Hz, 3H), 3.11 (d, J=4.8 Hz, 3H), 3.26-3.37 (m, 1H), 3.54 (dd, J=4.0, 9.5 Hz, 1H), 4.13-4.23 (m, 2H), 6.91-6.98 (m, 2H), 7.07 (dd, J=8.3, 9.1 Hz, 2H), 7.12-7.25 (m, 2H), 7.60-7.68 (m, 3H), 8.13 (dd, J=2.2, 13.9 Hz, 1H). MS (ES+) m/z 448.8 [M+H]. Chiral HPLC: Chiralpak AD, eluent: n-heptane/ethanol, 80:20 v/v, isocratic, first eluting enantiomer, 96% ee.

Example 46q (R)— or (S)—N2-(3-Fluoro-4-(4-methyl-1H-imidazol-1-yl)phenyl)-7-(4-fluorophenyl)-N4,5-dimethyl-6,7-dihydro-5H-pyrrolo[2,3-d]pyrimidine-2,4-diamine

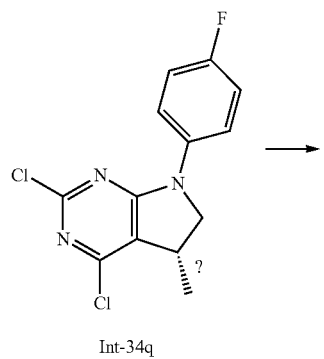

Int-34q

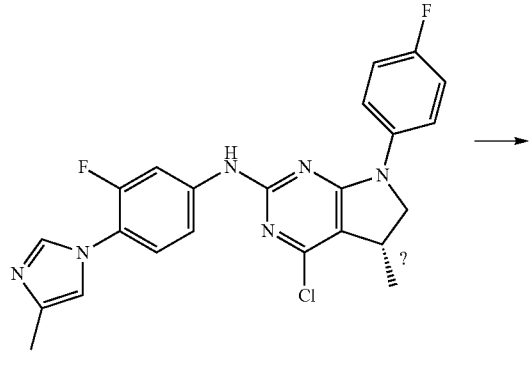

Int-48q

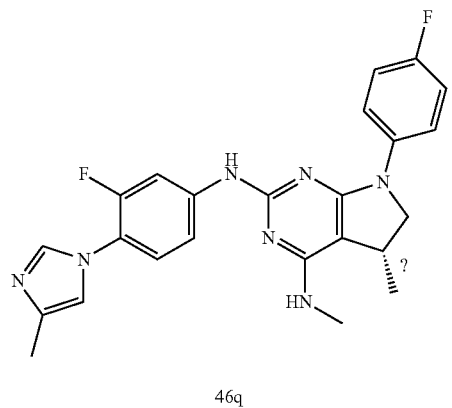

46q

Step 1: (R)— or (S)-4-Chloro-N-(3-fluoro-4-(4-methyl-1H-imidazol-1-yl)phenyl)-7-(4-fluorophenyl)-5-methyl-6,7-dihydro-5H-pyrrolo[2,3-d]pyrimidin-2-amine (Int-48q)

(+)-2,4-Dichloro-7-(4-fluorophenyl)-5-methyl-6,7-dihydro-5H-pyrrolo[2,3-d]pyrimidine (Int-34q, 69 mg, 231 μmol) and 3-fluoro-4-(4-methyl-1H-imidazol-1-yl)aniline (48.7 mg, 255 μmol) were dissolved in THF (3.0 mL) and a solution of lithium bis(trimethylsilyl)amide in THF/ethylbenzene (1.0 M, 278 μL, 278 μmol) was added at room temperature. The mixture was stirred for 30 min at room temperature. Then, a second portion of lithium bis(trimethylsilyl)amide in THF/ethylbenzene (1.0 M, 116 μL, 116 μmol) was added the mixture was stirred for further 90 min at room temperature. After that, the dark reaction mixture was poured into cooled (0-4° C., ice bath) aqueous saturated solution of ammonium chloride (5 mL) and extracted with ethyl acetate (2×10 mL). The combined organic phases were washed with brine (10 mL), dried (sodium sulfate) and concentrated in vacuo. The crude product was purified by column chromatography (silica gel, 12 g, eluting with methanol/dichloromethane, gradient 0:100 to 10:90) to afford the title compound as an off-white solid (72 mg, 69%). HPLC (method LCMS_fastgradient) $t_R$=1.17 min. $^1$H NMR (DMSO-d6, 300 MHz): δ 1.35 (d, J=6.8 Hz, 3H), 2.17 (d, J=0.8 Hz, 3H), 3.41-3.53 (m, 1H), 3.71 (dd, J=4.4, 10.1 Hz, 1H), 4.32 (dd, J=9.9, 9.9 Hz, 1H), 7.16-7.21 (m, 1H), 7.27 (dd, J=8.7, 9.1 Hz, 2H), 7.45-7.55 (m, 2H), 7.79-7.87 (m, 3H), 7.92-8.00 (m, 1H), 10.0 (s, 1H). MS (ES+) m/z 453.7, 455.7 [M+H, Cl isotopes].

Step 2: (R)— or (S)—N2-(3-Fluoro-4-(4-methyl-1H-imidazol-1-yl)phenyl)-7-(4-fluorophenyl)-N4,5-dimethyl-6,7-dihydro-5H-pyrrolo[2,3-d]pyrimidine-2,4-diamine (46q)

In a screw-cap vial, (R)- or (S)-4-chloro-N-(3-fluoro-4-(4-methyl-1H-imidazol-1-yl)phenyl)-7-(4-fluorophenyl)-5-methyl-6,7-dihydro-5H-pyrrolo[2,3-d]pyrimidin-2-amine (Int-48q, 71 mg, 157 μmol) was suspended in NMP (0.6 mL) and a solution of methylamine in ethanol (33% m/m, 738 mg, 976 μL, 7.84 mmol) was added. The vial was flushed with Argon and closed, the mixture was stirred at 120° C. for 16 h. After cooling to room temperature, water (20 mL) was added and the mixture was extracted with tertbutylmethyl ether (2×50 mL). The organic layers were combined, washed with brine (1×20 mL), dried (sodium sulfate) and concentrated in vacuo. The crude product was purified by column chromatography (silica gel, 12 g, eluting with methanol/dichloromethane, gradient 0:100 to 5:95) to yield the title compound as a yellow solid (55 mg, 74%). HPLC (method LCMS_fastgradient) $t_R$=0.92 min. $^1$H NMR (CDCl3, 300 MHz): δ 1.31 (d, J=6.6 Hz, 3H), 2.32 (d, J=1.0 Hz, 3H), 3.11 (d, J=4.8 Hz, 3H), 3.26-3.37 (m, 1H), 3.54 (dd, J=4.0, 9.5 Hz, 1H), 4.13-4.23 (m, 2H), 6.91-6.98 (m, 2H), 7.07 (dd, J=8.3, 9.1 Hz, 2H), 7.12-7.25 (m, 2H), 7.60-7.68 (m, 3H), 8.13 (dd, J=2.2, 13.9 Hz, 1H). MS (ES+) m/z 448.8 [M+H]. Chiral HPLC: Chiralpak AD, eluent: n-heptane/ethanol, 80:20 v/v, isocratic, second eluting enantiomer, 93% ee.

Example 47

7-(4-Fluorophenyl)-N4,5,5-trimethyl-N2-(4-(5-methyl-1,3,4-oxadiazol-2-yl)phenyl)-6,7-dihydro-5H-pyrrolo[2,3-d]pyrimidine-2,4-diamine

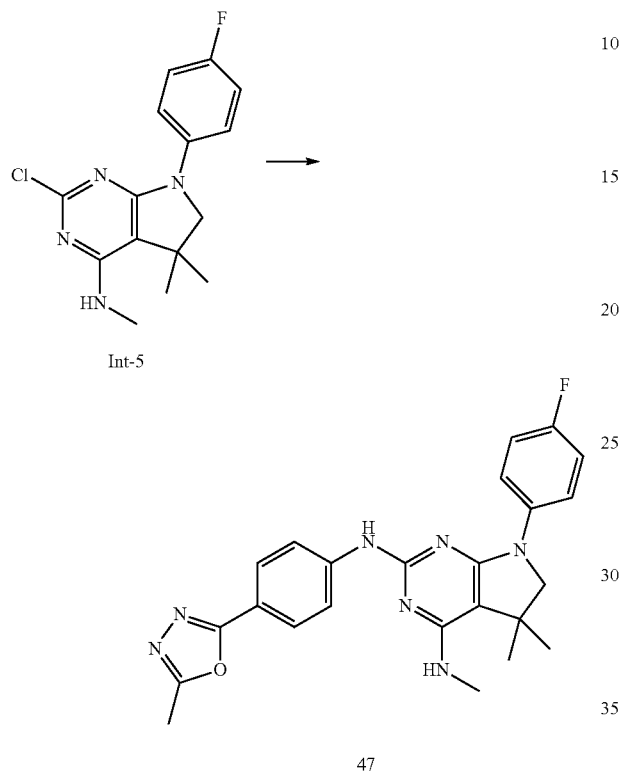

Int-5

47

In a 5 mL microwave vial, 2-chloro-7-(4-fluorophenyl)-N,5,5-trimethyl-6,7-dihydro-5H-pyrrolo[2,3-d]pyrimidin-4-amine (Int-5, 60 mg, 196 µmol) was dissolved in NMP (1.3 mL) and 4-(5-methyl-1,3,4-oxadiazol-2-yl)aniline (41.5 mg, 237 µmol), cesium carbonate (127 mg, 391 µmol), 2-dicyclohexylphosphino-2'-(N,N-dimethylamino)biphenyl (16.4 mg, 41.7 µmol), and bis(dibenzylideneacetone)palladium(0) (20.7 mg, 36 µmol) were added subsequently. The vial was flushed with Argon and sealed. The reaction mixture was heated under microwave irradiation at 150° C. for 30 minutes. After that, water (3 mL) was added and the mixture was extracted with tertbutylmethyl ether (TBME, 2×30 mL). The combined organic layers were washed with water (4×3 mL) and brine (1×20 mL), dried (sodium sulfate) and concentrated in vacuo. The crude product was purified by column chromatography (silica gel, 12 g, ethyl acetate/n-heptane, gradient 30:70 to 100:0), followed by a second column chromatography (silica gel, 12 g, 2 N ammonia in methanol/dichloromethane, gradient 1:99 to 2:98) to afford the title compound as a light brown lyophilized powder (49 mg, 56%). HPLC (method LCMS_fastgradient) $t_R$=1.16 min. $^1$H NMR (CDCl$_3$, 300 MHz): δ 1.42 (s, 6H), 2.61 (s, 3H), 3.11 (d, J=4.8 Hz, 3H), 3.68 (s, 2H), 4.23 (q, J=4.8 Hz, 1H), 7.03-7.11 (m, 3H), 7.59-7.66 (m, 2H), 7.81 (d, J=8.9 Hz, 2H), 7.95 (d, J=8.9 Hz, 2H). MS (ES+) m/z 446.2 [M+H].

All references cited herein are incorporated herein by reference in their entireties for all purposes.

The foregoing description is intended to illustrate various aspects of the present invention. It is not intended that the examples presented herein limit the scope of the appended claims. The invention now being described, it will be apparent to one of ordinary skill in the art that many changes and modifications can be made thereto without departing from the spirit or scope of the appended claims. It is further to be understood that the appended claims are representative of several of the various embodiments described herein, and that any embodiment so described but not expressed in one of the appended claims may be expressed in a claim in an application claiming benefit of priority to the instant application without any concomitant loss of priority.

The invention claimed is:
1. A compound of formula I,

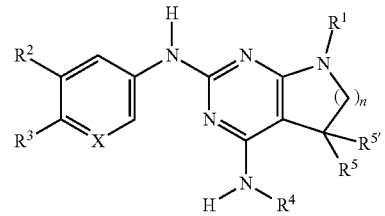

wherein:
R$^1$ is phenyl, lower alkyl, C$_{3-6}$-cycloalkyl, —CH$_2$—C$_{3-6}$-cycloalkyl, or bridged C$_{3-5}$-cycloalkyl, any of which are optionally substituted by one, two or three substituents selected from halogen, lower alkyl, or lower alkyl substituted by halogen;
R$^2$ is hydrogen, halogen, lower alkoxy, lower alkyl substituted by halogen, or lower alkoxy substituted by halogen;
R$^3$ is a five membered heteroaryl group, selected from:

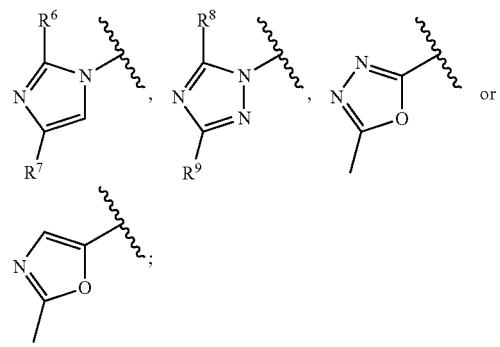

wherein:
R$^6$ is hydrogen or lower alkyl;
R$^7$ is halogen or lower alkyl;
R$^8$ is hydrogen or lower alkyl;
R$^9$ is hydrogen or lower alkyl;
R$^4$ is lower alkyl or lower alkyl substituted by hydroxy;
R$^5$ and R$^{5'}$ are independently from each other hydrogen or lower alkyl;
-( )$_n$- is —CH$_2$— or —CH$_2$CH$_2$— for n being respectively 1 or 2; and
X is CH or N;

or a pharmaceutically active acid addition salt thereof, or a racemic mixture or its corresponding individual enantiomers or optical isomers or stereoisomers thereof.

2. A compound of formula I-1,

I-1 wherein:
R$^1$ is phenyl, lower alkyl, C$_{3-6}$-cycloalkyl, —CH$_2$—C$_{3-6}$-cycloalkyl, or bridged C$_{3-5}$-cycloalkyl, any of which are optionally substituted by one, two or three substituents selected from halogen, lower alkyl or lower alkyl substituted by halogen;
R$^2$ is hydrogen, halogen, lower alkoxy, lower alkyl substituted by halogen, or lower alkoxy substituted by halogen;
R$^4$ is lower alkyl or lower alkyl substituted by hydroxy;
R$^5$ and R$^{5'}$ are independently from each other hydrogen or lower alkyl;
R$^6$ is hydrogen or lower alkyl;
R$^7$ is halogen or lower alkyl;
-( )$_n$- is —CH$_2$— or —CH$_2$CH$_2$— for n being respectively 1 or 2; and
X is CH or N;
or a pharmaceutically active acid addition salt thereof, or a racemic mixture or its corresponding individual enantiomers or optical isomers or stereoisomers thereof.

3. The compound of claim 2, selected from the group consisting of:
N2-(4-(4-Chloro-1H-imidazol-1-yl)-3-methoxyphenyl)-7-(4-fluorophenyl)-N4,5,5-trimethyl-6,7-dihydro-5H-pyrrolo[2,3-d]pyrimidine-2,4-diamine;
N2-(6-(4-Chloro-1H-imidazol-1-yl)-5-methoxypyridin-3-yl)-7-(4-fluorophenyl)-N4,5,5-trimethyl-6,7-dihydro-5H-pyrrolo[2,3-d]pyrimidine-2,4-diamine;
7-(4-Fluorophenyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine;
N2-(4-(2,4-Dimethyl-1H-imidazol-1-yl)-3-fluorophenyl)-7-(4-fluorophenyl)-N4,5,5-trimethyl-6,7-dihydro-5H-pyrrolo[2,3-d]pyrimidine-2,4-diamine;
7-(4-Fluorophenyl)-N4,5,5-trimethyl-N2-(4-(4-methyl-1H-imidazol-1-yl)phenyl)-6,7-dihydro-5H-pyrrolo[2,3-d]pyrimidine-2,4-diamine;
N2-(6-(4-Chloro-1H-imidazol-1-yl)-5-methoxypyridin-3-yl)-7-(3,4-difluorophenyl)-N4,5,5-trimethyl-6,7-dihydro-5H-pyrrolo[2,3-d]pyrimidine-2,4-diamine;
7-(3,4-Difluorophenyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine;
7-(3,3-Difluorocyclobutyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine;
7-(2,4-Difluorophenyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine;
N2-(5-Methoxy-6-(4-methyl-1H-imidazol-1-yl)pyridin-3-yl)-N4,5,5-trimethyl-7-(3-(trifluoromethyl)bicyclo[1.1.1]pentan-1-yl)-6,7-dihydro-5H-pyrrolo[2,3-d]pyrimidine-2,4-diamine;
N2-(6-(4-Chloro-1H-imidazol-1-yl)-5-methoxypyridin-3-yl)-7-(2,4-difluorophenyl)-N4,5,5-trimethyl-6,7-dihydro-5H-pyrrolo[2,3-d]pyrimidine-2,4-diamine;
N2-(5-Fluoro-6-(4-methyl-1H-imidazol-1-yl)pyridin-3-yl)-7-(4-fluorophenyl)-N4,5,5-trimethyl-6,7-dihydro-5H-pyrrolo[2,3-d]pyrimidine-2,4-diamine;
7-(2,4-Difluorophenyl)-N2-(5-fluoro-6-(4-methyl-1H-imidazol-1-yl)pyridin-3-yl)-N4,5,5-trimethyl-6,7-dihydro-5H-pyrrolo[2,3-d]pyrimidine-2,4-diamine;
2-((7-(4-Fluorophenyl)-2-((5-methoxy-6-(4-methyl-1H-imidazol-1-yl)pyridin-3-yl)amino)-5,5-dimethyl-6,7-dihydro-5H-pyrrolo[2,3-d]pyrimidin-4-yl)amino)ethanol;
2-((2-((6-(4-Chloro-1H-imidazol-1-yl)-5-methoxypyridin-3-yl)amino)-7-(4-fluorophenyl)-5,5-dimethyl-6,7-dihydro-5H-pyrrolo[2,3-d]pyrimidin-4-yl)amino)ethanol;
7-(4-Fluorophenyl)-N2-(5-methoxy-6-(4-methyl-1H-imidazol-1-yl)pyridin-3-yl)-N4-methyl-6,7-dihydro-5H-pyrrolo[2,3-d]pyrimidine-2,4-diamine;
N2-(3-Fluoro-4-(4-methyl-1H-imidazol-1-yl)phenyl)-7-(4-fluorophenyl)-N4,5,5-trimethyl-6,7-dihydro-5H-pyrrolo[2,3-d]pyrimidine-2,4-diamine;
N2-(5-Fluoro-6-(4-methyl-1H-imidazol-1-yl)pyridin-3-yl)-8-(4-fluorophenyl)-N4,5,5-trimethyl-5,6,7,8-tetrahydropyrido[2,3-d]pyrimidine-2,4-diamine;
N2-(3-Fluoro-4-(4-methyl-1H-imidazol-1-yl)phenyl)-8-(4-fluorophenyl)-N4,5,5-trimethyl-5,6,7,8-tetrahydropyrido[2,3-d]pyrimidine-2,4-diamine;
N2-(3-Fluoro-4-(4-methyl-1H-imidazol-1-yl)phenyl)-7-(4-fluorophenyl)-N4-methyl-6,7-dihydro-5H-pyrrolo[2,3-d]pyrimidine-2,4-diamine;
7-(4-Fluorophenyl)-N2-(5-methoxy-6-(4-methyl-1H-imidazol-1-yl)pyridin-3-yl)-N4,5-dimethyl-6,7-dihydro-5H-pyrrolo[2,3-d]pyrimidine-2,4-diamine;
7-(2,3-Difluorophenyl)-N2-(5-fluoro-6-(4-methyl-1H-imidazol-1-yl)pyridin-3-yl)-N4,5,5-trimethyl-6,7-dihydro-5H-pyrrolo[2,3-d]pyrimidine-2,4-diamine;
7-(2,3-Difluorophenyl)-N2-(3-fluoro-4-(4-methyl-1H-imidazol-1-yl)phenyl)-N4,5,5-trimethyl-6,7-dihydro-5H-pyrrolo[2,3-d]pyrimidine-2,4-diamine;
7-(2,3-Difluorophenyl)-N2-(5-methoxy-6-(4-methyl-1H-imidazol-1-yl)pyridin-3-yl)-N4,5,5-trimethyl-6,7-dihydro-5H-pyrrolo[2,3-d]pyrimidine-2,4-diamine;
7-(2-Chloro-4-fluorophenyl)-N2-(3-fluoro-4-(4-methyl-1H-imidazol-1-yl)phenyl)-N4,5,5-trimethyl-6,7-dihydro-5H-pyrrolo[2,3-d]pyrimidine-2,4-diamine;
(S)—N2-(3-Fluoro-4-(4-methyl-1H-imidazol-1-yl)phenyl)-7-(4-fluorophenyl)-N4,5-dimethyl-6,7-dihydro-5H-pyrrolo[2,3-d]pyrimidine-2,4-diamine; and
(R)—N2-(3-Fluoro-4-(4-methyl-1H-imidazol-1-yl)phenyl)-7-(4-fluorophenyl)-N4,5-dimethyl-6,7-dihydro-5H-pyrrolo[2,3-d]pyrimidine-2,4-diamine.

4. A compound of formula I-2,

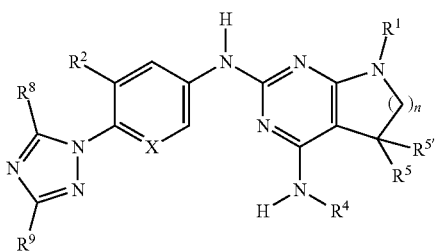

wherein:
R¹ is phenyl, lower alkyl, $C_{3-6}$-cycloalkyl, —$CH_2$—$C_{3-6}$-cycloalkyl, or bridged $C_{3-5}$-cycloalkyl, any of which are optionally substituted by one, two or three substituents selected from halogen, lower alkyl or lower alkyl substituted by halogen;
R² is hydrogen, halogen, lower alkoxy, lower alkyl substituted by halogen, or lower alkoxy substituted by halogen;
R⁴ is lower alkyl or lower alkyl substituted by hydroxy;
R⁵ and R⁵' are independently from each other hydrogen or lower alkyl;
R⁸ is hydrogen or lower alkyl;
R⁹ is halogen or lower alkyl;
-( )$_n$- is —$CH_2$— or —$CH_2CH_2$— for n being respectively 1 or 2; and
X is CH or N;
or a pharmaceutically active acid addition salt thereof, or a racemic mixture or its corresponding individual enantiomers or optical isomers or stereoisomers thereof.

5. The compound of claim 4, selected from the group consisting of:
7-(4-Fluorophenyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine;
N2-(3-(Difluoromethoxy)-4-(3-methyl-1H-1,2,4-triazol-1-yl)phenyl)-7-(4-fluorophenyl)-N4,5,5-trimethyl-6,7-dihydro-5H-pyrrolo[2,3-d]pyrimidine-2,4-diamine;
N2-(3-Fluoro-4-(3-methyl-1H-1,2,4-triazol-1-yl)phenyl)-7-(4-fluorophenyl)-N4,5,5-trimethyl-6,7-dihydro-5H-pyrrolo[2,3-d]pyrimidine-2,4-diamine;
N2-(3-Fluoro-4-(5-methyl-1H-1,2,4-triazol-1-yl)phenyl)-7-(4-fluorophenyl)-N4,5,5-trimethyl-6,7-dihydro-5H-pyrrolo[2,3-d]pyrimidine-2,4-diamine;
7-(3,4-Difluorophenyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine;
7-(3,4-Difluorophenyl)-N2-(3-fluoro-4-(3-methyl-1H-1,2,4-triazol-1-yl)phenyl)-N4,5,5-trimethyl-6,7-dihydro-5H-pyrrolo[2,3-d]pyrimidine-2,4-diamine;
7-(4-Fluorophenyl)-N4,5,5-trimethyl-N2-(4-(3-methyl-1H-1,2,4-triazol-1-yl)phenyl)-6,7-dihydro-5H-pyrrolo[2,3-d]pyrimidine-2,4-diamine;
7-(4-Fluorophenyl)-N4,5,5-trimethyl-N2-(6-(3-methyl-1H-1,2,4-triazol-1-yl)pyridin-3-yl)-6,7-dihydro-5H-pyrrolo[2,3-d]pyrimidine-2,4-diamine;
7-(3,3-Difluorocyclobutyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine;
7-(2,4-Difluorophenyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine;
N2-(3-Methoxy-4-(3-methyl-1H-1,2,4-triazol-1-yl)phenyl)-N4,5,5-trimethyl-7-(3-(trifluoromethyl)bicyclo[1.1.1]pentan-1-yl)-6,7-dihydro-5H-pyrrolo[2,3-d]pyrimidine-2,4-diamine;
7-(2,4-Difluorophenyl)-N2-(3-fluoro-4-(3-methyl-1H-1,2,4-triazol-1-yl)phenyl)-N4,5,5-trimethyl-6,7-dihydro-5H-pyrrolo[2,3-d]pyrimidine-2,4-diamine;
2-((7-(4-Fluorophenyl)-2-((3-methoxy-4-(3-methyl-1H-1,2,4-triazol-1-yl)phenyl)amino)-5,5-dimethyl-6,7-dihydro-5H-pyrrolo[2,3-d]pyrimidin-4-yl)amino)ethanol;
2-((2-((3-Fluoro-4-(3-methyl-1H-1,2,4-triazol-1-yl)phenyl)amino)-7-(4-fluorophenyl)-5,5-dimethyl-6,7-dihydro-5H-pyrrolo[2,3-d]pyrimidin-4-yl)amino)ethanol;
7-(4-Fluorophenyl)-N2-(3-methoxy-4-(3-methyl-1H-1,2,4-triazol-1-yl)phenyl)-N4-methyl-6,7-dihydro-5H-pyrrolo[2,3-d]pyrimidine-2,4-diamine;
8-(4-Fluorophenyl)-N2-(3-methoxy-4-(3-methyl-1H-1,2,4-triazol-1-yl)phenyl)-N4,5,5-trimethyl-5,6,7,8-tetrahydropyrido[2,3-d]pyrimidine-2,4-diamine;
7-(4-Fluorophenyl)-N2-(3-methoxy-4-(3-methyl-1H-1,2,4-triazol-1-yl)phenyl)-N4,5-dimethyl-6,7-dihydro-5H-pyrrolo[2,3-d]pyrimidine-2,4-diamine; and
7-(2,3-Difluorophenyl)-N2-(3-methoxy-4-(3-methyl-1H-1,2,4-triazol-1-yl)phenyl)-N4,5,5-trimethyl-6,7-dihydro-5H-pyrrolo[2,3-d]pyrimidine-2,4-diamine.

6. A compound of formula 3

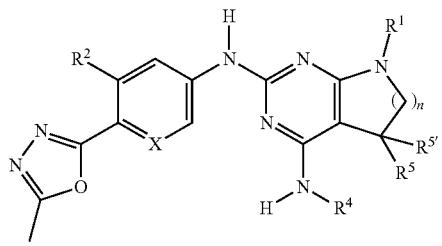

wherein:
R¹ is phenyl, lower alkyl, $C_{3-6}$-cycloalkyl, —$CH_2$—$C_{3-6}$-cycloalkyl, or bridged $C_{3-5}$-cycloalkyl, any of which are optionally substituted by one, two or three substituents selected from halogen, lower alkyl, or lower alkyl substituted by halogen;
R² is hydrogen, halogen, lower alkoxy, lower alkyl substituted by halogen, or lower alkoxy substituted by halogen;
R⁴ is lower alkyl or lower alkyl substituted by hydroxy;
R⁵ and R⁵' are independently from each other hydrogen or lower alkyl;
-( )$_n$- is —$CH_2$— or —$CH_2CH_2$— for n being respectively 1 or 2; and
X is CH or N;
or a pharmaceutically active acid addition salt thereof, or a racemic mixture or its corresponding individual enantiomers or optical isomers or stereoisomers thereof.

7. The compound of claim 6, selected from:
7-(4-Fluorophenyl)-N2-(3-methoxy-4-(5-methyl-1,3,4-oxadiazol-2-yl)phenyl)-N4,5,5-trimethyl-6,7-dihydro-5H-pyrrolo[2,3-d]pyrimidine-2,4-diamine; and
7-(4-Fluorophenyl)-N4,5,5-trimethyl-N2-(4-(5-methyl-1,3,4-oxadiazol-2-yl)phenyl)-6,7-dihydro-5H-pyrrolo[2,3-d]pyrimidine-2,4-diamine.

8. A compound of formula 4

I-4 wherein:
R¹ is phenyl, lower alkyl, $C_{3-6}$-cycloalkyl, —$CH_2$—$C_{3-6}$-cycloalkyl, or bridged $C_{3-5}$-cycloalkyl, any of which are optionally substituted by one, two or three substituents selected from halogen, lower alkyl, or lower alkyl substituted by halogen;
R² is hydrogen, halogen, lower alkoxy, lower alkyl substituted by halogen, or lower alkoxy substituted by halogen;
R⁴ is lower alkyl or lower alkyl substituted by hydroxy;
R⁵ and R⁵' are independently from each other hydrogen or lower alkyl;
-( )ₙ- is —$CH_2$— or —$CH_2CH_2$— for n being respectively 1 or 2; and
X is CH or N;
or a pharmaceutically active acid addition salt thereof, or a racemic mixture or its corresponding individual enantiomers or optical isomers or stereoisomers thereof.

9. The compound of claim 8, having formula N2-(3-Fluoro-4-(2-methyloxazol-5-yl)phenyl)-7-(4-fluorophenyl)-N4,5,5-trimethyl-6,7-dihydro-5H-pyrrolo[2,3-d]pyrimidine-2,4-diamine.

10. A process for preparing a compound of formula I,

I which process comprises:
a) reacting a compound of formula II

II with a compound of formula III

III to form a compound of formula I;
and, optionally, further converting the compound obtained into a pharmaceutically acceptable acid addition salt;
or
b) reacting a compound of formula V

V with an amine of formula $H_2NR^4$
to form a compound of formula I;
and optionally converting the compound obtained into a pharmaceutically acceptable acid addition salt, and
wherein, in a) or b):
R¹ is phenyl, lower alkyl, $C_{3-6}$-cycloalkyl, —$CH_2$—$C_{3-6}$-cycloalkyl, or bridged $C_{3-5}$-cycloalkyl, any of which are optionally substituted by one, two or three substituents selected from halogen, lower alkyl, or lower alkyl substituted by halogen;
R² is hydrogen, halogen, lower alkoxy, lower alkyl substituted by halogen, or lower alkoxy substituted by halogen;
R³ is a five membered heteroaryl group, selected from:

wherein:
R⁶ is hydrogen or lower alkyl;
R⁷ is halogen or lower alkyl;
R⁸ is hydrogen or lower alkyl;
R⁹ is hydrogen or lower alkyl;
R⁴ is lower alkyl or lower alkyl substituted by hydroxy;
R⁵ and R⁵' are independently from each other hydrogen or lower alkyl;
-( )ₙ- is —$CH_2$— or —$CH_2CH_2$— for n being respectively 1 or 2;
X is CH or N;
and Y is halogen.

11. A medicament containing one or more compounds according to formula I,

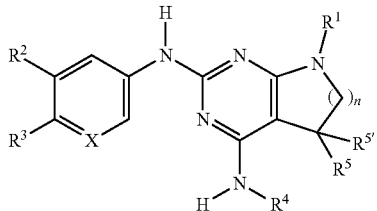

wherein:
$R^1$ is phenyl, lower alkyl, $C_{3-6}$-cycloalkyl, —$CH_2$—$C_{3-6}$-cycloalkyl, or bridged $C_{3-5}$-cycloalkyl, any of which are optionally substituted by one, two or three substituents selected from halogen, lower alkyl, or lower alkyl substituted by halogen;
$R^2$ is hydrogen, halogen, lower alkoxy, lower alkyl substituted by halogen, or lower alkoxy substituted by halogen;
$R^3$ is a five membered heteroaryl group, selected from:

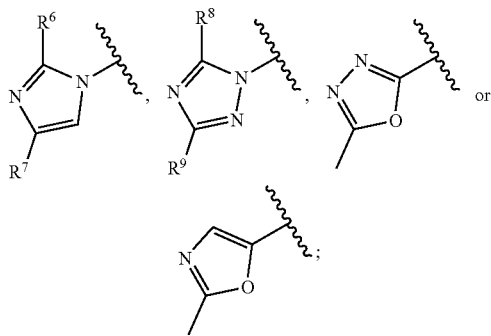

wherein:
$R^6$ is hydrogen or lower alkyl;
$R^7$ is halogen or lower alkyl;
$R^8$ is hydrogen or lower alkyl;
$R^9$ is hydrogen or lower alkyl;
$R^4$ is lower alkyl or lower alkyl substituted by hydroxy;
$R^5$ and $R^{5'}$ are independently from each other hydrogen or lower alkyl;
-( )$_n$- is —$CH_2$— or —$CH_2CH_2$— for n being respectively 1 or 2; and
X is CH or N;
or a pharmaceutically active acid addition salt thereof, a racemic mixture or its corresponding individual enantiomers or optical isomers or stereoisomers thereof, and one or more pharmaceutically acceptable excipients.

12. A method for treating Alzheimer's disease, cerebral amyloid angiopathy, hereditary cerebral hemorrhage with amyloidosis, Dutch-type (HCHWA-D), multi-infarct dementia, dementia pugilistica, or Down syndrome, which method comprises administering to a patient in need thereof an effective amount of a compound according to formula I

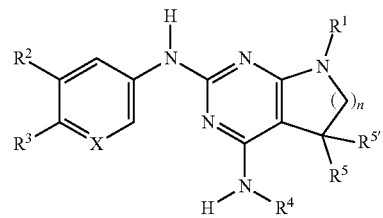

wherein:
$R^1$ is phenyl, lower alkyl, $C_{3-6}$-cycloalkyl, —$CH_2$—$C_{3-6}$-cycloalkyl, or bridged $C_{3-5}$-cycloalkyl, any of which are optionally substituted by one, two or three substituents selected from halogen, lower alkyl, or lower alkyl substituted by halogen;
$R^2$ is hydrogen, halogen, lower alkoxy, lower alkyl substituted by halogen, or lower alkoxy substituted by halogen;
$R^3$ is a five membered heteroaryl group, selected from:

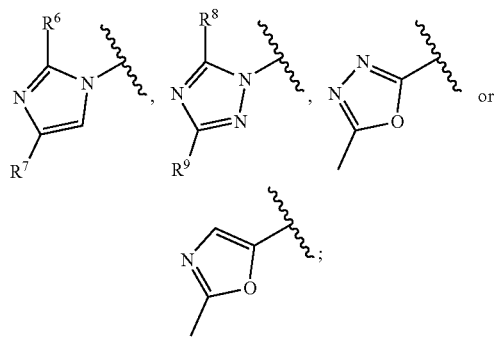

wherein:
$R^6$ is hydrogen or lower alkyl;
$R^7$ is halogen or lower alkyl;
$R^8$ is hydrogen or lower alkyl;
$R^9$ is hydrogen or lower alkyl;
$R^4$ is lower alkyl or lower alkyl substituted by hydroxy;
$R^5$ and $R^{5'}$ are independently from each other hydrogen or lower alkyl;
-( )$_n$- is —$CH_2$— or —$CH_2CH_2$— for n being respectively 1 or 2; and
X is CH or N;
or a pharmaceutically active acid addition salt thereof, a racemic mixture or its corresponding individual enantiomers or optical isomers or stereoisomers thereof.

13. The process of claim 10, wherein:
in a), the reacting of the compound of formula II with the compound of formula III, is carried out in the presence of a catalytic or stoichiometric amount of bis(dibenzylideneacetone)palladium(0), and a catalytic or stoichiometric amount of a 2-dicyclohexylphosphino-2'-(N,Ndimethylamino)biphenyl, and an alkali metal carbonate or phosphate,
and wherein the reaction is carried out in a polar aprotic solvent at a temperature between 100° C. and 170° C.

14. The process of claim 10, wherein:
in b), the reacting of the compound of formula V with the amine is carried out using an excess of the amine at a temperature of 100° C. to 140° C., in a polar, high boiling solvent.

15. The process of claim 10, wherein, in a), Y is chlorine or bromine.

16. The process of claim 10, wherein, in b), Y is chlorine.

17. The medicament of claim 11, wherein:
$R^3$ is

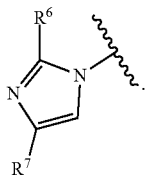

18. The medicament of claim 11, wherein:
$R^3$ is

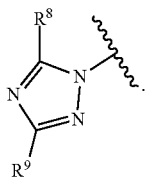

19. The medicament of claim 11, wherein:
$R^3$ is

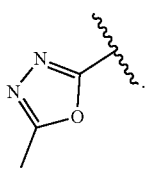 [SMILES: *c1nnc(C)o1]

20. The medicament of claim 11, wherein:
$R^3$ is

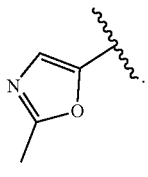 [SMILES: *c1cnc(C)o1]

21. The method of claim 12, wherein:
$R^3$ is

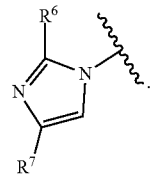

22. The method of claim 12, wherein:
$R^3$ is

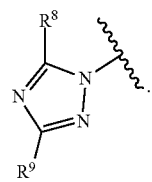

23. The method of claim 12, wherein:
$R^3$ is

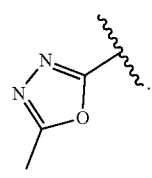

24. The method of claim 12, wherein:
$R^3$ is

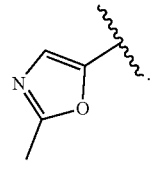 [SMILES: *c1cnc(C)o1]

* * * * *